(12) United States Patent
Barany et al.

(10) Patent No.: US 7,312,039 B2
(45) Date of Patent: *Dec. 25, 2007

(54) DETECTION OF NUCLEIC ACID SEQUENCE DIFFERENCES USING COUPLED LIGASE DETECTION AND POLYMERASE CHAIN REACTIONS

(75) Inventors: Francis Barany, New York, NY (US); Matthew Lubin, Rye Brook, NY (US); George Barany, Falcon Heights, MN (US); Robert P. Hammer, Baton Rouge, LA (US)

(73) Assignees: Cornell Research Foundation, Inc., Ithaca, NY (US); Regents of the University of Minnesota, Minneapolis, MN (US); Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/590,056

(22) Filed: Oct. 31, 2006

(65) Prior Publication Data

US 2007/0048783 A1    Mar. 1, 2007

Related U.S. Application Data

(60) Continuation of application No. 11/229,366, filed on Sep. 16, 2005, which is a continuation of application No. 10/843,720, filed on May 12, 2004, now Pat. No. 7,166,434, which is a continuation of application No. 09/918,156, filed on Jul. 30, 2001, now Pat. No. 6,797,470, which is a continuation of application No. 09/440,523, filed on Nov. 15, 1999, now Pat. No. 6,268,148, which is a division of application No. 08/864,473, filed on May 28, 1997, now Pat. No. 6,027,889.

(60) Provisional application No. 60/018,532, filed on May 29, 1996.

(51) Int. Cl.
C12Q 1/68 (2006.01)
C12P 19/34 (2006.01)
(52) U.S. Cl. ........................................ 435/6; 435/91.2
(58) Field of Classification Search ................... 435/6, 435/91.1, 91.2
See application file for complete search history.

(56) References Cited

U.S. PATENT DOCUMENTS 4,683,202 A    7/1987    Mullis et al.

(Continued)

FOREIGN PATENT DOCUMENTS

EP    0 357 011 A2    8/1989

(Continued)

OTHER PUBLICATIONS

Nucleic Acid Hybridization, A Practical Approach, p. 6, edited by Hames & Higgins, 1985, Published by IRL Press Limited, P.O. Box 1, Eynsham, Oxford OX 8 1JJ, England.

(Continued)

*Primary Examiner*—Kenneth R. Horlick
(74) *Attorney, Agent, or Firm*—Nixon Peabody LLP

(57) ABSTRACT

The present invention relates to a method for identifying a target nucleotide sequence. This method involves forming a ligation product on a target nucleotide sequence in a ligase detection reaction mixture, amplifying the ligation product to form an amplified ligation product in a polymerase chain reaction (PCR) mixture, detecting the amplified ligation product, and identifying the target nucleotide sequence. Such coupling of the ligase detection reaction and the polymerase chain reaction permits multiplex detection of nucleic acid sequence differences.

5 Claims, 29 Drawing Sheets

U.S. PATENT DOCUMENTS

| | | | |
|---|---|---|---|
| 4,883,750 A | 11/1989 | Whiteley |
| 4,988,617 A | 1/1991 | Landegren |
| 5,035,996 A | 7/1991 | Hartley |
| 5,104,792 A | 4/1992 | Silver et al. |
| 5,143,854 A | 9/1992 | Pirrung |
| 5,202,231 A | 4/1993 | Drmanac |
| 5,258,506 A | 11/1993 | Urdea et al. |
| 5,278,298 A | 1/1994 | Chakraborty |
| 5,288,468 A | 2/1994 | Church et al. |
| 5,290,925 A | 3/1994 | Fino |
| 5,314,809 A | 5/1994 | Erlich et al. |
| 5,324,633 A | 6/1994 | Fodor |
| 5,352,582 A | 10/1994 | Lichtenwalter et al. |
| 5,371,241 A | 12/1994 | Brush |
| 5,391,480 A | 2/1995 | Davis et al. |
| 5,405,783 A | 4/1995 | Pirrung et al. |
| 5,407,798 A | 4/1995 | Martinelli et al. |
| 5,412,087 A | 5/1995 | McGall et al. |
| 5,415,839 A | 5/1995 | Zaun et al. |
| 5,418,149 A | 5/1995 | Gelfand et al. |
| 5,424,186 A | 6/1995 | Fodor et al. |
| 5,429,807 A | 7/1995 | Matson et al. |
| 5,445,934 A | 8/1995 | Fodor et al. |
| 5,470,705 A | 11/1995 | Grossman et al. |
| 5,494,810 A | 2/1996 | Barany et al. |
| 5,510,270 A | 4/1996 | Fodor et al. |
| 5,512,441 A | 4/1996 | Ronai |
| 5,516,635 A | 5/1996 | Ekins et al. |
| 5,525,464 A | 6/1996 | Drmanac et al. |
| 5,527,681 A | 6/1996 | Holmes |
| 5,536,649 A | 7/1996 | Fraiser et al. |
| 5,593,826 A | 1/1997 | Fung et al. |
| 5,593,840 A | 1/1997 | Bhatnagar et al. |
| 5,594,121 A | 1/1997 | Froehler |
| 5,648,213 A | 7/1997 | Reddy et al. |
| 5,667,974 A | 9/1997 | Birkenmeyer |
| 5,695,934 A | 12/1997 | Brenner |
| 5,700,637 A | 12/1997 | Southern |
| 5,723,320 A | 3/1998 | Dehlinger |
| 5,731,171 A | 3/1998 | Bohlander |
| 5,744,305 A | 4/1998 | Fodor et al. |
| 5,800,984 A | 9/1998 | Vary |
| 5,834,181 A | 11/1998 | Shuber |
| 5,837,832 A | 11/1998 | Chee et al. |
| 5,858,659 A | 1/1999 | Sapolsky |
| 5,868,136 A | 2/1999 | Fox et al. |
| 5,876,924 A | 3/1999 | Zhang et al. |
| 5,912,148 A | 6/1999 | Eggerding |
| 5,932,711 A | 8/1999 | Boles et al. |
| 5,942,391 A | 8/1999 | Zhang et al. |
| 5,981,176 A | 11/1999 | Wallace |
| 6,027,889 A | 2/2000 | Barany et al. |
| 6,143,495 A | 11/2000 | Lizardi |
| 6,156,501 A | 12/2000 | McGall et al. |
| 6,180,338 B1 | 1/2001 | Adams |
| 6,268,148 B1 | 7/2001 | Barany et al. |
| 6,322,971 B1 | 11/2001 | Chetverin et al. |
| 6,506,594 B1 | 1/2003 | Barany et al. |
| 6,569,647 B1 | 5/2003 | Zhang et al. |
| 6,797,470 B2 | 9/2004 | Barany et al. |
| 6,852,487 B1 | 2/2005 | Barany et al. |
| 7,014,994 B1* | 3/2006 | Barany et al. ............ 435/6 |
| 7,083,917 B2* | 8/2006 | Barany et al. ............ 435/6 |
| 7,097,980 B2 | 8/2006 | Barany et al. |
| 7,166,434 B2 | 1/2007 | Barany et al. |
| 2002/0150921 A1 | 10/2002 | Barany et al. |
| 2003/0022182 A1 | 1/2003 | Barany et al. |
| 2003/0175750 A1 | 9/2003 | Barany et al. |
| 2004/0253625 A1 | 12/2004 | Barany et al. |
| 2004/0259141 A1 | 12/2004 | Barany et al. |
| 2006/0024731 A1 | 2/2006 | Barany et al. |
| 2006/0183149 A1 | 8/2006 | Barany et al. |
| 2007/0042419 A1 | 2/2007 | Barany et al. |
| 2007/0054305 A1 | 3/2007 | Barany et al. |
| 2007/0054306 A1 | 3/2007 | Barany et al. |

FOREIGN PATENT DOCUMENTS

| | | |
|---|---|---|
| EP | 0 387 696 A2 | 3/1990 |
| EP | 0 487 104 A1 | 5/1992 |
| EP | 0 601 714 A1 | 6/1994 |
| EP | 0 624 643 A2 | 11/1994 |
| EP | 0 628 640 A1 | 12/1994 |
| WO | WO 89/10977 | 11/1989 |
| WO | WO 90/11372 | 10/1990 |
| WO | WO 90/15070 | 12/1990 |
| WO | WO 92/10558 | 6/1992 |
| WO | WO 92/10566 | 6/1992 |
| WO | WO 92/10588 | 6/1992 |
| WO | WO 92/16655 | 10/1992 |
| WO | WO 93/04199 | 3/1993 |
| WO | WO 93/09250 | 5/1993 |
| WO | WO 93/17126 | 9/1993 |
| WO | WO 93/20227 | 10/1993 |
| WO | WO 93/20236 | 10/1993 |
| WO | WO 93/22680 | 11/1993 |
| WO | WO 93/25563 | 12/1993 |
| WO | WO 94/01446 | 1/1994 |
| WO | WO 94/09022 | 4/1994 |
| WO | WO 94/11530 | 5/1994 |
| WO | WO 94/17206 | 8/1994 |
| WO | WO 94/17210 | 8/1994 |
| WO | WO 91/17239 | 11/1994 |
| WO | WO 95/00533 | 1/1995 |
| WO | WO 95/35390 | 12/1995 |
| WO | WO 96/06190 | 2/1996 |
| WO | WO 96/15271 | 5/1996 |
| WO | WO 97/31256 | 8/1997 |
| WO | WO 98/03673 A | 1/1998 |
| WO | WO 00/56927 A3 | 9/2000 |

OTHER PUBLICATIONS

Nonradioactive In Situ Hybridization Application Manual, Indianapolis, Indiana: Boehringer Mannheim Corporation, Chapter III (1992).

Abravaya et al., "Detection of Point Mutations with a Modified Ligase Chain Reaction (Gap-LCR)," *Nucleic Acids Research* 23(4):675-682 (1995).

Bains, W., "Mixed Hybridization and Conventional Strategies for DNA Sequencing," *GATA* 10(3-4):84-94 (1993).

Barany, "Genetic Disease Detection And DNA Amplification Using Cloned Thermostable Ligase," *Proc. Natl. Acad. Sci. USA* 88:189-193 (1991).

Barany, "Ligase Chain Reaction (LCR)—Overview and Applications," *PCR Methods and Applications* 3(4):S51-S64 (1994).

Barany, F., "Cloning, Overexpression, And Nucleotide Sequence Of A Thermostable DNA Ligase Gene," *Gene* 109:1-11 (1991).

Barany, F., "The Ligase Chain Reaction in a PCR World," *PCR Methods and Applications* 1:5-16 (1991).

Beattie et al., "Advances in Genosensor Research," *Clin. Chem.* 41(5) 700-706 (1995).

Belgrader et al., "A Multiplex PCR-Ligase Detection Reaction Assay for Human Identity Testing," *Genome Science & Tech.* 1:77-87 (1996).

Biancalana et al., "Moderate Instability of the Trinucleotide Repeat in Spino Bulbar Muscular Atrophy," *Hum. Mol. Genet.* 1(4):255-258 (1992).

Bronner et al., "Mutation in the DNA Mismatch Repair Gene Homologue *hMLH1* is Associated with Hereditary Non-Polyposis Colon Cancer," *Nature* 368:258-261 (1994).
Buyse et al., "Rapid DNA Typing of Class II HLA Antigens Using the Polymerase Chain Reaction and Reverse and Reverse Dot Blot Hybridization," *Tissue Antigens* 41:1-14 (1993).
Cairns et al., "Homozygous Deletions of 9p21 in Primary Human Bladder Tumors Detected by Comparative Multiple Polymerase Chain Reaction," *Cancer Res.* 54:1422-1424 (1994).
Cawkwell et al., "Frequency of Allele Loss of *DCC*, p. 53, *RB1, WT1, NF1, NM23*, and *PC/MCC* in Colorectal Cancer Assayed by Fluorescent Multiplex of Polymerase Chain Reaction," *Br. J. Cancer* 70(5):813-818 (1994).
Celi et al., "A Rapid and Versatile Method to Synthesize Internal Standards for Competitive PCR," *Nucleic Acids Research* 21(4):1047 (1993).
Chamberlain et al., "Deletion Screening of the Duchenne Muscular Dystrophy Locus Via Multiplex DNA Amplification," *Nucleic Acids Research* 16(23):11141-11156 (1988).
Chan et al., "Polymeric Self-Assembled Monolayers. 3. Pattern Transfer by Use of Photolithography, Electrochemical, Methods and an Ultrathin, Self-Assembled Diacetylenic Resist," *J. Am. Chem. Soc.* 117:5875-5976 (1995).
Chee et al., "Accessing Genetic Information with High-Density DNA Arrays," *Science* 274:610-614 (1996).
Chehab et al., "Detection of Specific DNA Sequences by Fluorescence Amplification: A Color Complementation Assay," *Proc. Natl. Acad. Sci. USA* 86:9178-9182 (1989).
Cheng et al., "In Situ Attenuated Total Reflectance Fourier Transform Infrared Spectroscopy of Carboxylate-Bearing, Siloxane-Anchored, Self-Assembled Monolayers: A Study of Carboxylate Reactivity and Acid-Base Properties," *Langmuir* 11:1190-1195 (1995).
Chetverin et al., "Sequencing of Pools of Nucleic Acids on Oligonucleotide Arrays," *BioSystems* 30:215-231 (1993).
Chung et al., "Evidence for a Mechanism Predisposing to Intergenerational CAG Repeat Instability in Spinocerebeller Ataxia Type I," *Nat. Genet.* 5:254-258 (1993).
Cronin et al., "Cystic Fibrosis Mutation Detection by Hybridization to Light-Generated DNA Probe Arrays," *Human Mutation* 7:244-255 (1996).
Davis et al., "Quantitative Detection of Hepatitis C Virus RNA With a solid-Phase Signal Amplification Method: Definition of Optimal Conditions for Specimen Collection and Clinical Application in Interferon-Treated Patients," *Hepatology* 19(6):1337-1341 (1994).
Day et al., "Detection Of Steroid 21-Hydroxylase Alleles Using Gene-Specific PCR and a Multiplexed Ligation Detection Reaction," *Genomics* 29:152-162 (1995).
Day et al., "Identification of Non-Amplifying CYP21 Genes When Using PCR-Based Diagnosis of 21-Hydroylase Deficiency in Congenital Adrenal Hyperplasisa (CAH) Affected Pedigrees," *Hum. Mol. Genet.* 5(12):2039-2048 (1996).
Deng et al., "An Improved Method of Competitive PCR for Quantitation of Gene Copy Number," *Nucleic Acids Research* 21(20):4848-4849 (1993).
Drobyshev et al., "Sequence Analysis by Hybridization with Oligonucleotide Microchip: Identification of β-Thalassemia Mutations," *Gene* 188:45-52 (1997).
Fishel et al., "The Human Mutator Gene Homolog *MSH2* and its Association with Hereditary Nonpolyposis Colon Cancer," *Cell* 75:1027-1038 (1993).
Fodor et al., "Multiplexed Biochemical Assays with Biological Chips," *Nature* 364:555-556 (1993).

Gerry et al., "Universal DNA Microarray Method for Multiplex Detection of Low Abundance Point Mutations," *J. Mol. Biol.* 292:251-262 (1999).
Gibbs et al., "Detection of Single DNA Base Differences by Competitive Oligonucleotide Priming," *Nucleic Acids Research* 17(7):2437-2448 (1989).
Gonzalez-Zulueta et al., "Microsatellite Instability in Bladder Cancer," *Cancer Res.* 53:5620-5623 (1993).
Graham et al., "Gene Probe Assays on a Fibre-Optic Evanescent Wave Biosensor," *Biosensors & Bioelectronics* 7:487-493 (1992).
Grossman et. al., "High-Density Multiplex Detection of Nucleic Acid Sequences: Oligonucleotide Ligation Assay and Sequence-Coded Separation," *Nucleic Acids Research* 22(21):4527-4534 (1994).
Guo et al., "Direct Fluorescence Analysis of Genetic Polymorphisms by Hybridization with Oligonucleotide Arrays on Glass Supports," *Nucleic Acids Research* 22:5456-5465 (1994).
Gyllensten et al., "PCR-Based HLA Class II Typing," *PCR Methods and Applications* 1:91-98 (1991).
Hacia et al., "Detection of Heterozygous Mutations in *BRCA1* Using High Density Oligonucleotide Arrays and Two-Colour Fluorescence Analysis," *Nature Genetics* 14:441-447 (1996).
Hames, B.D. & Higgins, S.J. et al., "Nucleic Acid Hybridisation: A Practical Approach," IRL Press, Oxford, Washington D.C., pp. 5-7 (1985).
Han et al., "Genetic Instability in Pancreatic Cancer and Poorly Differentiated Type of Gastric Cancer," *Cancer Res.* 53:5087-5089 (1993).
Heller et al., "Discovery and Analysis of Inflammatory Disease-Related Genes Using cDNA Microarrays," *Proc. Nat'l. Acad. Sci. USA* 94:2150-2155 (1997).
Hollstein et al., "p53 Mutations in Human Cancers," *Science* 253:49-53 (1991).
Hsuih et al., "Novel, Ligation-Dependent PCR Assay for Detection of Hepatitis C Virus in Serum," *J. Clin. Microbiol.* 34(3):501-507 (1996).
Imbert et al., "Origin of the Expansion Mutation in Myotonic Dystrophy," *Nat. Genet.* 4:72-76 (1993).
Ionov et al., "Ubiquitous Somatic Mutations in Simple Repeated Sequences Reveal a New Mechanism for Colonic Carcinogenesis," *Nature* 363:558-561 (1993).
Iovannisci et al., "Ligation Amplification and Fluorescence Detection of Mycobacterium Tuberculosis DNA," *Mol. Cell. Probes* 7(1):35-43 (1993).
Janssen et al., "Evaluation of the DNA Fingerprinting Method AFLP as a New Tool in Bacterial Taxonomy," *Microbiology* 142:1881-1893 (1996).
Jin et al., "Alternating Current Impedance Characterization of the Structure of Alkylsiloxane Self-Assembled Monolayers on Silicon," *Langmuir* 10:2662-2671 (1994).
Jou et al., "Deletion Detection in the Dystrophin Gene by Multiplex Gap Ligase Chain Reaction and Immunochromatographic Strip Technology," *Human Mutation* 5:86-93 (1995).
Khanna et al., "Multliplex PCR/LDR for Detection of K-*ras* Mutations in Primary Colon Tumors," *Oncogene* 18:27-38 (1999).
Khrapko et al., "A Method for DNA Sequencing by Hybridization with Oligonucleotide Matrix," *J. DNA Seq. Map* 1:375-388 (1991).

Kim et al., "Polymeric Self-Assembled Monolayers. 2. Synthesis and Characterizaiton of Self-Assembled Polydiacetylene Mono- and Multilayers," *J. Am. Chem. Soc.* 117:3963-3967 (1995).

Koide et al., "Unstable Expansion of CAG Repeat in Hereditary Dentatorubral-Pallidoluysian Atrophy (DRPLA)," *Nat. Genet.* 6:9-13 (1994).

Kozal et al., "Extensive Polymorphisms Observed in HIV-1 Clade B Protease Gene Using High-Density Oligonucleotide Arrays," *Nature Medicine* 2:753-759 (1996).

Kremer et al., "Mapping of DNA Instability at the Fragile X to a Trinucleotide Repeat Sequence p(CCG)n," *Science* 22:1711-1714 (1991).

Kuznetsova et al., "DNA Sequencing by Hybridization with Oligonucleotides Immobilized in a Gel," *Mol. Biol.* (Mosk) (Russia) 28(2):290-299 (1994) (English abstract attached).

Landegren et al., "A Ligase-Mediated Gene Detection Technique," *Science* 241:1077-1080 (1988).

Lauer et al., "Cloning, Nucleotide Sequence, and Engineered Expression of *Thermus thermophilus* DNA Ligase, a Homolog of *Escherichia coli* DNA Ligase," *Journal of Bacteriology* 173(16):5047-5053 (1991).

Leach et al., "Mutations of a *mutS* Homolog in Hereditary Nonpolyposis Colorectal Cancer," *Cell* 75:1215-1225 (1993).

Lipshutz et al., "Using Oligonucleotide Probe Arrays To Assess Genetic Diversity," *Biotechniques* 19:442-447 (1995).

Livak et al., "Detection of Single Base Differences Using Biotinylated Nucleotides With Very Long Linker Arms," *Nuclear Acids Research* 20:4831-4837 (1989).

Livshits et al., "Dissociation of Duplexes Formed by Hybridization of DNA with Gel-Immobilized Oligonucleotides," *Journal of Biomolecular Structure & Dynamics* 11(4):783-795 (1994).

Lysov et al., "DNA Sequencing by Hybridization to Oligonucleotide Matrix. Calculation of Continuous Stacking Hybridization Efficiency," *Journal of Biomolecular Structure & Dynamics* 11(4):797-812 (1994).

Lysov et al., "Measurement of Distances Between DNA Segments Increases Efficiency of Sequencing by Hybridization with Oligonucleotide Matrix," *Molecular Biology* 28(3):433-436 (1994).

Mao et al., "Microsatellite Alterations As Clonal Markers for the Detection of Human Cancer," *Proc. Natl. Acad. Sci. USA* 91:9871-9875 (1994).

Mao et al., "Molecular Detection of Primary Bladder Cancer by Microsatellite Analysis," *Science* 271:659-662 (1996).

Maskos et al., "A Study of Oligonucleotide Reassociation Using Large Arrays of Oligonucleotides Synthesized on a Glass Support," *Nucleic Acids Research* 21:4663-4669 (1993).

Maskos et al., "A Novel Method for the Analysis of Multiple Sequence Variants by Hybridization to Oligonucleotides," *Nucleic Acids Research*, 21:2267-2268 (1993).

Merlo et al., "Frequent Microsatellite Instability in Primary Small Cell Lung Cancer," *Cancer Res.* 54:2098-2101 (1994).

Milner et al., "Selecting Effective Antisense Reagents on Combinatorial Oligonucleotide Arrays," *Nature Biotechnology* 15:537-541 (1997).

Munkholm et al., "Polymer Modification of Fiber Optic Chemical Sensors as a Method of Enhancing Fluorescence Signal for pH Measurement," *Anal. Chem.* 58:1427-1430 (1986).

Nawroz et al., "Allelotype of Head and Neck Squamous Cell Carcinoma," *Cancer Res.* 54:1152-1155 (1994).

Newton et al., "The Production of PCR Products with 5' Single-Stranded Tails Using Primers That Incorporate Novel Phosphoram Phosphoramidite Intermediates," *Nucleic Acids Research* 21(5):1155-1162 (1993).

Nickerson et al., "Automated DNA Diagnostics Using an ELIDA-Based Oligonucleotide Ligation Assay," *Proc. Natl. Acad. Sci. USA* 87:8923-8927 (1990).

Nikiforov et al., "Genetic Bit Analysis: A Solid Phase Method for Typing Single Nucleotide Polymorphisms," *Nucleic Acids Research* 22(20):4167-4175 (1994).

Nilsson et al., "Padlock Probes: Circularizing Oligonucleotides for Localized DNA Detection," *Science* 265:2085-2088 (1994).

Orr et al., "Expansion of an Unstable Trinucleotide CAG Repeat in Spinocerebeller Ataxia Type 1," *Nat. Genet.* 4:221-226 (1993).

Papadopoulos et al., "Mutation of a *mutl.* Homolog in Hereditary Colon Cancer," *Science* 263:1625-1629 (1994).

Parinov et al., "DNA Sequencing by Hybridization to Microchip Octa- and Decanuleotides Extended by Stacked Pentanucleotides," *Nucleic Acids Research* 24:2998-3004 (1996).

Park et al., "Detection of HCV RNA Using Ligation-Dependent Polymerase Chain Reaction in Formalin-Fixed, Paraffin-Embedded Liver Tissue," *Am. J. Pathology* 149(5):1485-1491 (1996).

Pease et al., "Light-Generated Oligonucleotide Arrays for Rapid DNA Sequence Analysis," *Proc. Natl. Acad. Sci. USA* 91:5022-5026 (1994).

Peinado et al., "Isolation and Characterization of Allelic Losses and Gains in Colorectal Tumors by Arbitrarily Primed Polymerase Chain Reaction," *Proc. Natl. Acad. Sci. USA* 89:10065-10069 (1992).

Peltomäki et al., "Microsatellite Instability is Associated with Tumors That Characterize the Hereditary Non-Polyposis Colorectal Carcinoma Syndrome," *Cancer Res.* 53:5853-5855 (1993).

Radford et al., "Allelotyping of Ductal Carcinoma in Situ of the Breast: Deletion of Loci on 8p, 13q, 16q, 17p and 171," *Cancer Res.* 55:3399-3406 (1995).

Reed et al., "Chromosome-Specific Microsatellite Sets For Fluorescence-Based, Semi-Automated Genome Mapping," *Nature Genetics* 7:390-395 (1994).

Reynolds et al., "Analysis of Genetic Markers in Forensic DNA Samples Using the Polymerase Chain Reaction," *Anal. Chem.* 63:2-15 (1991).

Risinger et al., "Genetic Instability of Microsatellites in Endometrial Carcinoma," *Cancer Res.* 53:5100-5103 (1993).

Ruppert et al., "Evidence for Two Bladder Cancer Suppressor Loci on Human Chromosome 9," *Cancer Res.* 53:5093-5095 (1993).

Saiki et al., "Enzymatic Amplification of β-Globin Genomic Sequences and Restriction Site Analysis for Diagnosis of Sickle Cell Anemia," *Science* 230:1350-1354 (1985).

Sambrook et al., *Molecular Cloning A Laboratory Manual*, 2nd Ed., Cold Spring Laboratory Press (1989).

Schena et al., "Parallel Human Genome Analysis: Microarray-Based Expression Monitoring of 1000 Genes," *Proc. Natl. Acad. Sci. USA* 93:10614-10619 (1996).

Schena et al., "Quantitative Monitoring of Gene Expression Patterns with a Complementary DNA Microarray," *Science* 270:467-470 (1995).

Shalon et al., "A DNA Microarray System for Analyzing Complex DNA Samples Using Two-Color Fluorescent Probe Hybridization," *Genome Research* 6:639-645 (1996).

Southern et al., Analyzing and Comparing Nucleic Acid Sequences by Hybridization to Arrays of Oligonucleotides: Evaluation Using Experimental Models,: *Genomics* 13:1008-1017 (1992).

Southern, E.M., "DNA Chips: Analyzing Sequence by Hybridization to Oligonucleotides on a Large Scale," *Trends in Genet.* 12(3):110-115 (1996).

Syvänen et al., "Identification of Individuals by Analysis of Biallelic DNA Markers, Using PCR and Solid-Phase Minisequencing," *Am. J. Hum. Genet.* 52:46-59 (1993).

Telenti et al., "Competitive Polymerase Chain Reaction Using an Internal Standard: Application to the Quantitation of Viral DNA," *Journal of Virological Methods* 39:259-268 (1992).

The Huntington's Disease Collaborative Research Group, "A Novel Gene Containing a Trinucleotide Repeat That is Expanded and Unstable on Huntington's Disease Chromosomes," *Cell* 72:971-983 (1993).

Thibodeau et al., "Microsatellite Instability in Cancer of the Proximal Colon," *Science* 260:816-819 (1993).

Timofeev et al., "Regioselective Immobilization of Short Oligonucleotides to Acrylic Copolymer Gels," *Nucleic Acids Research* 24:3142-3148 (1996).

Yershov et al., "DNA Analysis and Diagnostics on Oligonucleotide Microchips," *Proc. Natl. Acad. Sci. USA* 93:4913-4918 (1996).

Zebala et al., "Characterization of Steady State, Single-Turnover, and Binding Kinetics of the *Taq*I Restriction Endonuclease," *J. Biol Chem.* 267(12):8097-8105 (1992).

Zebala et al., "Implications for the Ligase Chain Reaction in Gastroenterology," *J. Clin. Gastroenterol.* 17(2):171-175 (1993).

Zhang et al., "Single-base Mutational Analysis of Cancer and Genetic Diseases Using Membrane Bound Modified Oligonucleotides," *Nucleic Acids Research*, 19:3929-3933 (1991).

Zirvi et al., "Improved Fidelity of Thermostable Ligases for Detection of Microsatellite Repeat Sequences Using Nucleoside Analogs," *Nucleic Acids Res.* 27(24):e41 (1999).

Zirvi et al., "Ligase-Based Detection of Mononucleotide Repeat Sequences," *Nucleic Acids Res.* 27(24):e40 (1999).

"Acrylamide" *Wikipedia Encyclopedia*, Retrieved from the internet at http://en.wikipedia.org/wiki/Acrylamide on Sep. 15, 2005.

Strategene Catalog, Published by Stratagene Cloning Systems, 11011 North Torrey Pines Road, La Jolla, California, 92037, pp. 132 (1994).

BIOCOMPARE, "Acrylamide Polymerization—A Practical Approach," at http://www.biocompare.com/technicalarticle/1089/Acrylamide-Polymerization-â□□-A-Practical-Approach-from-Bio-Rad.html, (2000).

Rehman et al., "Immobilization of Acrylamide-Modified Oligonucleotides by Co-Polymerization," *Nucleic Acids Res.* 27(2):649-655 (1999).

Tong et al., "Biochemical Properties of High Fidelity DNA Ligase from Thermus species AK16D," *Nucleic Acids Research* 27(3):788-794 (1999).

Tsui, L-P., "Mutations and Sequence Variations Detected in the Cystic Fibrosis Transmembrane Conductance Regulator (CFTR) Gene: a Report from the Cystic Fibrosis Genetic Analysis Consortium," *Human Mutation* 1:197-203 (1992).

Urdea, M.S., "Synthesis and Characterization of Branched DNA (bDNA) for the Direct and Quantitative Detection of CMV, HBC, HCV, and HIV," *Clincal Chemistry* 39(4):725-726 (1993).

Van Der Riet et al., "Frequent Loss of Chromosome 9p21-22 Early in Head and Neck Cancer Progression," *Cancer Res.* 54:1156-1158 (1994).

Van Ness et al., "A Versatile Solid Support System for Oligodeoxynucleotide Probe-based Hybridization Assays," *Nucleic Acids Research* 19:3345-3350 (1991).

Wang et al., "Large-Scale Identification, Mapping, and Genotyping of Single-Nucleotide Polymorphisms in the Human Genome," *Science* 280:1077-1082 (1998).

Weber et al., "Abundant Class of Human DNA Polymorphisms Which Can Be Typed Using the Polymerase Chain Reaction," *Amer. J. Hum. Genet.* 44:388-396 (1989).

Weissenbach et al., "A Second-Generation Linkage Map of the Human Genome," Nature 359:794-801 (1992).

Wiedman et al., "Ligase Chain Reaction (LCR)—Overview and Applications," *PCR Methods & Appl.* 3:551-564 (1994).

Winn-Deen et al., "Sensitive Fluorescence Method for Detecting DNA Ligation Amplification Products," *Clinical Chemistry* 37(9):1522-1523 (1991).

Wu et al., "The Ligation Amplification Reaction (LAR)-Amplification of Specific DNA Sequences Using Sequential Rounds of Template-Dependent Ligation," *Genomics* 4:560-569 (1989).

\* cited by examiner

PCR/ PCR/ LDR : Nearby alleles

1. PCR amplify regions containing allelic variations using gene-specific/zip code primers, dNTPs and *Taq* polymerase. ◆

2. PCR amplify all primary products using zip code primers, dNTPs and *Taq* polymerase.

3. Perform LDR using allele-specific LDR primers and thermostable ligase. Allele-specific oligonucleotides ligate to common oligonucleotides only when there is perfect complementarity at the junction.

4. Separate fluorescent products on a DNA sequencer and quantify each allele.

1st Position.
Heterozygous: A and C alleles.
2nd Position.
Heterozygous: G,C and T alleles.

1st Position.
Heterozygous: G and C alleles.
2nd Position.
Heterozygous: A and T alleles.

*FIG. 6*

PCR/PCR/LDR: Adjacent alleles, cancer detection

1. PCR amplify regions containing allelic variations using gene-specific/zip code primers, dNTPs and Taq polymerase. ◆

2. PCR amplify all primary products using zip code primers, dNTPs and Taq polymerase.

3. Perform LDR using allele-specific LDR primers and thermostable ligase. Allele-specific oligonucleotides ligate to common oligonucleotides only when there is perfect complementarity at the junction.

4. Separate fluorescent products on a DNA sequencer and quantify each allele.

F1 — $A_{n+2}$
Gly to Asp mutation

F2 — $A_{n+4}$
Gln to Glu mutation

FIG. 7

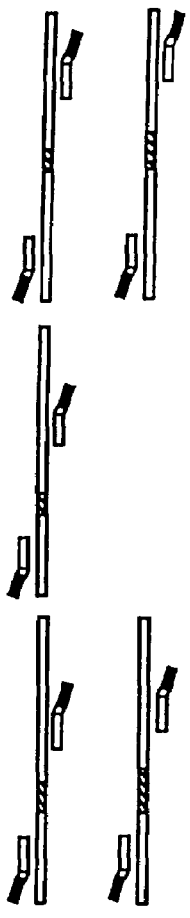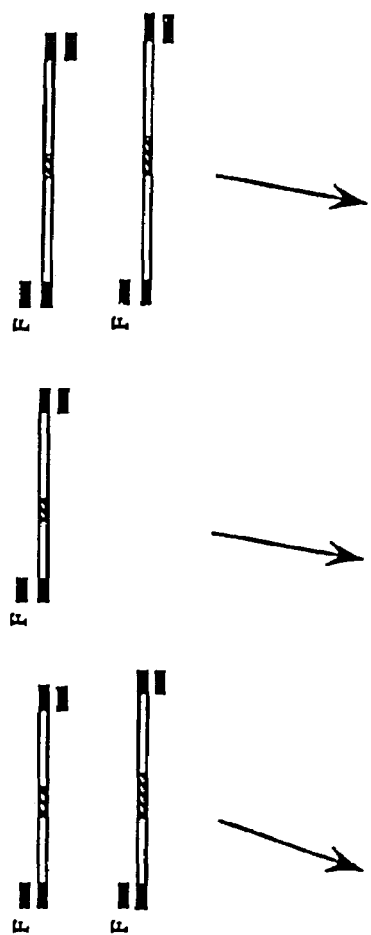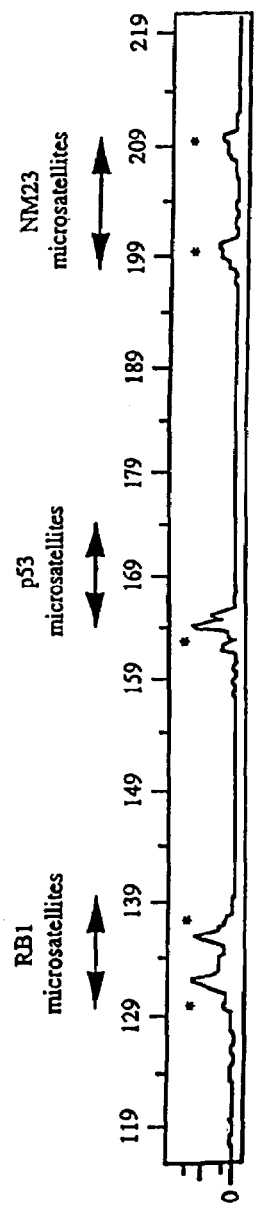
FIG. 23

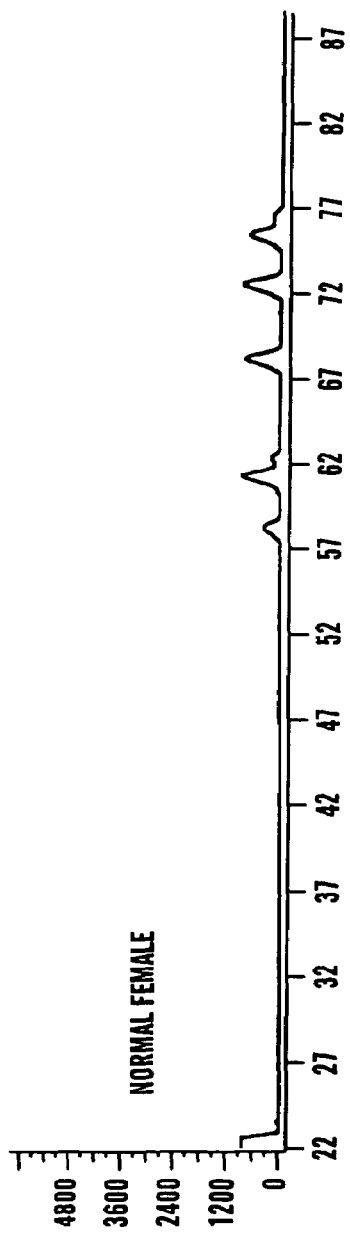
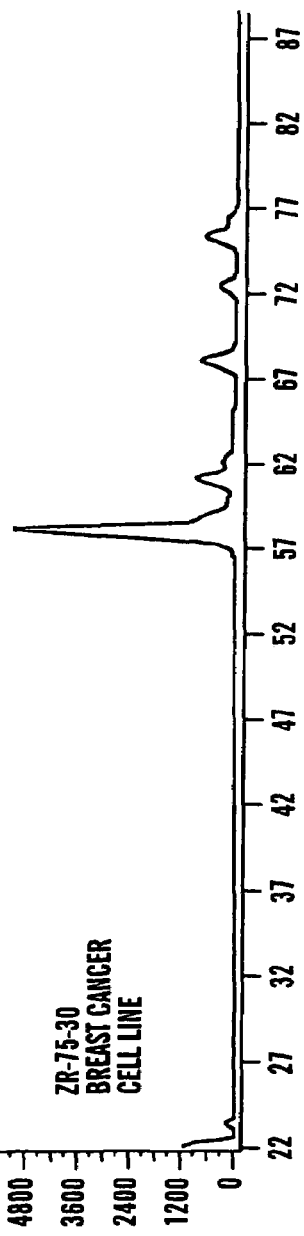
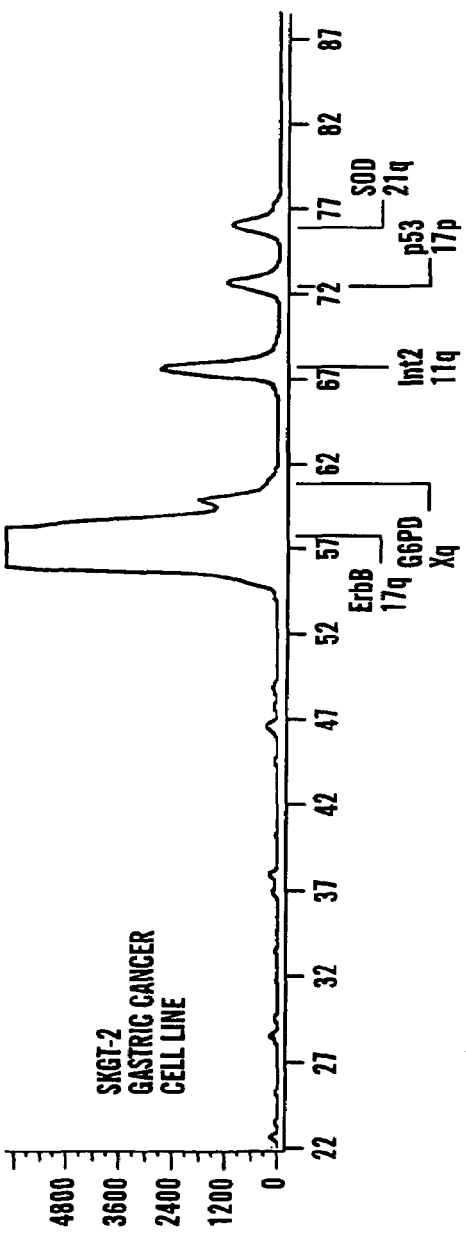
FIG. 26A
FIG. 26B
FIG. 26C

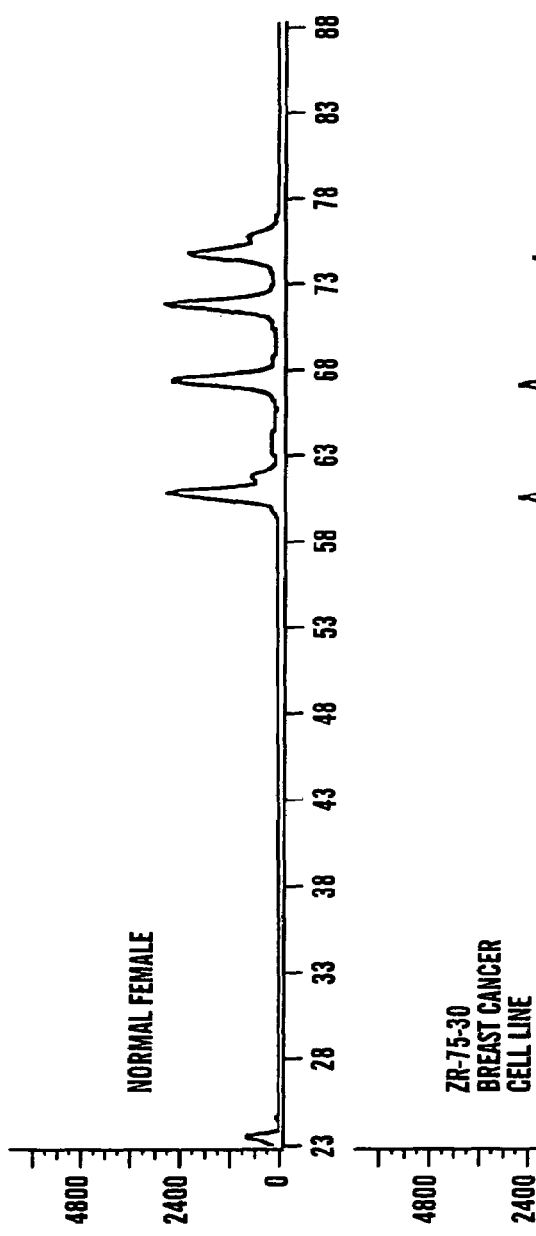
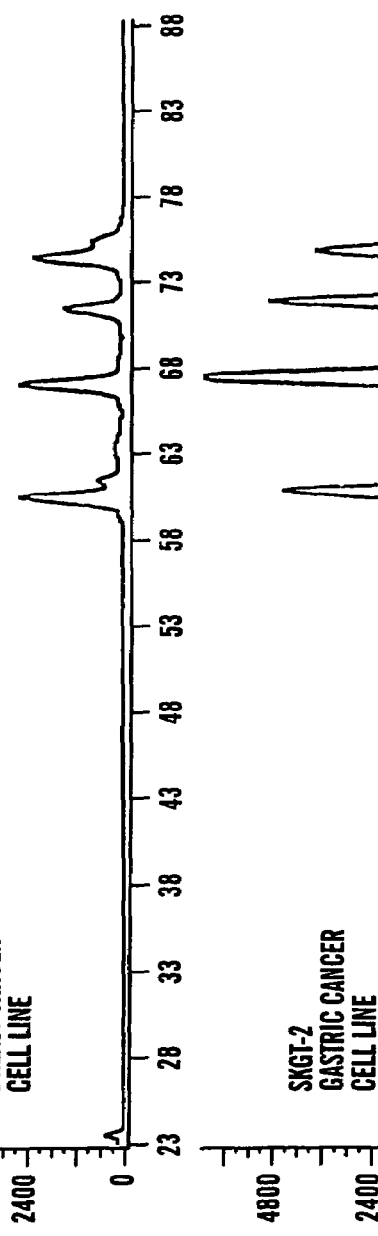
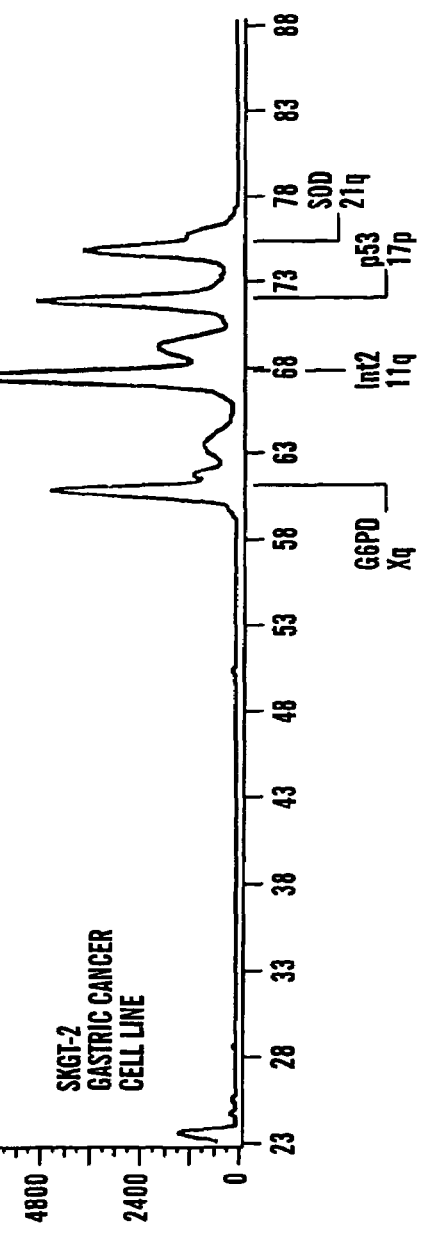
FIG. 27A
FIG. 27B
FIG. 27C

SEQUENCE LISTING

<160> NUMBER OF SEQ ID NOS: 76

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Probe
      Sequence

<400> SEQUENCE: 1
cacgctatcc cgttagacat tgtcaagcag gcgatgttgt cccggttc                48

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Probe
      Sequence

<400> SEQUENCE: 2
cagatggggc cgaagatcct gttattgata catagtgcgg tagttggc                 48

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: Probe
      Sequence

<400> SEQUENCE: 3
cacgctatcc cgttagacat cgccctgatg gggagaatgt gaaaattc                 48

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Probe
      Sequence

<400> SEQUENCE: 4
cagtggccat caaagtgttg agggagcgta catagtgcgg tagttggc                 48

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Probe
      Sequence

<400> SEQUENCE: 5
cacgctatcc cgttagacat tcataaccct tgccgttcac agacacgtac              50

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Probe
      Sequence

<400> SEQUENCE: 6
cacagtctct cggcgctggg caataataca tagtgcggta gttggc         46

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Probe
      Sequence

<400> SEQUENCE: 7
cacgctatcc cgttagacat cttagtaatt gaggtgcgtg tttgtgcctg tc         52

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Probe
      Sequence

<400> SEQUENCE: 8
ctgggagaga ccggcgcaca ttactacata gtgcggtagt tggc         44

<210> SEQ ID NO 9
<211> LENGTH: 49
<212> TYPE: DNA
<213> ORGANISM: Artificial Sequence
<220> FEATURE:
<223> OTHER INFORMATION: Description of Artificial Sequence: Probe
      Sequence

<400> SEQUENCE: 9
cacgctatcc cgttagacat ctgtaccagt gcaggtcctc actttaatc         49

<210> SEQ ID NO 10
<211> LENGTH: 47
<212> TYPE: DNA
<213> ORGANISM: Artificial Sequence
<220> FEATURE:
<223> OTHER INFORMATION: Description of Artificial Sequence: Probe
      Sequence

<400> SEQUENCE: 10
ctctatccag aaaacacggt gggccgctac atagtgcggt agttggc         47

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
ggagcacgct atcccgttag ac         22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 12
cgctgccaac taccgcacta tg         22

```
<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 13
agcttcaatg atgagaacct gc                                         22

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 14
gcatagtggt ggctgacctg ttcatat                                    27

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 15
agcttcaatg atgagaacct gt                                         22

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 16
ctccatgggc ccagcc                                                16

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 17
agcactggtg ccctgtgag                                             19

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 18
ctccatgggc ccagct                                                16
```

```
<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 19
ggggacagcc atgcactga                                              19

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 20
gcctctggta gcctttcaac cata                                        24

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 21
ggggacagcc atgcactgc                                              19

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 22
ttagaaatca tcaagcctag gtcat                                       25

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 23
caccttttag cttcctgagc aatgat                                      26

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 24
ttagaaatca tcaagcctag gtcag                                       25

<210> SEQ ID NO 25
```

```
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 25
ggttgtattt gtcaccatat taatta                                  26

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 26
atttttctct attgttttca tctttcagga                              30

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 27
atggttgtat ttgtcaccat attaattg                                28

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 28
gggccaagaa ggtatctacc a                                       21

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 29
atagtgtcta ttaggcattt gaaaatgtgt at                           32

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 30
gggccaagaa ggtatctacc g                                       21

<210> SEQ ID NO 31
<211> LENGTH: 22
```

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 31
acacagcagc ttactccaga gg                                                22

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 32
tcaagtccaa ggccattggc ttata                                             25

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 33
acacagcagc ttactccaga ga                                                22

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 34
ccagcaaaga gaaagaagg g                                                  21

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 35
ccccagaaat cacaggtggg ctat                                              24

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 36
ccagcaaaga gaaagaagg a                                                  21

<210> SEQ ID NO 37
<211> LENGTH: 26
<212> TYPE: DNA

<213> ORGANISM: Artificial Sequence
<220> FEATURE:
<223> OTHER INFORMATION: Description of Artificial Sequence:
      Oligonucleotide Sequence

<400> SEQUENCE: 37
atgatattag agctcactca tgtcca                                        26

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 38
tcagtttgga aaaagacaaa gaattcttt                                     29

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 39
atgatattag agctcactca tgtccg                                        26

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 40
tgctgtcttc caggaatctg tt                                            22

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 41
caactctctc gaagccatgt tcacaa                                        26

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 42
attgctgtct tccaggaatc tgtg                                          24

<210> SEQ ID NO 43
<211> LENGTH: 22
<212> TYPE: DNA
<213> ORGANISM: Artificial Sequence

```
<220> FEATURE:
<223> OTHER INFORMATION: Description of Artificial Sequence:
      Oligonucleotide Sequence

<400> SEQUENCE: 43
ggacatagtg accgtgcagg tc                                              22

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 44
cttccccagt gtgagtgccg ta                                              22

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 45
atggacatag tgaccgtgca ggtt                                            24

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 46
ctatgacacc gtcatcagca gg                                              22

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 47
gacatccagg cccccgac                                                   18

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide Sequence

<400> SEQUENCE: 48
tactatgaca ccgtcatcag caga                                            24

<210> SEQ ID NO 49
<211> LENGTH: 43
<212> TYPE: DNA
<213> ORGANISM: Artificial Sequence
<220> FEATURE:
```

```
<223> OTHER INFORMATION: Description of Artificial Sequence:  Primer
      Sequence

<400> SEQUENCE: 49
ggagcacgct atcccgttag acagccaagg ggaaccctga gag                 43

<210> SEQ ID NO 50
<211> LENGTH: 46
<212> TYPE: DNA
<213> ORGANISM: Artificial Sequence
<220> FEATURE:
<223> OTHER INFORMATION: Description of Artificial Sequence:  Primer
      Sequence

<400> SEQUENCE: 50
cgctgccaac taccgcacta tgatcgtggt cgaggtggtc accatc              46

<210> SEQ ID NO 51
<211> LENGTH: 52
<212> TYPE: DNA
<213> ORGANISM: Artificial Sequence
<220> FEATURE:
<223> OTHER INFORMATION: Description of Artificial Sequence:  Primer
      Sequence

<400> SEQUENCE: 51
cctcgttgcg aggcgtattc tgtatttcct cttctgtaaa agggaagttt gt       52

<210> SEQ ID NO 52
<211> LENGTH: 47
<212> TYPE: DNA
<213> ORGANISM: Artificial Sequence
<220> FEATURE:
<223> OTHER INFORMATION: Description of Artificial Sequence:  Primer
      Sequence

<400> SEQUENCE: 52
gcgacctgac ttgccgaaga acatgtccca tctcctctac ctgatac             47

<210> SEQ ID NO 53
<211> LENGTH: 48
<212> TYPE: DNA
<213> ORGANISM: Artificial Sequence
<220> FEATURE:
<223> OTHER INFORMATION: Description of Artificial Sequence:  Primer
      Sequence

<400> SEQUENCE: 53
ggagcacgct atcccgttag actaaagatc tgtcttgcgt cccagtca            48

<210> SEQ ID NO 54
<211> LENGTH: 51
<212> TYPE: DNA
<213> ORGANISM: Artificial Sequence
<220> FEATURE:
<223> OTHER INFORMATION: Description of Artificial Sequence:  Primer
      Sequence

<400> SEQUENCE: 54
cgctgccaac taccgcacta tgtatcaatt ttgcagagct tagatggaat g        51

<210> SEQ ID NO 55
<211> LENGTH: 51
<212> TYPE: DNA
<213> ORGANISM: Artificial Sequence
<220> FEATURE:
<223> OTHER INFORMATION: Description of Artificial Sequence:  Primer
```

Sequence

<400> SEQUENCE: 55
cctcgttgcg aggcgtattc tgtagcactt gtgatcatgg ttttagaaat c      51

<210> SEQ ID NO 56
<211> LENGTH: 51
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 56
gcgacctgac ttgccgaaga actatcgtat ttgatgatcc tcataaagtt g      51

<210> SEQ ID NO 57
<211> LENGTH: 46
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 57
ggagcacgct atcccgttag acatcagcca cttggaagga gcaaac      46

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 58
cgctgccaac taccgcacta tgatggacca tggctgagtc tcctttag      48

<210> SEQ ID NO 59
<211> LENGTH: 48
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 59
cctcgttgcg aggcgtattc tgaaccaaca cggagaagca ttgttttc      48

<210> SEQ ID NO 60
<211> LENGTH: 53
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 60
gcgacctgac ttgccgaaga actattagcc tcaatcctca tactgacctc tac      53

<210> SEQ ID NO 61
<211> LENGTH: 57
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 61
ggagcacgct atcccgttag acatctccta acatctatgt actggattat ctaaatg        57

<210> SEQ ID NO 62
<211> LENGTH: 53
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 62
cgctgccaac taccgcacta tgatcttact caagtaatca ctcaccagtg ttg            53

<210> SEQ ID NO 63
<211> LENGTH: 47
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 63
cctcgttgcg aggcgtattc tgaatgagtc aaattggcct ggacttg                   47

<210> SEQ ID NO 64
<211> LENGTH: 46
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 64
gcgacctgac ttgccgaaga acttaattcc cgtgagaagg gagatg                    46

<210> SEQ ID NO 65
<211> LENGTH: 50
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 65
cctcgttgcg aggcgtattc tgaaggatct ggatgaagcc atttctaaac                50

<210> SEQ ID NO 66
<211> LENGTH: 54
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 66
gcgacctgac ttgccgaaga acttggaaaa ggtattataa gcagagaaaa gatg           54

<210> SEQ ID NO 67
<211> LENGTH: 44
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 67
ggagcacgct atcccgttag acaggaccgc aaaaggcttt catc                44

<210> SEQ ID NO 68
<211> LENGTH: 47
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 68
cgctgccaac taccgcacta tgtagcaccc aggctgtacc caattag             47

<210> SEQ ID NO 69
<211> LENGTH: 41
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 69
cctcgttgcg aggcgtattc tgatcgggcg ctgggcttca c                   41

<210> SEQ ID NO 70
<211> LENGTH: 45
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 70
gcgacctgac ttgccgaaga acatcagatg ccgcactcca agaag               45

<210> SEQ ID NO 71
<211> LENGTH: 45
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 71
ggagcacgct atcccgttag acataagagc ccacggcgtc tcttc               45

<210> SEQ ID NO 72
<211> LENGTH: 48
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 72
cgctgccaac taccgcacta tgtaagagac agtgcccagg acagagtc            48

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 73

```
ggagcacgct atcccgttag ac                                              22

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 74
cgctgccaac taccgcacat g                                               21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 75
cctcgtgcga ggcgtattct g                                               21

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Primer
      Sequence

<400> SEQUENCE: 76
gcgacctgac ttgccgaaga ac                                              22
```

DETECTION OF NUCLEIC ACID SEQUENCE DIFFERENCES USING COUPLED LIGASE DETECTION AND POLYMERASE CHAIN REACTIONS

This application is a continuation of U.S. patent application Ser. No. 11/229,366, filed Sep. 16, 2005, which is a continuation of U.S. patent application Ser. No. 10/843,720, filed May 12, 2004, now U.S. Pat. No. 7,166,434, which is a continuation of U.S. patent application Ser. No. 09/918,156, filed Jul. 30, 2001, now U.S. Pat. No. 6,797,470 issued Sep. 28, 2004, which is a continuation of U.S. patent application Ser. No. 09/440,523, filed Nov. 15, 1999, now U.S. Pat. No. 6,268,148, issued Jul. 31, 2001, which is a divisional of U.S. patent application Ser. No. 08/864,473, filed May 28, 1997, now U.S. Pat. No. 6,027,889 issued Feb. 22, 2000, and claims the benefit of U.S. Provisional Patent Application Ser. No. 60/018,532, filed May 29, 1996, which are all hereby incorporated by reference in their entirety.

This invention was developed with government funding under National Institutes of Health Grant No. GM41337-06. The U.S. Government may retain certain rights.

FIELD OF THE INVENTION

The present invention relates to the detection of nucleic acid sequence differences using coupled ligase detection reaction ("LDR") and polymerase chain reaction ("PCR"). One aspect of the present invention involves use of a ligase detection reaction coupled to a polymerase chain reaction. Another aspect of the present invention relates to the use of a primary polymerase chain reaction coupled to a secondary polymerase chain reaction coupled to a ligase detection reaction. A third aspect of the present invention involves a primary polymerase chain reaction coupled to a secondary polymerase chain reaction.

BACKGROUND OF THE INVENTION

Multiplex Detection

Large-scale multiplex analysis of highly polymorphic loci is needed for practical identification of individuals, e.g., for paternity testing and in forensic science (Reynolds et al., Anal. Chem., 63:2-15 (1991)), for organ-transplant donor-recipient matching (Buyse et al., Tissue Antigens, 41:1-14 (1993) and Gyllensten et al., PCR Meth. Appl, 1:91-98 (1991)), for genetic disease diagnosis, prognosis, and pre-natal counseling (Chamberlain et al., Nucleic Acids Res., 16:11141-11156 (1988) and L. C. Tsui, Human Mutat., 1:197-203 (1992)), and the study of oncogenic mutations (Hollstein et al., Science, 253:49-53 (1991)). In addition, the cost-effectiveness of infectious disease diagnosis by nucleic acid analysis varies directly with the multiplex scale in panel testing. Many of these applications depend on the discrimination of single-base differences at a multiplicity of sometimes closely spaced loci.

A variety of DNA hybridization techniques are available for detecting the presence of one or more selected polynucleotide sequences in a sample containing a large number of sequence regions. In a simple method, which relies on fragment capture and labeling, a fragment containing a selected sequence is captured by hybridization to an immobilized probe. The captured fragment can be labeled by hybridization to a second probe which contains a detectable reporter moiety.

Another widely used method is Southern blotting. In this method, a mixture of DNA fragments in a sample is fractionated by gel electrophoresis, then fixed on a nitrocellulose filter. By reacting the filter with one or more labeled probes under hybridization conditions, the presence of bands containing the probe sequences can be identified. The method is especially useful for identifying fragments in a restriction-enzyme DNA digest which contains a given probe sequence and for analyzing restriction-fragment length polymorphisms ("RFLPs").

Another approach to detecting the presence of a given sequence or sequences in a polynucleotide sample involves selective amplification of the sequence(s) by polymerase chain reaction. U.S. Pat. No. 4,683,202 to Mullis, et al. and R. K. Saiki, et al., Science 230:1350 (1985). In this method, primers complementary to opposite end portions of the selected sequence(s) are used to promote, in conjunction with thermal cycling, successive rounds of primer-initiated replication. The amplified sequence(s) may be readily identified by a variety of techniques. This approach is particularly useful for detecting the presence of low-copy sequences in a polynucleotide-containing sample, e.g., for detecting pathogen sequences in a body-fluid sanple.

More recently, methods of identifying known target sequences by probe ligation methods have been reported. U.S. Pat. No. 4,883,750 to N. M. Whiteley, et al., D. Y. Wu, et al., Genomics 4:560 (1989), U. Landegren, et al., Science 241:1077 (1988), and E. Winn-Deen, et al., Clin. Chem. 37:1522 (1991). In one approach, known as oligonucleotide ligation assay ("OLA"), two probes or probe elements which span a target region of interest are hybridized to the target region. Where the probe elements basepair with adjacent target bases, the confronting ends of the probe elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, hybridization, and ligation in the presence of pairs of probe elements, the target sequence is amplified linearly, allowing very small amounts of target sequence to be detected and/or amplified. This approach is referred to as ligase detection reaction. When two complementary pairs of probe elements are utilized, the process is referred to as the ligase chain reaction which achieves exponential amplification of target sequences. F. Barany, "Genetic Disease Detection and DNA Amplification Using Cloned Thermostable Ligase," Proc. Nat'l Acad. Sci. USA, 88:189-93 (1991) and F. Barany, "The Ligase Chain Reaction (LCR) in a PCR World," PCR Methods and Applications, 1:5-16 (1991).

Another scheme for multiplex detection of nucleic acid sequence differences is disclosed in U.S. Pat. No. 5,470,705 to Grossman-et. al. where sequence-specific probes, having a detectable label and a distinctive ratio of charge/translational frictional drag, can be hybridized to a target and ligated together. This technique was used in Grossman, et. al., "High-density Multiplex Detection of Nucleic Acid Sequences: Oligonucleotide Ligation Assay and Sequence-coded Separation," Nucl. Acids Res. 22(21):4527-34 (1994) for the large scale multiplex analysis of the cystic fibrosis transmembrane regulator gene.

Jou, et. al., "Deletion Detection in Dystrophia Gene by Multiplex Gap Ligase Chain Reaction and Immunochromatographic Strip Technology," Human Mutation 5:86-93 (1995) relates to the use of a so called "gap ligase chain reaction" process to amplify simultaneously selected regions of multiple exons with the amplified products being read on an immunochromatographic strip having antibodies specific to the different haptens on the probes for each exon.

There is a growing need (e.g., in the field of genetic screening) for methods useful in detecting the presence or absence of each of a large number of sequences in a target polynucleotide. For example, as many as 400 different mutations have been associated with cystic fibrosis. In screening for genetic predisposition to this disease, it is optimal to test all of the possible different gene sequence mutations in the subject's genomic DNA, in order to make a positive identification of "cystic fibrosis". It would be ideal to test for the presence or absence of all of the possible mutation sites in a single assay. However, the prior-art methods described above are not readily adaptable for use in detecting multiple selected sequences in a convenient, automated single-assay format.

Solid-phase hybridization assays require multiple liquid-handling steps, and some incubation and wash temperatures must be carefully controlled to keep the stringency needed for single-nucleotide mismatch discrimination. Multiplexing of this approach has proven difficult as optimal hybridization conditions vary greatly among probe sequences.

Developing a multiplex PCR process that yields equivalent amounts of each PCR product can be difficult and laborious. This is due to variations in the annealing rates of the primers in the reaction as well as varying polymerase extension rates for each sequence at a given Mg2+ concentration. Typically, primer, Mg2+, and salt concentrations, along with annealing temperatures are adjusted in an effort to balance primer annealing rates and polymerase extension rates in the reaction. Unfortunately, as each new primer set is added to the reaction, the number of potential amplicons and primer dimers which could form increase exponentially. Thus, with each added primer set, it becomes increasingly more difficult and time consuming to work out conditions that yield relatively equal amounts of each of the correct products.

Allele-specific PCR products generally have the same size, and an assay result is scored by the presence or absence of the product band(s) in the gel lane associated with each reaction tube. Gibbs et al., *Nucleic Acids Res.*, 17:2437-2448 (1989). This approach requires splitting the test sample among multiple reaction tubes with different primer combinations, multiplying assay cost. PCR has also discriminated alleles by attaching different fluorescent dyes to competing allelic primers in a single reaction tube (F. F. Chehab, et al., *Proc. Natl. Acad. Sci. USA*, 86:9178-9182 (1989)), but this route to multiplex analysis is limited in scale by the relatively few dyes which can be spectrally resolved in an economical manner with existing instrumentation and dye chemistry. The incorporation of bases modified with bulky side chains can be used to differentiate allelic PCR products by their electrophoretic mobility, but this method is limited by the successful incorporation of these modified bases by polymerase, and by the ability of electrophoresis to resolve relatively large PCR products which differ in size by only one of these groups. Livak et al., *Nucleic Acids Res.*, 20:4831-4837 (1989). Each PCR product is used to look for only a single mutation, making multiplexing difficult.

Ligation of allele-specific probes generally has used solid-phase capture (U. Landegren et al., *Science*, 241:1077-1080 (1988); Nickerson et al., *Proc. Natl. Acad. Sci. USA*, 87:8923-8927 (1990)) or size-dependent separation (D. Y. Wu, et al., *Genomics*, 4:560-569 (1989) and F. Barany, *Proc. Natl. Acad. Sci.*, 88:189-193 (1991)) to resolve the allelic signals, the latter method being limited in multiplex scale by the narrow size range of ligation probes. Further, in a multiplex format, the ligase detection reaction alone cannot make enough product to detect and quantify small amounts of target sequences. The gap ligase chain reaction process requires an additional step—polymerase extension. The use of probes with distinctive ratios of charge/translational frictional drag for a more complex multiplex will either require longer electrophoresis times or the use of an alternate form of detection.

The need thus remains for a rapid single assay format to detect the presence or absence of multiple selected sequences in a polynucleotide sample.

Microsatellite Analysis

Tandem repeat DNA sequences known as microsatellites represent a very common and highly polymorphic class of genetic elements within the human genome. These microsatellite markers containing small repeat sequences have been used for primary gene mapping and linkage analysis. Weber, J. L. et al., *Am. J. Hum. Genet.* 44: 388-396 (1989); Weissenbach, J. et al., *Nature (London)* 359: 794-800 (1992). PCR amplification of these repeats allows rapid assessment for loss of heterozygosity and can greatly simplify procedures for mapping tumor suppressor genes. Ruppert, J. M., et al., *Cancer Res.* 53: 5093-94 (1993); van der Riet, et al., *Cancer Res.* 54: 1156-58 (1994); Nawroz, H., et al., *Cancer Res.* 54: 1152-55 (1994); Cairns, P., et al., *Cancer Res.* 54: 1422-24 (1994). More recently, they have been used to identify specific mutations in certain inherited disorders including Huntington disease, fragile X syndrome, myotonic dystrophy, spinocerebellar ataxia type I, spinobulbar muscular atrophy, and hereditary dentatorubral-pallidoluysian atrophy. The Huntington's Disease Collaborative Research Group Cell 72: 971-83 (1993); Kremer, E. J., et al., *Science* 252: 1711-14 (1991); Imbert, G., et al., *Nat. Genet.* 4: 72-76 (1993); Orr, H. T., et al., *Nat. Genet.* 4: 221-226 (1993); Biancalana, V., et al., *Hum. Mol Genet.* 1: 255-258 (1992); Chung, M.-Y., et al., *Nat. Genet.* 5: 254-258 (1993); Koide, R., et al., *Nat. Genet.* 6: 9-13 (1994). These inherited disorders appear to arise from the expansion of trinucleotide repeat units within susceptible genes. A more widespread microsatellite instability, demonstrated by expansion or deletion of repeat elements in neoplastic tissues, was first reported in colorectal tumors. Peinado, M. A., et al. *Proc. Natl. Acad. Sci. USA* 89: 10065-69 (1992); Ionov, Y., *Nature (London)* 363: 558-61 (1993); Thibodeau, S. N., et al., *Science* 260: 816-819 (1993) and later in several other tumor types (Risinger, J. I., *Cancer Res.* 53: 5100-03 (1993); Han, H.-J., et al., *Cancer Res.* 53: 5087-89 (1993); Peltomäki, P., *Cancer Res.* 53: 5853-55 (1993); Gonzalez-Zulueta, M., et al., *Cancer Res.* 53: 5620-23 (1993); Merlo, A., et al., *Cancer Res.* 54: 2098-2101 (1994)). In hereditary nonpolyposis colorectal carcinoma patients, this genetic instability is apparently due to inherited and somatic mutations in mismatch repair genes. Leach, F., et al., *Cell* 75: 1215-1225 (1993); Fishel, R., et al., *Cell* 75: 1027-38 (1993); Papadopoulos, N., et al., *Science* 263: 1625-29 (1994); Bronner, C. E., et al., *Nature (London)* 368: 258-61 (1994).

PCR is commonly used for microsatellite analysis in identifying both the appearance of new polymorphisms and the loss of heterozygosity in cancer detection. L. Mao, et. al., "Microsatellite Alterations as Clonal Markers for the Detection of Human Cancer," *Proc. Nat'l Acad. Sci USA* 91(21): 9871-75 (1994); L. Mao, et. al., "Molecular Detection of Primary Bladder Cancer by Microsatellite Analysis," *Science* 271:659-62 (1996); D. Radford, et. al., "Allelotyping of Ductal Carcinoma in situ of the Breast: Detection of Loci on 8p, 13q, 16k, 17p and 17q," *Cancer Res.* 55(15): 3399-05

(1995). In using PCR for such purposes, each PCR reaction is run individually and separated on a sequencing gel.

Although these references demonstrate that PCR has application to diagnosis and prognosis of certain cancers, this type of analysis is deficient, because it does not permit a high throughput and requires size separation. In addition, there are problems with PCR slippage, causing researchers to shift to tri-, tetra-, and higher nucleotide repeat units, making cancer detection more difficult.

Microsatellite markers have also been used for colon cancer detection (L. Cawkwell, et. al., "Frequency of Allele Loss of DCC, p53, RB1, WT1, NF1, NM23, and APC/MCC in Colorectal Cancer Assayed by Fluorescent Multiplex Polymerase Chain Reaction," Br. J. Cancer 70(5): 813-18 (1994)) and for genome mapping (P. Reed, et. al., "Chromosome-specific Microsatellite Sets for Fluorescent-Based, Semi-Automated Genome Mapping," Nat. Genet. 7(3): 390-95 (1994)). However, the key to such multiplex processes is the ability to perform them in a single reaction tube. Conventional multiplex microsatellite marker approaches require careful attention to primer concentrations and amplification conditions. Although PCR products can be pooled in sets, this requires a prerun on agarose gels to insure that the mixture has about equal amounts of DNA in each band.

Human Identification

PCR has also been used for human identification, such as paternity testing, criminal investigations, and military personnel identification. A. Syvanen et. al., "Identification of Individuals by Analysis of Biallelic DNA Markers, Using PCR and Solid-Phase Mini-Sequencing" Am. J. Hum. Genet. 52(1): 46-59 (1993) describes a mini-sequencing approach to human identification. The technique requires PCR-amplification of individual markers with at most 4 PCR reactions being carried out at a time in a single PCR tube. Mini-sequencing is carried out to determine individual polymorphisms.

Coupled Processes

G. Deng, et. al., "An Improved Method of Competitive PCR for Quantitation of Gene Copy Number," Nucl. Acids Res. 21: 484849 (1993)-describes a competitive PCR process. Here, two PCR steps are utilized with different sets of primers being used for each gene and its equivalent standard.

T. Msuih, et. al., "Novel, Ligation-Dependent PCR Assay for Detection of Hepatitis C. Virus in Serum," J. Clin Microbio. 34: 501-07 (1996) and Y. Park, et. al., "Detection of HCV RNA Using Ligation-Dependent Polymerase Chain Reaction in Formalin-Fixed Paraffin-Embedded Liver Tissue" (submitted) describe the use of a LDR/PCR process in work with RNA.

SUMMARY OF THE INVENTION

The present invention is directed to the detection of nucleic acid sequence differences using coupled LDR and PCR processes. The present invention can be carried out in one of the following 3 embodiments: (1) LDR coupled to PCR; (2) primary PCR coupled to secondary PCR coupled to LDR; and (3) primary PCR coupled to secondary PCR. Each of these embodiments have particular applicability in detecting certain characteristics. However, each requires the use of coupled reactions for multiplex detection of nucleic acid sequence differences where oligonucleotides from an early phase of each process contain sequences which may be used by oligonucleotides from a later phase of the process.

I. Primary PCR/Secondary PCR/LDR Process

One aspect of the present invention relates to a method for identifying two or more of a plurality of sequences differing by one or more single-base changes, insertions, deletions, or translocations in a plurality of target nucleotide sequences. This method involves a first polymerase chain reaction phase, a second polymerase chain reaction phase, and a ligase detection reaction phase. This process involves analyzing a sample potentially containing one or more target nucleotide sequences with a plurality of sequence differences.

In the first polymerase chain reaction phase, one or more primary oligonucleotide primer groups are provided. Each group comprises one or more primary oligonucleotide primer sets with each set having a first nucleotide primer, having a target-specific portion and a 5' upstream secondary primer-specific portion, and a second oligonucleotide primer, having a target-specific portion and a 5' upstream secondary primer-specific portion. The first oligonucleotide primers of each set in the same group contain the same 5' upstream secondary primer-specific portion and the second oligonucleotide primers of each set in the same group contain the same 5' upstream primer-specific portion. The oligonucleotide primers in a particular set are suitable for hybridization on complementary strands of a corresponding target nucleotide sequence to permit formation of a polymerase chain reaction product. However, there is a mismatch which interferes with formation of such a polymerase chain reaction product when the primary oligonucleotide primers hybridize to any other nucleotide sequence in the sample. The polymerase chain reaction products in a particular set may be distinguished from other polymerase chain reaction products in the same group or groups. The primary oligonucleotide primers, the sample, and the polymerase are blended to form a primary polymerase chain reaction mixture.

The primary polymerase chain reaction mixture is subjected to two or more polymerase chain reaction cycles involving a denaturation treatment, a hybridization treatment, and an extension treatment, as substantially described above. During hybridization, target-specific portions of the primary oligonucleotide primers hybridize to the target nucleotide sequences. The extension treatment causes hybridized primary oligonucleotide primers to be extended to form primary extension products complementary to the target nucleotide sequence to which the primary oligonucleotide primers are hybridized.

Although the upstream secondary primer-specific portions of a primary oligonucleotide primer set are not present on the target DNA, their sequences are copied by the second and subsequent cycles of the primary polymerase-chain reaction phase. As a result, the primary extension products produced after the second cycle have the secondary primer-specific portions on their 5' ends and the complement of primer-specific portion on their 3' ends.

Next, there is a second polymerase chain reaction phase. This phase involves providing one or a plurality of secondary oligonucleotide primer sets. Each set has a first secondary oligonucleotide primer containing the same sequence as the 5' upstream portion of the first primary oligonucleotide primer, and a second secondary oligonucleotide primer containing the same sequence as the 5' upstream portion of the second primary oligonucleotide primer from the same primary oligonucleotide primer set as the first primary oligonucleotide complementary to the first secondary primer. A set of secondary oligonucleotide primers may be used to amplify all of the primary extension products in a given group. The secondary oligonucleotide primers are blended with the primary extension products and the polymerase to form a secondary polymerase chain reaction mixture.

The secondary polymerase chain reaction mixture is subjected to one or more polymerase chain reaction cycles having a denaturation treatment, a hybridization treatment, and an extension treatment, as substantially set forth above. During the hybridization treatment, the secondary oligonucleotide primers hybridize to the complementary sequences present on the primary extension products but not to the original target sequence. The extension treatment causes the hybridized secondary oligonucleotide primers to be extended to form secondary extension products complementary to the primary extension-products.

The last phase of this aspect of the present invention involves a ligase detection reaction process. Here, a plurality of oligonucleotide probe sets are provided where each set has a first oligonucleotide probe, having a secondary extension product-specific portion and a detectable reporter label, and a second oligonucleotide probe, having a secondary extension product-specific portion. The oligonucleotide probes in a particular set are suitable for ligation together when hybridized adjacent to one another on a complementary secondary extension product-specific portion. However, there is a mismatch which interferes with such ligation when the oligonucleotide probes are hybridized to any other nucleotide sequence present in the sample. The ligation product of oligonucleotide probes in a particular set may be distinguished from either probe or other ligation products. The plurality of oligonucleotide probe sets, the secondary extension products, and a ligase are blended to form a ligase detection reaction mixture.

The ligase detection reaction mixture is subjected to one or more ligase detection reaction cycles having a denaturation treatment and hybridization treatment substantially as described above. In the hybridization treatment, the oligonucleotide probe sets hybridize at adjacent positions in a base-specific manner to the respective secondary extension products if present. As a result, adjacent probes ligate to one another to form a ligation product sequence containing the detectable reporter label and the secondary extension product-specific portions connected together. The oligonucleotide probe sets may hybridize to nucleotide sequences other than their respective complementary secondary extension products but do not ligate together due to the presence of one or more mismatches and individually separate during the denaturation treatment. Following the ligase detection reaction cycles, the reporter labels of the ligation product sequences are detected which indicates the presence of one or more target nucleotide sequences in the sample.

The primary PCR/secondary PCR/LDR process of the present invention provides significant advantages over the use of PCR alone in the multiplex detection of single nucleotide and tandem repeat polymorphism-s.

As noted above, the use of PCR alone requires heavy optimization of operating conditions in order to conduct multiplex detection procedures. Moreover, the quantity of oligonucleotide primers must be increased to detect greater numbers of target nucleotide sequences. However, as this occurs, the probability of target independent reactions (e.g., the primer-dimer effect) increases. In addition, the mutations must be known, false positives may be generated by polymerase extension off of normal template, closely-clustered sites due to interference of overlapping primers cannot undergo multiplex detection, single base or small insertions and deletions in small repeat sequences cannot be detected, and quantification of mutant DNA in high background of normal DNA is difficult. As a result, the number of target nucleotide sequences detected in a single multiplex PCR process is limited.

Direct sequencing requires enrichment of mutant samples in order to correct sequences, requires multiple reactions for large genes containing many exons, requires electrophoretic separation of products, is time consuming, and cannot be used to detect mutant DNA in less than 5% of background of normal DNA. When mini-sequencing, the mutation must be known, closely-clustered sites due to interference of overlapping primers cannot undergo multiplex detection, single base or small insertions and deletions in small repeat sequences cannot be detected, and four separate reactions are required. For allele-specific oligonucleotide hybridization ("ASO"), the mutation must be known, hybridization and washing conditions must be known, cross-reactivity is difficult to prevent, closely-clustered sites due to interference of overlapping primers cannot undergo multiplex detection, and mutant DNA cannot be detected in less than 5% of background of normal DNA. Primer-mediated RFLP requires electrophoretic separation to distinguish mutant from normal DNA, is of limited applicability to sites that may be converted into a restriction site, requires additional analysis to determine the nature of the mutation, and is difficult to use where the mutant DNA is in a high background of normal DNA. Single strand conformational polymorphism analysis ("SSCP") requires electrophoretic separation to distinguish mutant conformer from normal conformer, misses 30% of possible mutations, requires additional analysis to determine the nature of the mutation, and cannot distinguish mutations from silent polymorphisms. With dideoxynucleotide finger printing ("ddF"), it is difficult to detect mutations in a high background of normal DNA, electrophoretic separation is required to distinguish mutant conformer from normal conformer, additional analysis must be used to determine the nature of the mutation, and mutations cannot be distinguished from silent polymorphisms. Denaturing gradient gel electrophoresis ("DGGE") must electrophoretically separate mutant conformer from normal conformer, misses 30% of possible mutations, requires additional analysis to determine the nature of the mutation, cannot distinguish mutations from silent polymorphisms, and imposes technical challenges to reproducing previously achieved results. RNase mismatch cleavage requires additional analysis to determine the nature of the mutation, requires analysis of both strands to exclude RNase-resistant mismatches, and imposes difficulty in detecting mutations in a high background of normal DNA. Chemical mismatch cleavage cannot detect mutant DNA in less than 5% of background of normal DNA, and requires an analysis of both strands to detect all mutations. For T4 Endo VII mismatch cleavage, additional analysis is needed to determine the nature of the mutation, mutations cannot be distinguished from silent polymorphisms, endonuclease cleaves control DNA which necessitates careful interpretation of results, and it is difficult to detect mutations in a high background of normal DNA.

These problems are avoided in the primary PCR/secondary PCR/LDR process of the present invention which combines the sensitivity of PCR with the specificity of LDR. The primary PCR phase produces primary extension products with a secondary primer-specific portion. This initial phase is carried out under conditions effective to maximize production of primary extension products without obtaining the adverse effects sometimes achieved in a PCR-only process. In particular, the primary PCR phase of the present invention is carried out with 15 to 20 PCR cycles and utilizes less primer than would be utilized in a PCR-only process. The primary PCR phase of the present invention produces extension products in a varied and unpredictable way, because some target nucleotide sequences will be amplified well, while others will not. However, in the secondary PCR phase, all of the primary extension products are amplified approximately equally, because they all have the same secondary primer-specific portions. Target nucleotide sequences originally present in the sample will not be amplified by the secondary PCR phase, because such sequences do not contain a secondary primer-specific portion. As a result, the primary PCR/secondary PCR/LDR process of the present invention is able to achieve multiplex detection of hundreds of nucleotide sequence differences in a single tube without undue customization of operating conditions for each particular sample being analyzed. Since the selection of mutant sequences is mediated by LDR rather than PCR, the primary PCR/secondary PCR/LDR process is less susceptible to false-positive signal generation. In addition, the primary PCR/secondary PCR/LDR process allows detection of closely-clustered mutations, detection of single base or small insertions and deletions in small repeat sequences, quantitative detection of less than 1% mutations in high background of normal DNA, and detection of ligation product sequences using addressable arrays. The only significant requirements are that the mutations be known and that a multitude of oligonucleotides be synthesized.

The ability to detect single nucleotide and tandem repeat polymorphisms is particularly important for forensic DNA identification and diagnosis of genetic diseases.

II. LDR/PCR Process

A second aspect of the present invention relates to a method for identifying one or more of a plurality of sequences differing by one or more single-base changes, insertions, deletions, or translocations in a plurality of target nucleotide sequences. This method has a ligase detection reaction phase followed by a polymerase chain reaction phase. This method involves providing a sample potentially containing one or more target nucleotide sequences with a plurality of sequence differences.

In the ligase detection reaction phase, one or more oligonucleotide probe sets are provided. Each set has a first oligonucleotide probe, having a target-specific portion and a 5' upstream primer-specific portion, and a second oligonucleotide probe, having a target-specific portion and a 3' downstream primer-specific portion. The oligonucleotide probes in a particular set are suitable for ligation together when hybridized adjacent to one another on a corresponding target nucleotide sequence. However, there is a mismatch which interferes with such ligation when they are hybridized to any other nucleotide sequence present in the sample. The sample, the plurality of oligonucleotide probe sets, and a ligase are blended together to form a ligase detection reaction mixture.

The ligase detection reaction mixture is subjected to one or more ligase detection reaction cycles. These cycles include a denaturation treatment and a hybridization treatment. In the denaturation treatment, any hybridized oligonucleotides are separated from the target nucleotide sequences. The hybridization treatment causes the oligonucleotide probe sets to hybridize at adjacent positions in a base-specific manner to their respective target nucleotide sequences if present in the sample. Once hybridized, the oligonucleotide probe sets ligate to one another to form a ligation product sequence. This product contains the 5' upstream primer-specific portion, the target-specific portions connected together, and the 3' downstream primer-specific portion. The ligation product sequence for each set is distinguishable from other nucleic acids in the ligase detection reaction mixture. The oligonucleotide probe sets hybridized to nucleotide sequences in the sample other than their respective target nucleotide sequences but do not ligate together due to a presence of one or more mismatches and individually separate during the subsequent denaturation treatment.

In the polymerase chain reaction, one or a plurality of oligonucleotide primer sets are provided. Each set has an upstream primer containing the same sequence as the 5' upstream primer-specific portion of the ligation product sequence and a downstream primer complementary to the 3' downstream primer-specific portion of the ligation product sequence, where one primer has a detectable reporter label. The ligase detection reaction mixture is blended with the one or a plurality of oligonucleotide primer sets and the polymerase to form a polymerase chain reaction mixture.

The polymerase chain reaction mixture is subjected to one or more polymerase chain reaction cycles which include a denaturation treatment, a hybridization treatment, and an extension treatment. During the denaturation treatment, hybridized nucleic acid sequences are separated. The hybridization treatment causes primers to hybridize to their complementary primer-specific portions of the ligation product sequence. During the extension treatment, hybridized primers are extended to form extension products complementary to the sequences to which the primers are hybridized. In a first cycle of the polymerase chain reaction phase, the downstream primer hybridizes to the 3' downstream primer-specific portion of the ligation product sequence and is extended to form an extension product complementary to the ligation product sequence. In subsequent cycles the upstream primer hybridizes to the 5' upstream primer-specific portion of the extension product complementary to the ligation product sequence and the downstream primer hybridizes to the 3' downstream portion of the ligation product sequence.

Following the polymerase chain reaction phase of this process, the reporter labels are detected and the extension products are distinguished to indicate the presence of one or more target nucleotide sequences in the sample.

One embodiment of the LDR/PCR process of the present invention achieves improved results over the use of LDR alone in measuring the number of gene copies in a cell (i.e. gene dosage). When LDR alone is utilized, it is difficult to produce sufficient target copies which are needed ultimately to quantify a plurality of genes.

In another embodiment of the LDR/PCR process of the present invention, the LDR phase ligation product sequences are produced in a ratio proportional to the ratio of the genes from which they were derived within the sample. By incorporation of the same primer-specific portions in the oligonucleotide probes for the LDR phase, the PCR phase amplifies ligation product sequences to the same degree so that their proportionality is maintained. Target sequences originally found in the sample being analyzed are not amplified by the PCR phase, because such target sequences do not contain PCR primer-specific portions. In addition, since only the oligonucleotide primers for the PCR phase have reporter labels, only extension products with those labels will be detected.

Determination of variation in gene dosage is important in a number of biomedical applications.

Males differ in gene dosage from females for those genes located on the X chromosome, women having two copies while men have one copy. Women may be carriers of deletions along the X chromosome. If the deleted region of the X chromosome included one or more genes, then the woman has only one copy of these genes in the corresponding, non-deleted area of the other X chromosome. The result (having one copy of an X-linked gene) is similar to the situation in male cells and is usually tolerated without manifestations of an inherited disorder. However, if the woman's son inherits her deleted X chromosome, he will have no copies of the genes in the deletion region and suffer from the X-linked disorder related to the absence of the gene. The detection of chromosomal deletions, therefore, is one application of the LDR/PCR process of the present invention.

Congenital chromosomal disorders occur when a fertilized egg has an abnormal compliment of chromosomes. The most common congenital chromosomal disorder is Down Syndrome, which occurs when there is an additional chromosome 21 in each cell, designated 47; XX+21 or 47, XY+21. The LDR/PCR process of the present invention can be designed to identify congenital chromosomal disorders.

The LDR/PCR process of the present invention is also useful for distinguishing polymorphisms in mono-nucleotide and di-nucleotide repeat sequences. It will also be useful in distinguishing minor populations of cells containing unique polymorphisms for detection of clonality.

The LDR/PCR process can be used with both gel and non-gel (i.e. DNA array) technologies. It allows multiplex analysis of many gene amplifications and deletions simultaneously, allows quantitative analysis, and does not require an external standard. The only relatively minor challenge presented by the LDR/PCR process is that it is difficult to use in determining the boundaries of large deletions in chromosomes.

By contrast, microsatellite marker analysis cannot be used to detect small regions that are deleted or amplified, is not compatible with simultaneous detection of amplified regions, and depends on the availability of informative markers. Competitive PCR (i.e. differential PCR) cannot be used in a multiplex format to detect several deletions and amplifications simultaneously, and is not particularly accurate. Southern hybridization is time consuming, labor intensive, is not amenable to multiplexing due to the need for multiple steps for each probe tested, and requires large quantities of DNA. Fluorescent in situ hybridization ("FISH") requires specialized expertise, is time consuming, and requires large probes to analyze for suspected deleted or amplified regions. Thus, the LDR/PCR process of the present invention constitutes a significant advance over prior processes.

III. Primary PCR/Secondary PCR Process

A third aspect of the present invention also involves a method for identifying two or more of a plurality of sequences differing by one or more single-base changes, insertions, deletions, or translocations in one or more target nucleotide sequences. This method involves subjecting a sample potentially containing one or more target nucleotide sequences with a plurality of sequence differences to two successive polymerase chain reaction phases.

For the first polymerase chain reaction phase, one or more primary oligonucleotide primer groups are provided where each group comprises two or more primary oligonucleotide primer sets. Each set has a first oligonucleotide primer, having a target-specific portion and a 5' upstream secondary primary-specific portion, and a second oligonucleotide primer, having a target-specific portion and a 5' upstream secondary primer-specific portion. The first oligonucleotide primers of each set in the same group contain the same 5' upstream secondary primer-specific portion and the second oligonucleotide primers of each set in the same group contain the same 5' upstream secondary primer-specific portion. The oligonucleotide primers in a particular set are suitable for hybridization on complementary strands of a corresponding target nucleotide sequence to permit formation of a polymerase chain reaction product. However, there is a mismatch which interferes with formation of such a polymerase chain reaction product when the primary oligonucleotide primers hybridize to any other nucleotide sequence present in the sample. The polymerase chain reaction products in a particular set may be distinguished from other polymerase chain reaction products with the same group or other groups. The primary oligonucleotide primers are blended with the sample and the polymerase to form a primary polymerase chain reaction mixture.

The primary polymerase chain reaction mixture is subjected to two or more polymerase chain reaction cycles involving a denaturation treatment, a hybridization treatment, and an extension treatment as described above. During the hybridization treatment, the target-specific portion of a primary oligonucleotide primer is hybridized to the target nucleotide sequences. In the extension treatment, the hybridized primary oligonucleotide primers are extended to form primary extension products complementary to the target nucleotide sequence to which the primary oligonucleotide primer is hybridized.

Although the upstream secondary primer-specific portions of a primary oligonucleotide primer set are not present on the target DNA, their sequences are copied by the second and subsequent cycles of the primary polymerase chain reaction phase. As a result, the primary extension products produced after the second and subsequent cycles have the secondary primer-specific portions on their 5' ends and the complement of primer-specific portion on their 3' ends.

In the second polymerase chain reaction phase of this aspect of the present invention, one or a plurality of secondary oligonucleotide primer sets are provided. Each set has a first secondary primer having a detectable reporter label and containing the same sequence as the 5' upstream portion of a first primary oligonucleotide primer, and a second secondary primer containing the same sequence as the 5' upstream primer of the second primary oligonucleotide primer from the same primary oligonucleotide primer set as the first primary oligonucleotide complementary to the first secondary primer. A set of secondary oligonucleotide primers amplify the primary extension products in a given group. The secondary oligonucleotide primers are blended with the primary extension products and the polymerase to form a secondary polymerase chain reaction mixture.

The secondary polymerase chain reaction mixture is subjected to one or more polymerase chain reaction cycles involving a denaturation treatment, a hybridization treatment, and an extension treatment, as described above. In the hybridization treatment, the secondary oligonucleotide primers are hybridized to the primary extension products, while the extension treatment causes the hybridized secondary oligonucleotide primers to be extended to form secondary extension products complementary to the primary extension products. After subjecting the secondary polymerase chain reaction mixture to the two or more polymerase chain reaction cycles, the labelled secondary extension products are detected. This indicates the presence of one or more target nucleotide sequences in the sample.

The primary PCR/secondary PCR process of the present invention provides significant advantages over Southern hybridization, competitive PCR, and microsatellite marker analysis in detecting nucleotide deletions which cause a loss of heterozygosity. Although Southern hybridization is more accurate than competitive PCR, it is quite labor intensive, requires large amounts of DNA, and neither technique can be multiplexed. Current multiplex microsatellite marker approaches require careful attention to primer concentrations and amplification conditions.

The primary PCR/secondary PCR process of the present invention overcomes these difficulties encountered in the prior art. In the primary PCR phase, the primary oligonucleotide primers flank dinucleotide or other repeat sequences and include a secondary primer-specific portion. The primary PCR phase is carried out at low concentrations of these primers to allow several loci to undergo amplification at the same time. The secondary PCR phase causes amplification to continue at the same rate with target-specific secondary primers being selected to space one set of microsatellite markers from the adjacent set. The primary PCR/secondary PCR process can be used to carry out multiplex detection in a single PCR tube and with single gel lane analysis.

This aspect of the present invention is useful in carrying out a microsatellite marker analysis to identify nucleotide deletions in a gene. Such multiplex detection can be carried out in a single reaction tube. However, the primary PCR/secondary PCR process cannot distinguish amplifications from deletions, so, when making such distinctions, this process must be used in conjunction with the above-described LDR/PCR process or a differential PCR process.

BRIEF DESCRIPTION OF THE DRAWINGS

FIG. 6 is a schematic diagram depicting a primary PCR/secondary PCR/LDR process for detection of the presence of any possible base at two nearby sites using LDR oligonucleotide probes which distinguish all possible bases at a given site.

FIG. 7 is a schematic diagram depicting a primary PCR/secondary PCR/LDR process for detection of cancer-associated mutations at adjacent alleles.

FIG. 23 is a schematic diagram depicting a primary PCR/secondary PCR process for multiplex detection of insertions and deletions in microsatellite repeats.

FIGS. 26A-C show electropherogram results for an LDR/PCR process of ErbB, G6PD, Int2, p53, and SOD gene segments from normal human: female DNA and from DNA of the breast cancer cell line ZR-75-30 and the gastric carcinoma cell line SKGT-2. The ErbB gene is known to be amplified in the cancer cell lines. Target-specific ligation product sequences of 104 bp are generated in 10 cycles (94° C. for 30 sec, 65° C. for 4 min) of LDR using 500 femtomoles of each ligation primer, 50 ng of genomic DNA, 124 units of Thermus thermophillus ("Tth") ligase, 2 µl of 10× buffer (0.2 M Tris, pH 8.5 and 0.1 M $MgCl_2$), 2 µl of 10 mM NAD, and 1 µl of 200 mM DTT in a volume of 20 µl. The ligation products are proportionally amplified in 26 cycles (94° C. for 15 sec, 60° C. for 50 sec) of PCR by the addition of 30 µl of a solution containing 5 µl 10× Stoffel buffer (Perkin Elmer), 25 picomoles of each oligonucleotide primer, 2.5 units of Taq polymerase Stoffel fragment, and 8 µl of a solution 5 mM in each dNTP. After amplification, the products are digested with HaeIII and HinP1I to generate FAM-labeled products of 58 bp (ErbB (i.e. HER-2/neu/erbB oncogene)), 61 bp (G6PD), 67 bp (Int2 (i.e. int-2 oncogene)), 70 bp (p53) and 76 bp (SOD). These products are separated and analyzed on a 373A DNA sequencer using the Genescan 672 software package (Applied Biosystems, Inc., Foster City, Calif.). Results are displayed as electropherograms such that peak heights and areas reflect the amounts of the PCR products. In FIG. 26A, the gene dosage determination for the five loci in normal human female DNA is shown. The peak heights and areas for G6PD, Int2, p53, and SOD are very similar. The peak height and area for ErbB is consistently small in normal genomic DNA. In FIG. 26B, the peak height and area for ErbB are elevated when gene dosage is investigated in ZR-75-30, a cell line with known ErbB amplification. In FIG. 26C, the gastric cell line, SKGT-2 shows dramatic amplification of the ErbB gene and a modest amplification of Int2. The G6PD gene peak may be embedded in the large ErbB peak.

FIGS. 27A-C show electropherogram results for an LDR/PCR process to determine whether amplification of ErbB affected the relative peak heights of the other LDR oligonucleotide probes and PCR oligonucleotide primers for G6PD, Int2, p53, and SOD. In FIG. 27A, the gene dosage determination for the four loci in normal human female DNA is shown. Peak heights and areas for G6PD, Int2, p53, and SOD are similar, as they were in the experiment using all five LDR primers. In FIG. 27B, G6PD, Int2, and, SOD analyzed in the ZR-75-30 breast cancer cell line show similar relative peak heights, comparable to their appearance in normal female DNA. The peak height for p53 is reduced, suggesting the deletion of this gene in a portion of the cells in this cell line. In FIG. 27C, in the gastric carcinoma cell line, SKGT-2, G6PD, and p53 show comparable peak heights. The Int2 peak height remains relatively high, as it was in the experiment using all five LDR oligonucleotide probes. Thus, the LDR and PCR amplification of each product appears to be independent of the other products during the course of the experiment.

DETAILED DESCRIPTION OF THE INVENTION

I. Primary PCR/Secondary PCR/LDR Process

Figure 1:
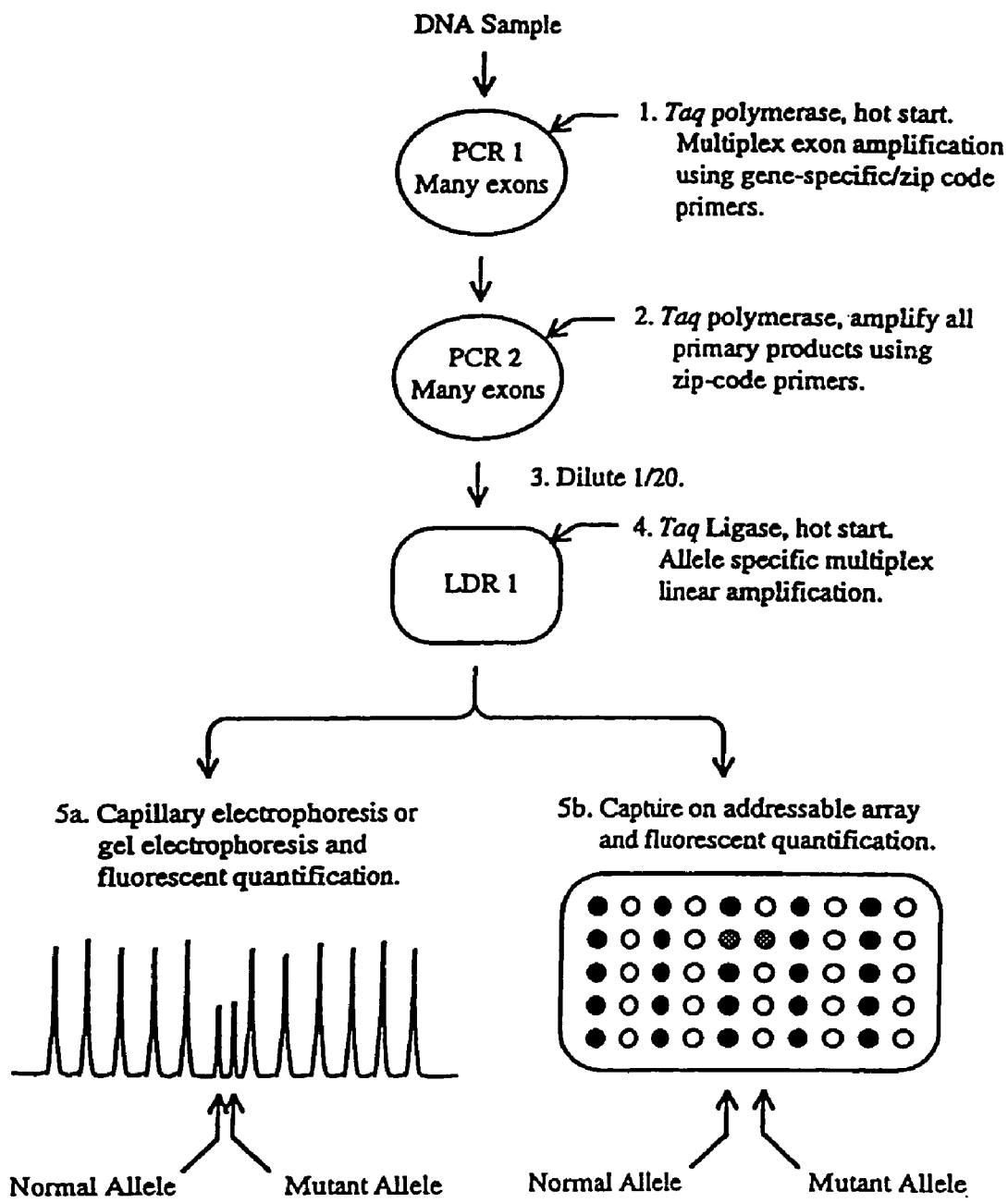
FIG. 1 is a flow diagram depicting a primary PCR/secondary PCR/LDR process for detection of germline mutations, such as point mutations, by electrophoresis or capture on an addressable array. Note that the term "zipcode" which appears in FIG. 1 and other drawings refers to a sequence specific to a subsequently used primer or probe but not to either the target sequence or other genome sequences.

One aspect of the present invention relates to a method for identifying two or more of a plurality of sequences differing by one or more single-base changes, insertions, deletions, or translocations in a plurality of target nucleotide sequences.

This method involves a first polymerase chain reaction phase, a second polymerase chain reaction phase, and a ligase detection reaction phase. This process involves analyzing a sample potentially containing one or more target nucleotide sequences with a plurality of sequence differences.

In the first polymerase chain reaction phase, one or more primary oligonucleotide primer groups are provided. Each group comprises one or more primary oligonucleotide primer sets with each set having a first oligonucleotide primer, having a target-specific portion and a 5' upstream secondary primer-specific portion, and a second oligonucleotide primer, having a target-specific portion and a 5' upstream secondary primer-specific portion. The first oligonucleotide primers of each set in the same group contain the same 5' upstream secondary primer-specific portion and the second oligonucleotide primers of each set in the same group contain the same 5' upstream primer-specific portion. The oligonucleotide primers in a particular set are suitable for hybridization on complementary strands of a corresponding target nucleotide sequence to permit formation of a polymerase chain reaction product. However, there is a mismatch which interferes with formation of such a polymerase chain reaction product when the primary oligonucleotide primers hybridize to any other nucleotide sequence present in the sample. The polymerase chain reaction products in a particular set may be distinguished from other polymerase chain reaction products in the same group or groups. The primary oligonucleotide primers, the sample, and the polymerase are blended to form a primary polymerase chain reaction mixture.

The primary polymerase chain reaction mixture is subjected to two or more polymerase chain reaction cycles involving a denaturation treatment, a hybridization treatment, and an extension treatment, as substantially described above. During hybridization, target-specific portions of the primary oligonucleotide primers hybridize to the target nucleotide sequences. The extension treatment causes hybridized primary oligonucleotide primers to be extended to form primary extension products complementary, to the target nucleotide sequence to which the primary oligonucleotide primers are hybridized.

Although the upstream secondary primer-specific portions of a primary oligonucleotide primer set are not present on the target DNA, their sequences are copied by the second and subsequent cycles of the primary polymerase chain reaction phase. As a result, the primary extension products produced after the second cycle have the secondary primer-specific portions on their 5' ends and the complement of the primer-specific portion on their 3' ends.

Next, there is a second polymerase chain reaction phase. This phase involves providing one or a plurality of secondary oligonucleotide primer sets. Each set has a first secondary oligonucleotide primer containing the same sequence as the 5' upstream portion of the first primary oligonucleotide primer, and a second secondary oligonucleotide primer containing the same sequence as the 5' upstream portion of the second primary oligonucleotide primer from the same primary oligonucleotide primer set as the first primary oligonucleotide complementary to the first secondary primer. A set of secondary oligonucleotide primers may be used to amplify all of the primary extension products in a given group. The secondary oligonucleotide primers are blended with the primary extension products and the polymerase to form a secondary polymerase chain reaction mixture.

The secondary polymerase chain reaction mixture is subjected to one or more polymerase chain reaction cycles having a denaturation treatment, a hybridization treatment, and an extension treatment, as substantially set forth above. During the hybridization treatment, the secondary oligonucleotide primers hybridize to complementary sequences present on the primary extension products but not to the original target sequence. The extension treatment causes the hybridized secondary oligonucleotide primers to be extended to form secondary extension products complementary to the primary extension products.

The last phase of this aspect of the present invention involves a ligase detection reaction process. Here, a plurality of oligonucleotide probe sets are provided where each set has a first oligonucleotide probe, having a secondary extension product-specific portion and a detectable reporter label, and a second oligonucleotide probe, having a secondary extension product-specific portion. The oligonucleotide probes in a particular set are suitable for ligation together when hybridized adjacent to one another on a complementary secondary extension product-specific portion. However, there is a mismatch which interferes with such ligation when the oligonucleotide probes are hybridized to any other nucleotide sequence present in the sample. The ligation product of oligonucleotide probes in a particular set may be distinguished from either individual probes or other ligation products. The plurality of oligonucleotide probe sets, the secondary extension products, and a ligase are blended to form a ligase detection reaction mixture.

The ligase detection reaction mixture is subjected to one or more ligase detection reaction cycles having a denaturation treatment and hybridization treatment substantially as described above. In the hybridization treatment, the oligonucleotide probe sets hybridize at adjacent positions in a base-specific manner to the respective secondary extension products if present. As a result, adjacent probes ligate to one another to form a ligation product sequence containing the detectable-reporter label and the secondary extension product-specific portions connected together. The oligonucleotide probe sets may hybridize to nucleotide sequences other than the respective complementary secondary extension products but do not ligate together due a presence of one or more mismatches and individually separate during the denaturation treatment. Following the ligation detection reaction cycles, the reporter labels of the ligation product sequences are detected which indicates the presence of one or more target nucleotide sequences in the sample.

Figure 2:
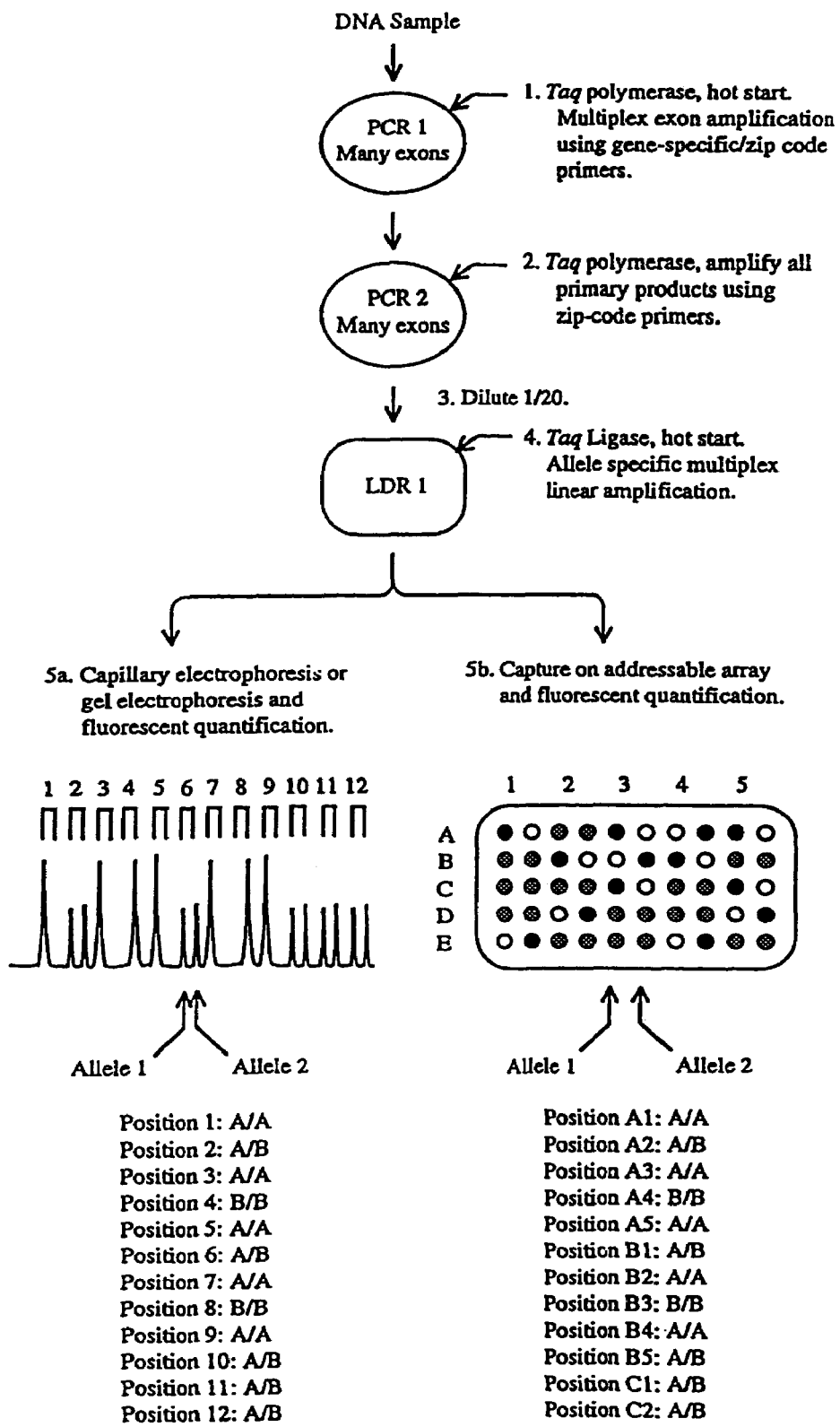
FIG. 2 is a flow diagram depicting a primary PCR/secondary PCR/LDR process for detection of biallelic polymorphisms by electrophoresis or capture on an addressable array.
Figure 3:
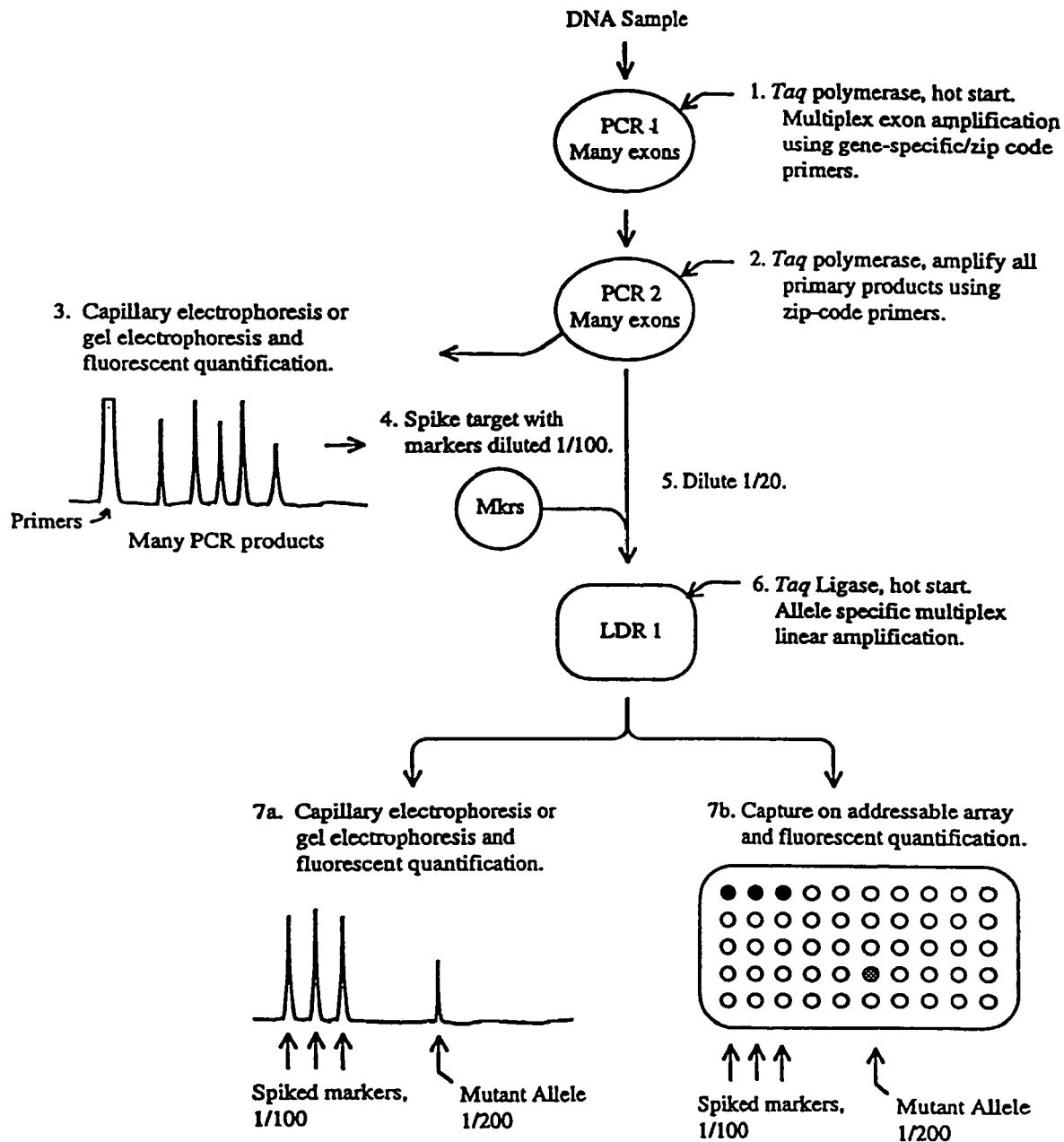
FIG. 3 is a flow diagram depicting a primary PCR/secondary PCR/LDR process for detection of cancer-associated mutations by electrophoresis or capture on an addressable array.

FIGS. 1, 2, and 3 show flow diagrams of the primary PCR/secondary PCR/LDR process of the present invention utilizing-either of two detection procedures. One alternative involves use of capillary electrophoresis or gel electrophoresis and a fluorescent quantification procedure. Alternatively, detection can be carried out by capture on an array of capture oligonucleotide addresses and fluorescent quantification. FIG. 1 relates to detection of germline mutations (e.g., a point mutation), while FIG. 2 detects biallelic polymorphisms, and FIG. 3 shows the detection of cancer-associated mutations.

FIG. 1 depicts the detection of a germline point mutation. In step 1, after DNA sample preparation, multiple exons are subjected to primary PCR amplification using. Taq (i.e. *Thermus aquaticus*) polymerase under hot start conditions with oligonucleotide primers having a target-specific portion and a secondary primer-specific portion. At the end of the primary PCR phase, Taq polymerase may be inactivated by heating at 100° C. for 10 min or by a freeze/thaw step. The products of the primary PCR amplification phase are then subjected in step 2 to secondary PCR amplification using Taq polymerase under hot start conditions with the secondary oligonucleotide primers. At the end of the secondary PCR phase, Taq polymerase may be inactivated by heating at 100° C. for 10 min or by a freeze/thaw step. In step 3, products of the secondary PCR phase are then diluted 20-fold into fresh LDR buffer containing LDR oligonucleotide probes containing allele-specific portions and common portions. step 4 involves the LDR phase of the process which is initiated by addition of Taq ligase under hot start conditions. During LDR, oligonucleotide probes ligate to their adjacent oligonucleotide probes only in the presence of target sequence which gives perfect complementarity at the junction site. The products may be detected in two different formats. In the first format 5a, fluorescently-labeled LDR probes contain different length poly A or hexaethylene oxide tails. Thus, each ligation product sequence (resulting from ligation of two probes hybridized on normal DNA) will have a slightly different length and mobility such that several ligation product sequences yield a ladder of peaks. Thus, each ligation product (resulting from ligation of two probes hybridized on normal DNA) will have a slightly different length and mobility such that several ligation product sequences yield a ladder of peaks. A germline mutation would generate a new peak on the electropherogram. Alternatively, the LDR probes may be designed such that the germline mutation ligation product sequence migrates with the same mobility as a normal DNA ligation product sequence, but it is distinguished by a different fluorescent reporter. The size of the new peak will approximate the amount of the mutation present in the original sample; 0% for homozygous normal, 50% for heterozygous carrier, or 100% for homozygous mutant. In the second format 5b, each allele-specific probe contains e.g., 24 additional nucleotide bases on their 5' ends. These sequences are unique addressable sequences which will specifically hybridize to their complementary address sequences on an addressable array. In the LDR reaction, each allele-specific probe can ligate to its adjacent fluorescently labeled common probe in the presence of the corresponding target sequence. Ligation product sequences corresponding to wild type and mutant alleles are captured on adjacent addresses on the array. Unreacted probes are washed away. The black dots indicate 100% signal for the wild type allele. The white dots indicate 0% signal for the mutant alleles. The shaded dots indicate the one position of germline mutation, 50% signal for each allele.

FIG. 2 depicts the detection of biallelic polymorphisms. In step 1, after DNA sample preparation, multiple exons are subjected to primary PCR amplification using Taq polymerase under hot start-conditions with oligonucleotide primers having a target-specific portion and a secondary primer-specific portion. The products of the primary PCR amplification phase are then subjected in step 2 to secondary PCR amplification using Taq polymerase under hot start conditions with the secondary oligonucleotide primers. At the end of the secondary PCR phase, Taq polymerase may be inactivated by heating at 100° C. for 10 min or by a freeze/thaw step. In step 3, products of the secondary PCR phase are then diluted 20-fold into fresh LDR buffer containing LDR oligonucleotide probes containing allele-specific portions and common portions. step 4 involves the LDR phase of the process which is initiated by addition of Taq ligase under hot start conditions. During LDR, oligonucleotide probes ligate to their adjacent oligonucleotide probes only in the presence of target sequence which gives perfect complementarity at the junction site. In the first format 5a, fluorescently-labeled LDR probes contain different length poly A or hexaethylene oxide tails. Each ligation product sequence will have a slightly different length and mobility, such that several LDR products yield a ladder of peaks. Alternatively, the LDR probes may be designed such that the ligation products for polymorphic alleles migrate at the same position but are distinguished by different fluorescent reporter groups. The size of the peaks will approximate the amount of each allele. In the second format 5b, each oligonucleotide probe contains unique addressable sequences with e.g., 24 additional nucleotide bases on their 5' ends. These sequences will specifically hybridize to their complementary address sequences on an array of capture oligonucleotides. In the LDR phase, each allele-specific probe can ligate to its adjacent fluorescently labeled common probe in the presence of corresponding target sequence. Ligation product sequences corresponding to each allele are captured on the array, while unligated oligonucleotide probes are washed away. The black dots indicate that both chromosomes have a given allele, the white dots show that neither chromosome has that allele, and the shaded dots indicate that one chromosome has a given allele.

FIG. 3 depicts the detection of cancer-associated mutation. In step 1, after DNA sample preparation, multiple exons are subjected to primary PCR amplification using Taq polymerase under hot start conditions with oligonucleotide primers having a target-specific portion and a secondary primer-specific portion. The products of the primary PCR amplification phase are then subjected in step 2 to secondary PCR amplification using Taq polymerase under hot start conditions with the secondary oligonucleotide primers. At the end of the secondary PCR phase, Taq polymerase may be inactivated by heating at 100° C. for 10 min or by a freeze/thaw step. Fluorescent quantification of PCR products can be achieved using capillary or gel electrophoresis in step 3. In step 4, the products are spiked with a 1/100 dilution of marker DNA (for each of the fragments). This DNA is homologous to wild type DNA, except it contains a mutation which is not observed in cancer cells, but which may be readily detected with the appropriate LDR probes. In step 5, the mixed DNA products in products of the secondary PCR phase are then diluted 20-fold into fresh LDR buffer containing LDR oligonucleotide probes containing allele-specific portions and common portions. step 6 involves the LDR phase of the process which is initiated by addition of Taq ligase under hot start conditions. During LDR, oligonucleotide probes ligate to their adjacent oligonucleotide probes only in the presence of target sequence which gives perfect complementarity at the junction site.

The products may be detected in the same two formats discussed above. In the format of step 7a, products are separated by capillary or gel electrophoresis, and fluorescent signals are quantified. Ratios of mutant peaks to marker peaks give the approximate amount of cancer mutations present in the original sample divided by 100. In the format of step 7b, products are detected by specific hybridization to complementary sequences on an addressable array. Ratios of fluorescent signals in mutant dots to marker dots give the approximate amount of cancer mutations present in the original sample divided by 100.

Figure 4:
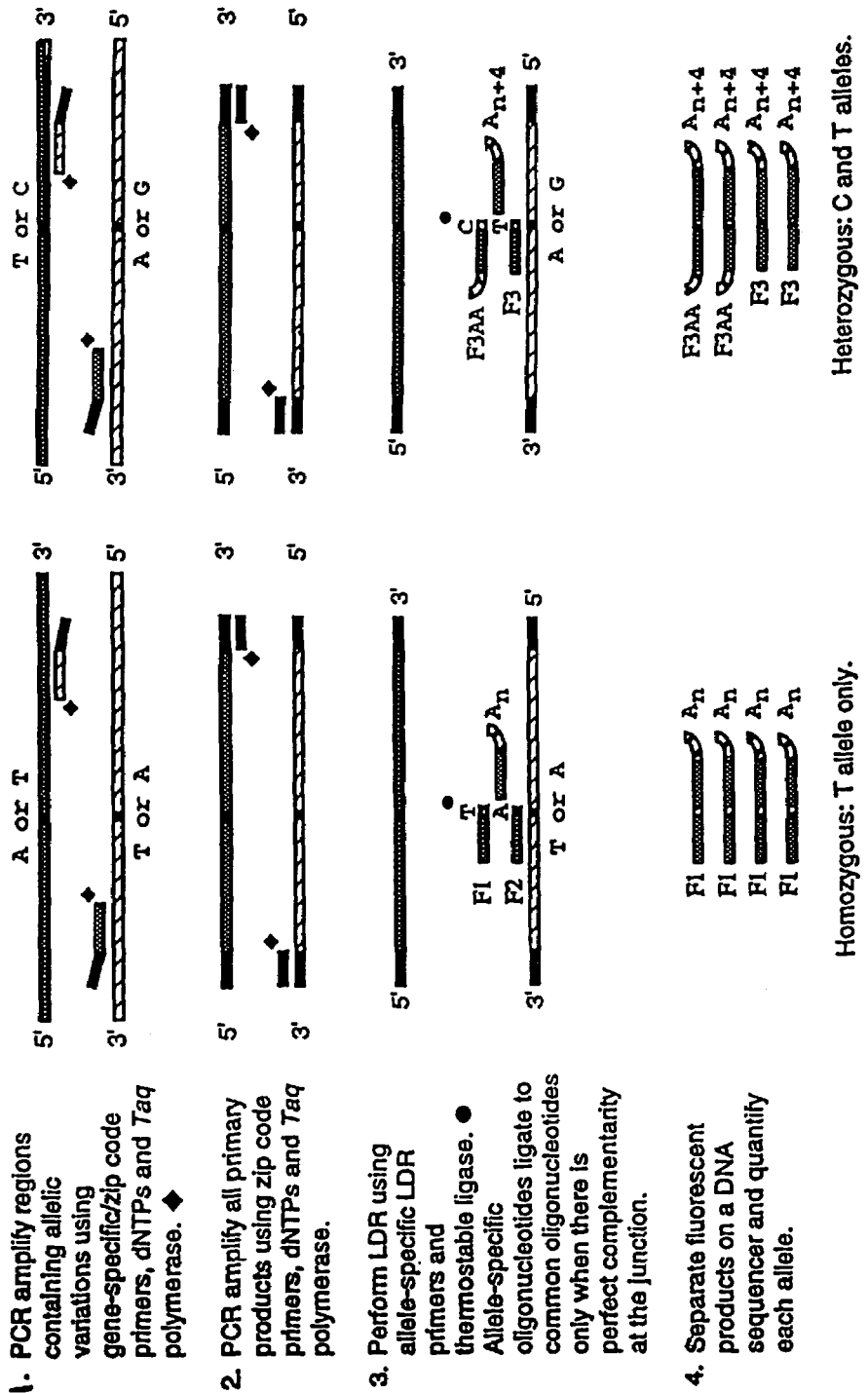
FIG. 4 is a schematic diagram depicting a primary PCR/secondary PCR/LDR process for detection of biallelic polymorphisms.

As shown in FIG. 4, two DNA fragments of interest are treated with the primary PCR/secondary PCR/LDR process of the present invention. Initially, the double stranded DNA molecules are denatured to separate the strands. This is achieved by heating to a temperature of 80-105° C. Low concentrations of primary PCR oligonucleotide primers, containing a 3' target-specific portion (shaded area) and 5' secondary primer-specific portion (black area), are then added and allowed to hybridize to the strands, typically at a temperature of 50-85° C. A thermostable polymerase (e.g., *Taq aquaticus* polymerase) is also added, and the temperature is then adjusted to 50-85° C. to extend the primer along the length of the nucleic acid to which the primer is hybridized. After the extension phase of the polymerase chain reaction, the resulting double stranded molecule is heated to a temperature of 80-105° C. to denature the molecule and to separate the strands. These hybridization, extension, and denaturation steps may be repeated a number of times to amplify the target to an appropriate level.

In the secondary PCR phase, the products of the primary PCR phase are blended with secondary PCR oligonucleotide primers and allowed to hybridize to one another, typically at a temperature of 50-85° C. The secondary oligonucleotide primers are usually used in higher concentrations than are the primary oligonucleotide primers. Taq polymerase is also added, and the temperature is then adjusted to 50-85° C. to extend the primer along the length of the primary PCR extension products to which the secondary oligonucleotide primer is hybridized. After the extension phase of the polymerase chain reaction, the resulting double stranded molecule is heated to a temperature of 80-105° C. to denature the molecule and to separate the strands. These hybridization, extension, and denaturation steps may be repeated a number of times to amplify the target to an appropriate level.

Once the secondary PCR phase of the process is completed, the ligation detection reaction phase begins, as shown in FIG. 4. After denaturation of the target nucleic acid, if present as a double stranded DNA molecule, at a temperature of 80-105° C., preferably 94° C., ligation detection reaction oligonucleotide probes for one strand of the target nucleotide sequence are added along with a ligase (for example, as shown in FIG. 4, a thermostable ligase like *Thermus aquaticus* ligase). The oligonucleotide probes are then allowed to hybridize to the target nucleic acid molecule and ligate together, typically, at a temperature of 45-85° C., preferably, 65° C. When there is perfect complementarity at the ligation junction, the oligonucleotides can be ligated together. Where the variable nucleotide is T or A, the presence of T in the target nucleotide sequence will cause the oligonucleotide probe with the F1 reporter label to ligate to the common oligonucleotide probe with the 5' poly A tail $A_n$, and the presence of A in the target nucleotide sequence will cause the oligonucleotide probe with the F2 reporter label to ligate to the common oligonucleotide probe with $A_n$. Similarly, where the variable nucleotide is A or G, the presence of T in the target nucleotide sequence will cause the oligonucleotide probe with F3AA reporter label (i.e. the F3 reporter label coupled to 2 additional bases forming a 5' poly A spacer) to ligate to the common oligonucleotide probe with the 5' poly A tail $A_{n+4}$, and the presence of C in the target nucleotide sequence will cause the oligonucleotide probe with the F3 reporter label to ligate to the common oligonucleotide probe with the 5' poly A tail $A_{n+4}$. Following ligation, the material is again subjected to denaturation to separate the hybridized strands. The hybridization/ligation and denaturation steps can be carried out through one or more cycles (e.g., 1 to 50 cycles) to amplify target signals. Equimolar ligation of both F3-labeled oligonucleotides indicates the individual is heterozygous for that locus, whereas ligation of only the F2 labeled oligonucleotides indicates the individual is homozygous for the other locus.

In FIG. 4, the poly $A_n$ and poly $A_{n+4}$ tails are used where quantification is to be carried out by capillary or gel electrophoresis. The tails of differing length cause the corresponding different ligation product sequences to form bands at different locations in the gel or capillary. The presence of these bands at different locations permit the corresponding nucleotide differences in the DNA being analyzed to be identified. Although ligation product sequences can be distinguished based on the use of different reporter labels, the combination of different reporter labels and different length tails permits greater numbers of nucleotide differences to be distinguished. This is important for multiplex detection processes.

As noted above with respect to FIGS. 1 to 3, detection can be carried out on an addressable array instead of with gel or capillary electrophoresis. The use of such addressable arrays require that the poly A tails on the LDR oligonucleotide probe not containing a reporter label (i.e. tails $A_n$ and $A_{n+4}$) be replaced with different addressable array-specific oligonucleotide portions. As explained more fully infra, a solid support is provided with an array of capture oligonucleotides, some of which are complementary to the different addressable array-specific oligonucleotide portions. Hybridization of these portions to their complementary capture oligonucleotide probes indicates the presence of a corresponding nucleotide: difference.

Figure 5:
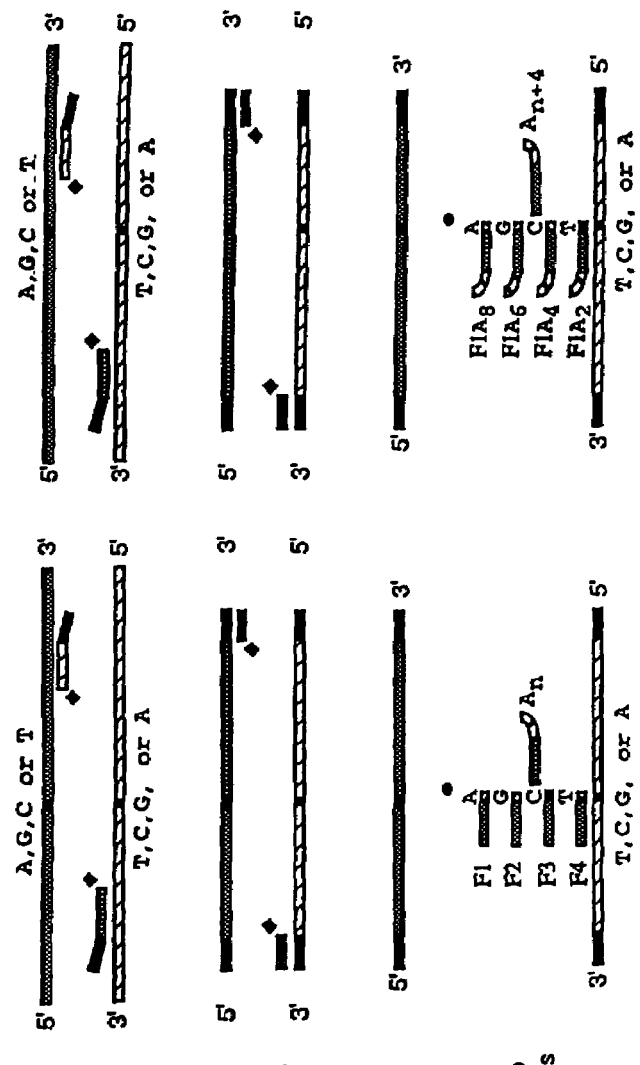
FIG. 5 is a schematic diagram depicting a primary PCR/secondary PCR/LDR process for detection of allelic differences using LDR oligonucleotide probes which distinguish all possible bases at a given site.

FIG. 5 is a schematic diagram of a primary PCR/secondary PCR/LDR process, in accordance with the present invention, where any possible base in 2 DNA molecules of interest are distinguished. The primary and secondary PCR processes are carried out in substantially the same way as described for FIG. 4. Appearance of fluorescent reporter labels F1, F2, F3, and F4 in conjunction with the left hand DNA molecule indicates the presence of the A, G, C, and T alleles in the DNA molecule, respectively. As shown in FIG. 5, equal amounts of the F1 and F3 reporter labels indicates that the individual in question is heterozygous for the A and C alleles. With respect to analysis of the right hand DNA molecule in FIG. 5, the same reporter label is used to indicate the presence of the different alleles; however, on each oligonucleotide probe with the distinguishing bases, there are different 5' poly A tails. More particularly, a 2 unit poly A tail, a 4 unit poly A tail, a 6 unit poly A tail, and an 8 unit poly A tail correspond to the T, C, G, and A alleles in the DNA molecule, respectively. As shown in FIG. 5, equal amounts of the F1 reporter label with the $A_6$ and $A_4$ tails indicates that the individual in question is heterozygous for the G and C alleles.

FIG. 6 is a schematic diagram of a primary PCR/secondary PCR/LDR process, in accordance with the present invention, for detecting the presence of any possible base at two nearby sites in DNA molecules of interest. The primary and secondary PCR phases are carried out in substantially the same way as described for FIG. 4. Here, the LDR probes are able to overlap, yet are still capable of ligating provided there is perfect complementarity at the junction. This distinguishes LDR from other approaches, such as allele-specific PCR where overlapping primers would interfere with one another. In FIG. 6, the discriminating oligonucleotide probes contain the reporter label with the discriminating base on the 3' end of these probes. The poly A tails are on the 3' end of common oligonucleotide probes. In the left hand DNA molecule, the presence of equal amounts of ligation product sequences with reporter labels F1 and F3 shows that the individual in question is heterozygous for the A and C alleles in the first position. Similarly, in the second position for the left hand DNA molecule, the presence of ligation product sequences with reporter labels F2, F3, and F4 shows that the individual in question is heterozygous for the G, C, and T alleles. Turning to the right hand DNA molecule, the presence of equal amounts of ligation product sequences with reporter label F1 having the $A_6$ and $A_4$ tails indicates that at the first position, the individual in question is heterozygous for the G and C alleles. In the second position for the right hand DNA molecule, the presence of the equal amounts of ligation product sequences with reporter label F1 having the $A_8$ and $A_2$ tails indicates that the individual in question is heterozygous for the A and T alleles.

FIG. 7 is a schematic diagram depicting the use of the primary PCR/secondary PCR/LDR process of the present invention to detect a low abundance mutation in the presence of an excess of normal sequence. Here, in the left hand DNA molecule is codon 12 of the K-ras gene, sequence GGT which codes for glycine ("Gly"). A small percentage of the cells contain the G to A mutation in GAT, which codes for aspartic acid ("Asp"). The LDR probes for wild-type (i.e. normal) sequences are missing from the reaction. If the normal LDR probes (with the discriminating base being G) were included, they would ligate to the common probes and overwhelm any signal coming from the mutant target. Instead, as shown in FIG. 7, the existence of a ligation product sequence with fluorescent label F1 and the $A_{n+2}$ tail indicates the presence of the aspartic acid encoding mutant. In the right hand DNA molecule, FIG. 7 shows codon 61 of the K-ras gene sequence CAG which codes for glutamine ("Gln"). A small percentage of the cells contain the C to G mutation in GAG, which codes for glutamic acid ("Glu"). Again, the LDR oligonucleotide probes do not include the C and A bases found in the wild type form to avoid overwhelming the mutant signal. For this DNA molecule, the existence of a ligation product sequence with fluorescent label F2 and the $A_{n+4}$ tail indicates the presence of the glutamic acid encoding mutant.

II. LDR/PCR Process

A second aspect of the present invention relates to a method for identifying one or more of a plurality of sequences differing by one or more single-base changes, insertions, deletions, or translocations in a plurality of target nucleotide sequences. This method has a ligase detection reaction phase followed by a polymerase chain reaction phase. This method involves providing a sample potentially containing one or more target nucleotide sequences with a plurality of sequence differences.

In the ligase detection reaction phase, one or more of oligonucleotide probe sets are provided. Each set has a first oligonucleotide probe, having a target-specific portion and a 5' upstream primer-specific portion, and a second oligonucleotide probe, having a target-specific portion and a 3' downstream primer-specific portion. The oligonucleotide probes in a particular set are suitable for ligation together when hybridized adjacent to one another on a corresponding target nucleotide sequence. However, there is a mismatch which interferes with such ligation when they are hybridized to any other nucleotide sequence present in the sample. The sample, the plurality of oligonucleotide probe sets, and a ligase are blended together to form a ligase detection reaction mixture.

The ligase detection reaction mixture is subjected to one or more ligase detection reaction cycles. These cycles include a denaturation treatment and a hybridization treatment. In the denaturation treatment, any hybridized oligonucleotides are separated from the target nucleotide sequences. The hybridization treatment causes the oligonucleotide probe sets to hybridize at adjacent positions in a base-specific manner to their respective target nucleotide sequences if present in the sample. Once hybridized, the oligonucleotide probe sets ligate to one another to form a ligation product sequence. This product contains the 5' upstream primer-specific portion, the target-specific portions connected together, and the 3' downstream primer-specific portion. The ligation product sequence for each set is distinguishable from other nucleic acids in the ligase detection reaction mixture. The oligonucleotide probe sets hybridized to nucleotide sequences in the sample other than their respective target nucleotide sequences but do not ligate together due to a presence of one or more mismatches and individually separate during the denaturation treatment.

In the polymerase chain reaction, one or a plurality of oligonucleotide primer sets are provided. Each set has an upstream primer containing the same sequence as the 5' upstream primer-specific portion of the ligation product sequence and a downstream primer complementary to the 3' downstream primer-specific portion of the ligation product sequence, where one primer has a detectable reporter label. The ligase detection reaction mixture is blended with the one or a plurality of oligonucleotide primer sets and the polymerase to form a polymerase chain reaction mixture.

The polymerase chain reaction mixture is subjected to one or more polymerase chain reaction cycles which include a denaturation treatment, a hybridization treatment, and an extension treatment. During the denaturation treatment, hybridized nucleic acid sequences are separated. The hybridization treatment causes primers to hybridize to their complementary primer-specific portions of the ligation product sequence. During the extension treatment, hybridized primers are extended to form extension products complementary to the sequences to which the primers are hybridized. In a first cycle of the polymerase chain reaction phase, the downstream primer hybridizes to the 3' downstream primer-specific portion of the ligation product sequence and is extended to form an extension product complementary to the ligation product sequence. In subsequent cycles, the upstream primer hybridizes to the 5' upstream primer-specific portion of the extension product complementary to the ligation product sequence and the 3' downstream primer hybridizes to the 3' downstream portion of the ligation product sequence.

Following the polymerase chain reaction phase of this process, the reporter labels are detected and the extension products are distinguished to indicate the presence of one or more target nucleotide sequences in the sample.

Figure 8:
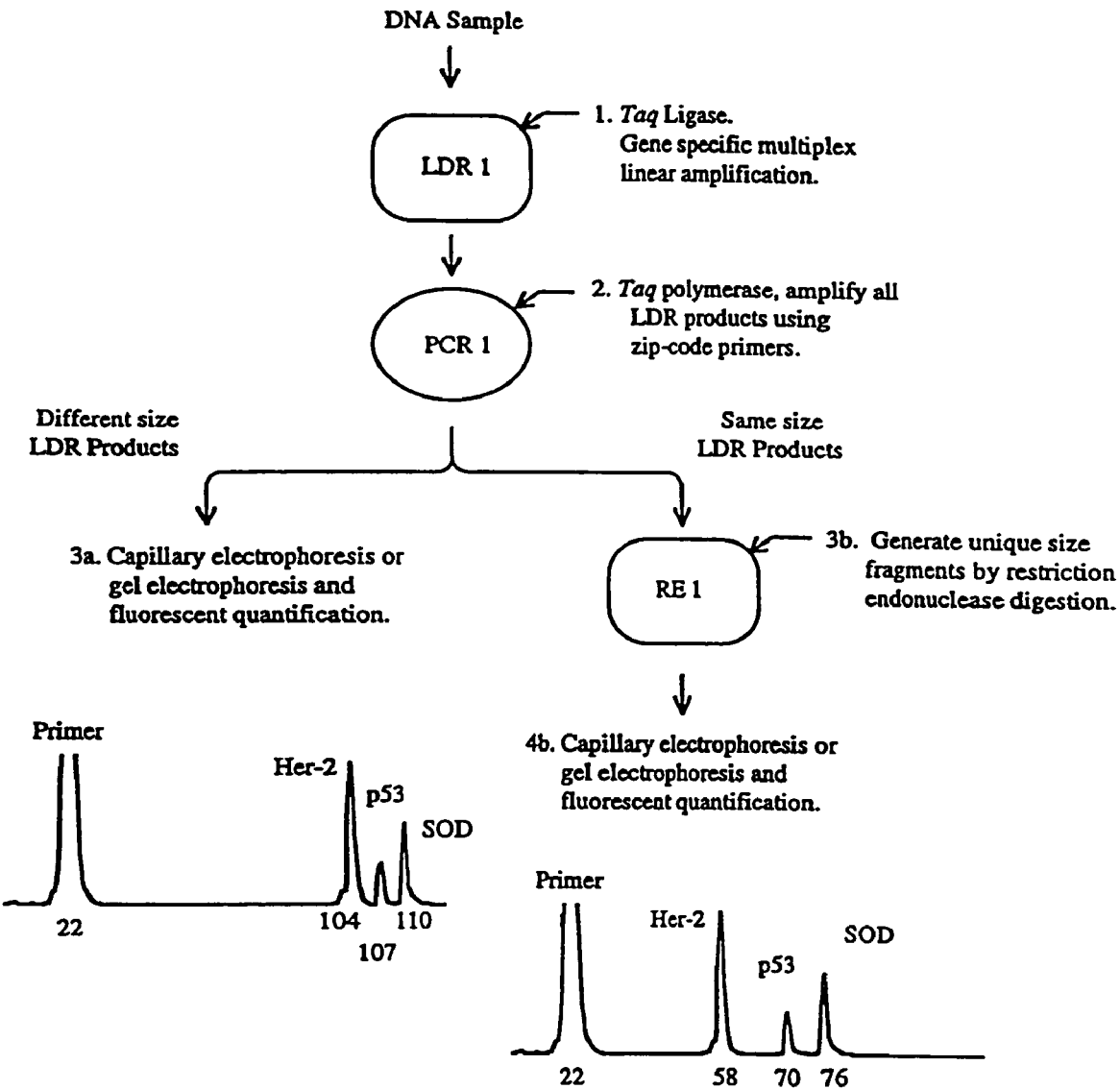
FIG. 8 is a flow diagram depicting an LDR/PCR process with and without restriction endonuclease digestion using electrophoresis detection.

FIG. 8 is a flow diagram depicting the LDR/PCR process of the present invention with or without restriction endonuclease digestion and using capillary electrophoresis detection. In step 1, a DNA sample is mixed with Taq ligase and oligonucleotide probes containing a target-specific portion and a primer-specific portion. The mixture is subjected to an LDR process to produce ligation product sequences containing the ligated target-specific portions and the primer-specific portions. step 2 involves mixing the ligation product sequences with Taq polymerase and primers and subjecting the mixture to a PCR process. The next step is determined as a function of whether the ligation product sequences are the same or different sizes. Where the ligation product sequences are different sizes, step 3a is selected which involves subjecting the extension products from PCR to capillary electrophoresis or gel electrophoresis, either of which is followed by fluorescent quantification. Step 3b is utilized where the ligation product sequences are the same size and involves subjecting the extension products from the PCR phase to restriction endonuclease digestion. This generates digestion fragments of unique size which can be subjected to capillary electrophoresis or gel electrophoresis, followed by fluorescent quantification, according to step 4b. When step 3a is selected, the curve generated as a result of electrophoresis shows three ligation product sequences migrating at lengths of 104, 107, and 110, with the peak areas representing amplification of the Her-2 gene, loss of heterozygosity of the p53 gene, and the control SOD gene, respectively. The electrophoresis curve where steps 3b and 4b are used involves three ligation product sequence restriction fragments at lengths of 58, 70, and 76, with the peak areas representing amplification of the Her-2 gene, loss of heterozygosity of the p53 gene, and the control SOD gene, respectively.

Figure 9:
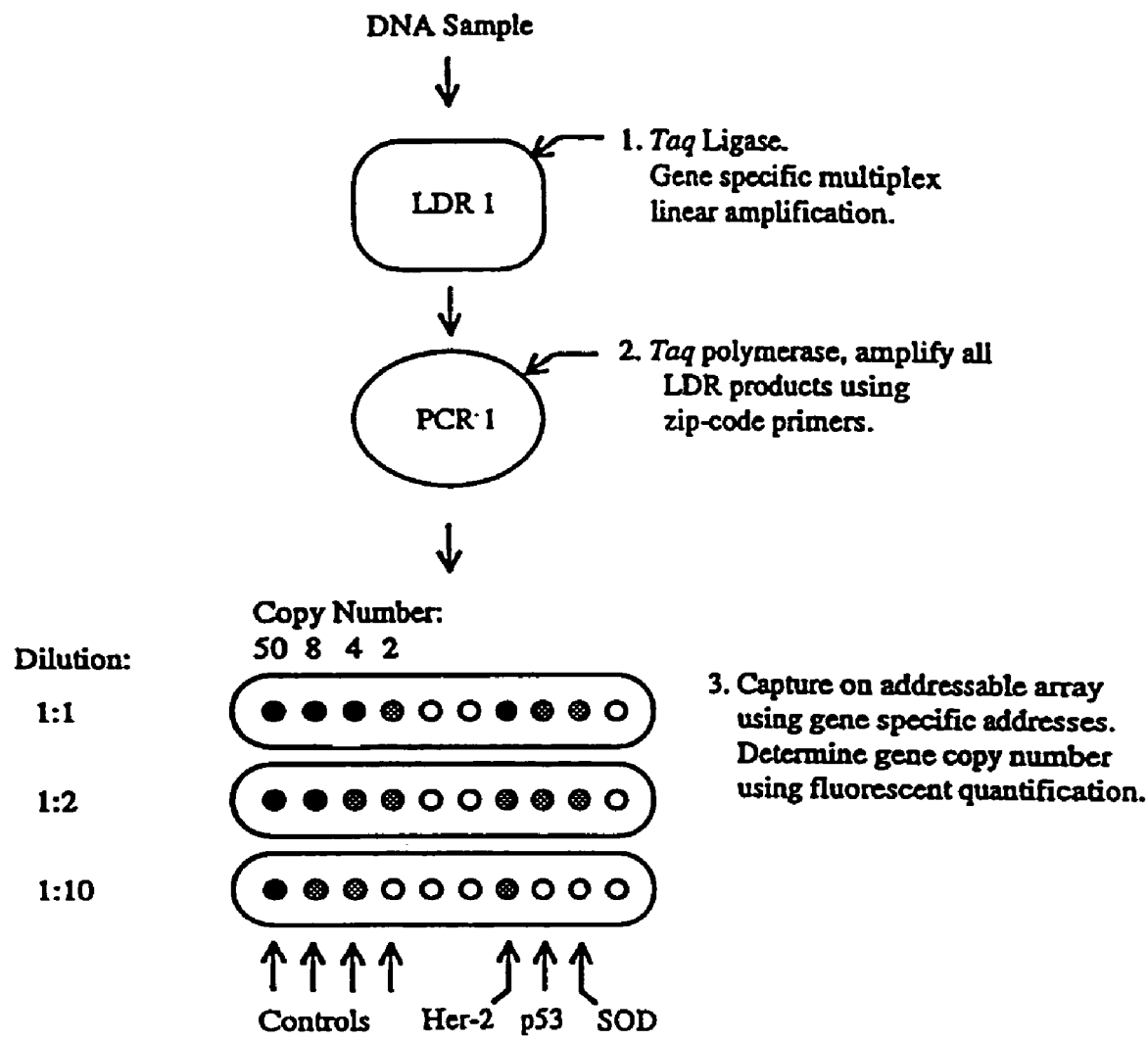
FIG. 9 is a flow diagram depicting an LDR/PCR process using detection on an addressable array using gene-specific addresses.

As an alternative to FIG. 8, FIG. 9 shows the LDR/PCR process of the present invention where, in step 3, the extension products are captured on an array of capture oligonucleotide addresses. The capture oligonucleotide probes can be complementary to a nucleotide sequence across the ligation junction. The number of gene copies captured on the array of capture oligonucleotides is then determined by fluorescent quantification as compared with known controls. In FIG. 8, such analysis of the array indicates ligation product sequences hybridizing to gene-specific addresses, where the fluorescent intensity represents amplification of the Her-2 gene, loss of heterozygosity of the p53 gene, and the control SOD gene, respectively.

Figure 10:
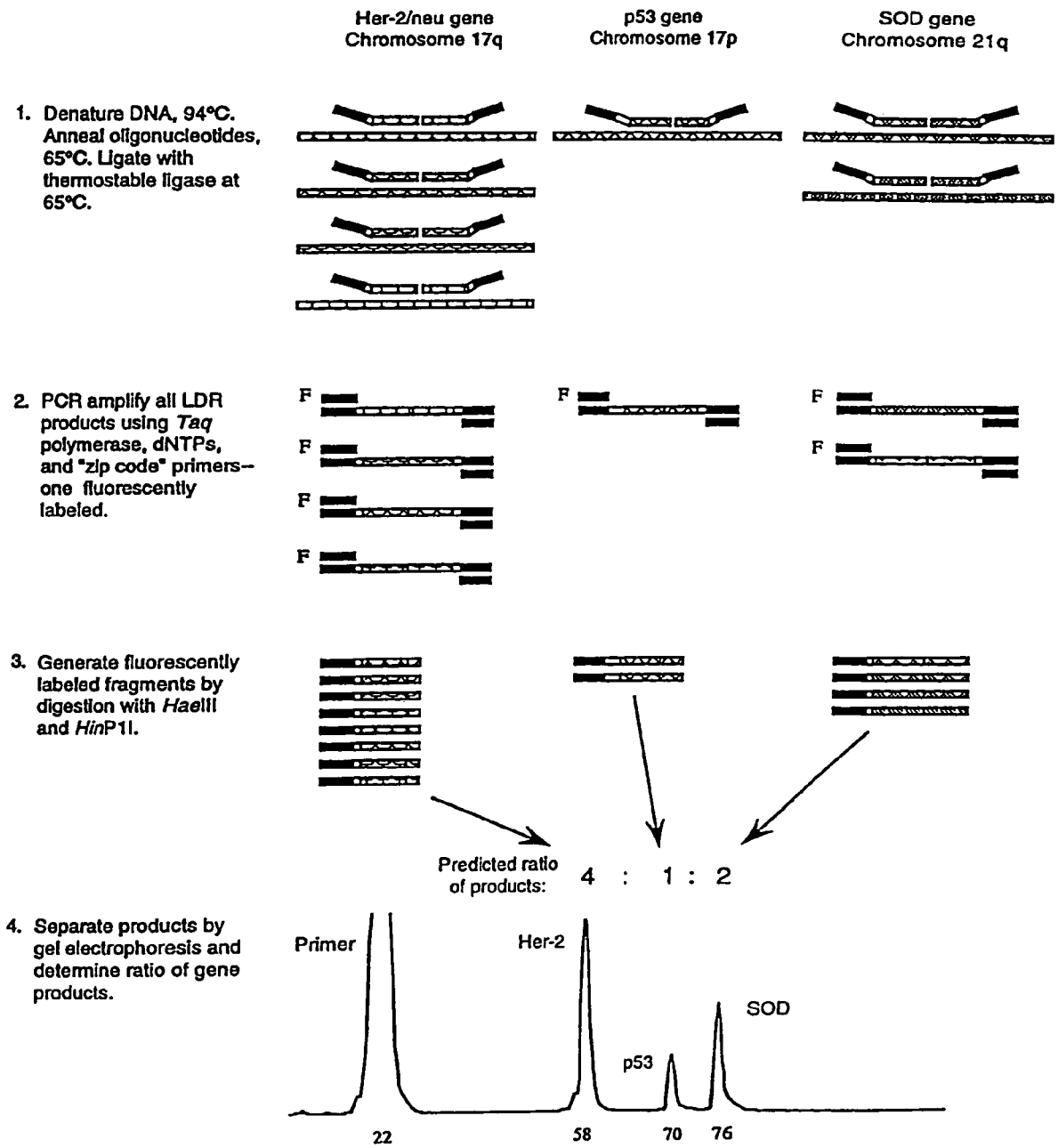
FIG. 10 is a schematic diagram depicting an LDR/PCR process for multiplex detection of gene amplifications and deletions.

FIG. 10 is a schematic diagram depicting an LDR/PCR process for multiplex detection of gene amplifications and deletions. Here, the ratio of the Her-2/neu gene from Chromosome 17q, the p53 gene from Chromosome 17p, and the SOD gene from Chromosome 21q is detected. Following denaturation of DNA at 94° C., pairs of oligonucleotide probes, having a target-specific portion and a primer-specific portion, are allowed to anneal adjacent to each other on target nucleic acids and ligate to one another (in the absence of mismatches). This ligase detection reaction is carried out with Tth ligase at a hybridization/ligation temperature of 65° C. which is well below the $T_m$ values of 75° C. for the oligonucleotide probes. Next, the ligation product sequences are simultaneously amplified by PCR using Taq polymerase and two common primers complementary to the primer-specific portion, one of which is fluorescently labeled. This maintains the proportionality of the target sequences initially present in the sample. The extension products are then digested with HaeIII and HinpII which releases fluorescently labeled fragments of unique sizes for each target sequence present in the sample. The digestion products are separated and analyzed on an Applied Biosystems, Inc. (Foster City, Calif.) 373A DNA Sequencer. The peak heights and areas are related to the relative copies of genes present in the initial target sample.

Figure 11:
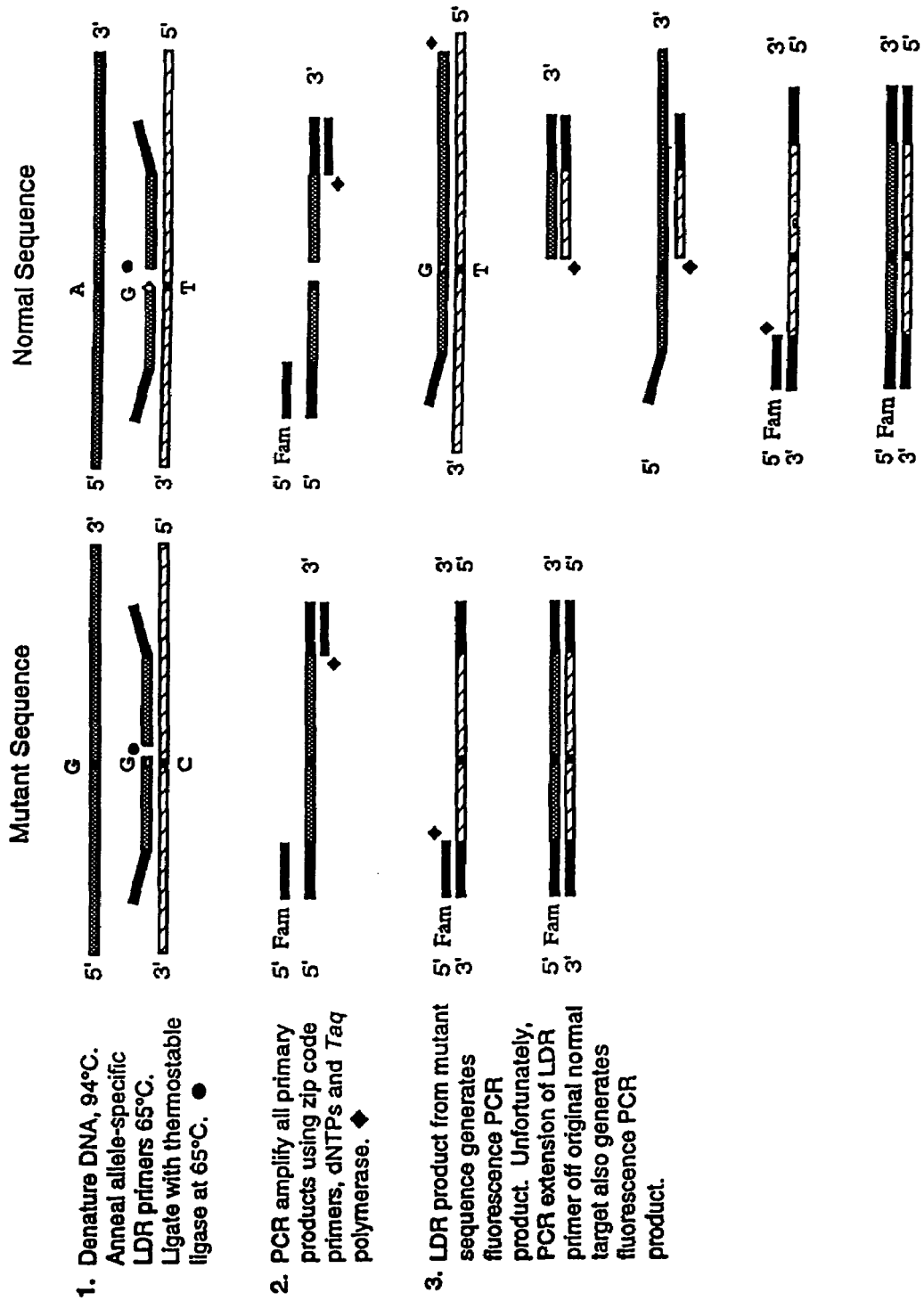
FIG. 11 is a schematic diagram depicting an allele specific problem for an LDR/PCR process.

FIG. 11 is a schematic diagram, depicting a problem which can be encountered with the allele-specific LDR/PCR process. While a PCR/LDR process is very powerful, there may be circumstances where a multiplexed allele-specific LDR/PCR process of the present invention would be preferred. The concept is to have one or more sets of LDR oligonucleotide probes, each set characterized by (a) a first oligonucleotide probe, having a target-specific portion and a 5' upstream primer-specific portion, and (b) a second oligonucleotide probe, having a target-specific portion and a 3' downstream primer-specific portion. As shown in step 1 of FIG. 11, the LDR oligonucleotide probes anneal adjacent to each other on the target sequence. An LDR reaction using thermostable ligase (black dot) would form a ligation product sequence provided there is perfect complementarity at the ligation junction. In step 2, the ligation product sequences are PCR amplified with primer sets, each set characterized by (a) an upstream primer containing the same sequence as the 5' upstream primer-specific portion of a ligation product sequence and (b) a downstream primer complementary to the 3' downstream primer-specific portion of that ligation product sequence. The primers are shown as black lines in step 2. If one primer is fluorescently labeled, it will generate a fluorescent product which may be detected in a variety of detection schemes. For the LDR/PCR process to be specific, a PCR extension product should not be formed in the absence of a ligation event. Unfortunately, the possibility exists for polymerase to extend the first LDR oligonucleotide probe (off normal target), forming a product containing the length of the target sequence, and a primer-specific portion on the 5' end. Meanwhile, polymerase can make several complementary copies of the downstream LDR probe using the downstream primer. In a second amplification cycle, this downstream LDR probe extension product can anneal to the upstream LDR probe extension product off the target sequence, and generate a sequence containing the target region flanked by the two primer-specific sequences. This product will amplify as the LDR product, and thus yield a false positive signal.

Figure 12:
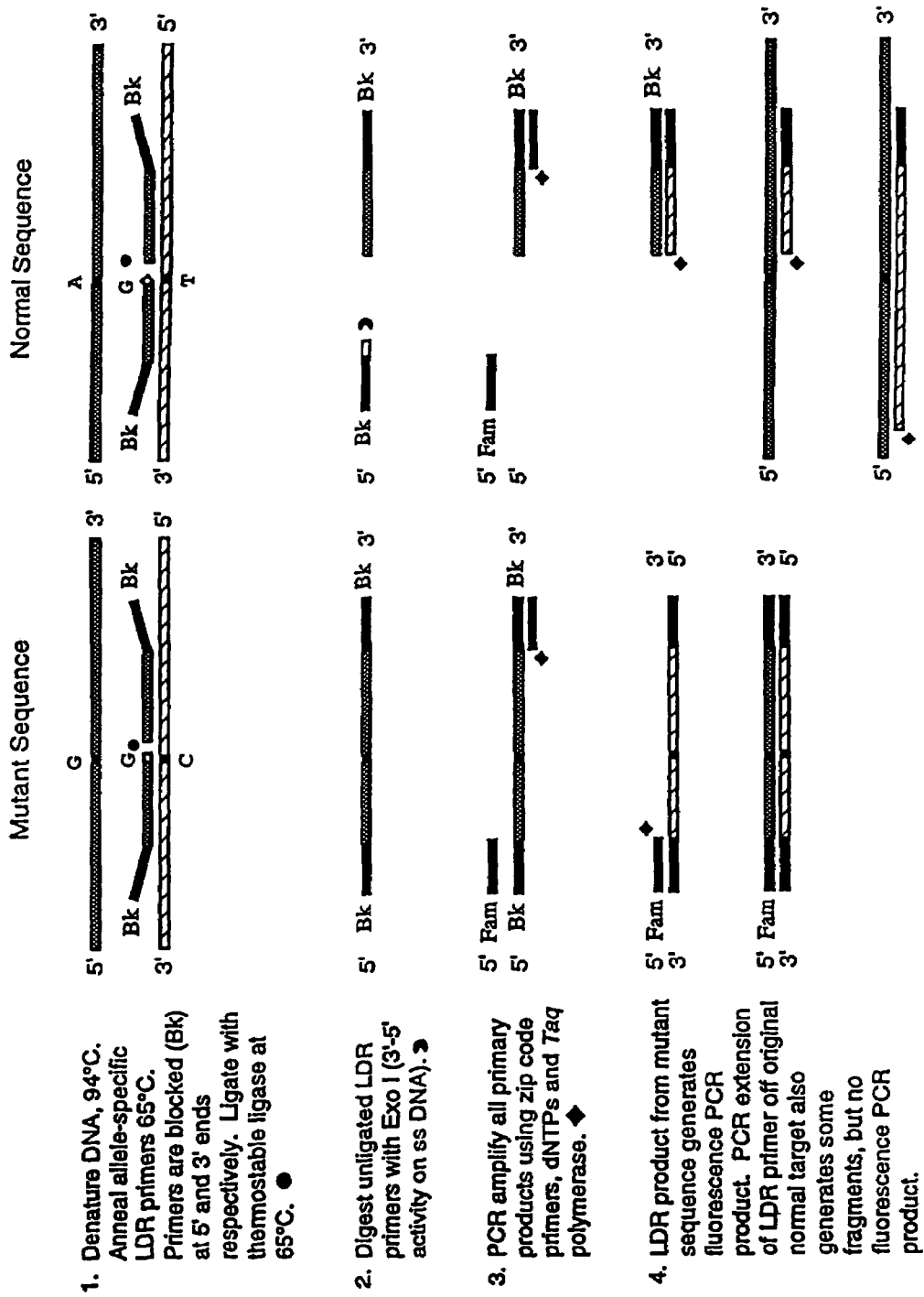
FIG. 12 is a schematic diagram depicting a solution for the allele specific problem for an LDR/PCR process which is shown in FIG. 11.

FIG. 12 is a schematic drawing showing a solution to the allele specific LDR/PCR problem, utilizing an intermediate exonuclease digestion step. Allele-specific LDR/PCR can be achieved while significantly reducing background ligation independent (incorrect) target amplification. To do so, it is necessary to eliminate one or more of the components required for ligation independent PCR amplification, without removing the information content of the ligation product sequence. One solution is to use exonuclease in step 2 to digest unreacted LDR oligonucleotide probes from step 1. By blocking the end which is not ligated, for example the 3' end of the downstream oligonucleotide probe, one probe can be made substantially resistant to digestion, while the other is sensitive. Only the presence of full length ligation product sequence will prevent digestion of the upstream primer. Blocking groups include use of a thiophosphate group and/or use of 2-O-methyl ribose sugar groups in the backbone. Exonucleases include Exo 1 (3'-5'), Exo III (3'-5'), and Exo IV (both 5'-3' and 3'-5'), the later requiring blocking on both sides. One convenient way to block both probes is by using one long "padlock" probe (see M. Nilsson et. al., "Padlock Probes: Circularizing Oligonucleotides for Localized DNA Detection," *Science* 265: 2085-88 (1994), which is hereby incorporated by reference), although this is by no means required. An advantage of using exonucleases for example a combination of Exo I (single strand specific) and Exo III (double strand specific), is the ability to destroy both target and one LDR probe, while leaving the ligation product sequences substantially undigested. By using an exonuclease treatment prior to PCR, in accordance with steps 3 and 4, either one or both oligonucleotide probes in each set are substantially reduced, and thus hybridization of the remaining oligonucleotide probes to the original target DNA (which is also substantially reduced by exonuclease treatment) and formation of a ligation product sequence which is a suitable substrate for PCR amplification by the oligonucleotide primer set is substantially reduced. In other words, formation of ligation independent labeled extension products is substantially reduced or eliminated.

Figure 13:
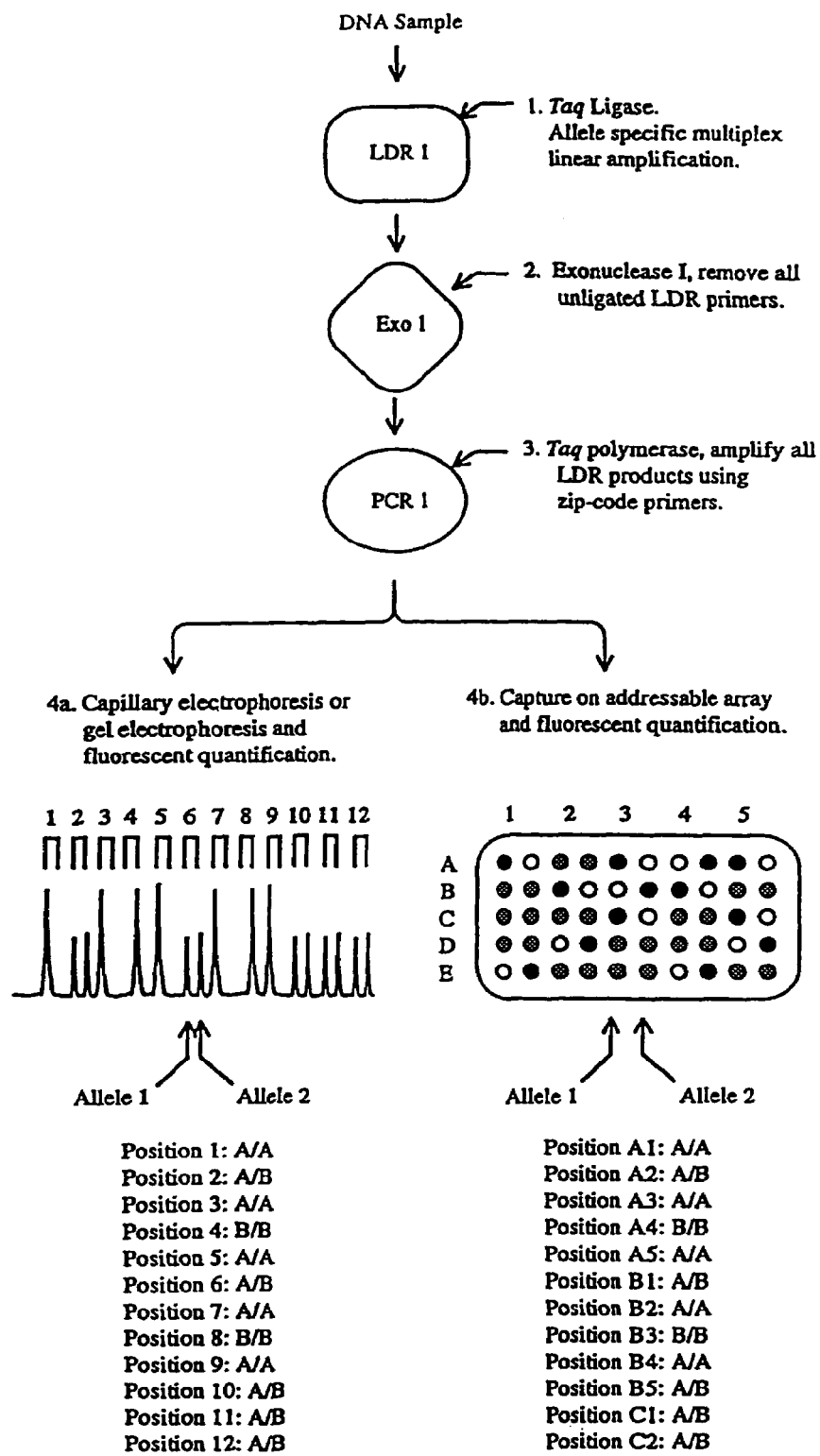
FIG. 13 is a flow diagram depicting an LDR/PCR process with an intermediate exonuclease digestion phase for detection of biallelic polymorphisms by electrophoresis or capture on an addressable array.

FIG. 13 is a flow diagram showing an allele-specific LDR/PCR process using exonuclease digestion with either size based- or DNA array based-detection. The flow diagram shows the three reactions required for the multiplexed allele-specific LDR/PCR process. In step 1, sets of LDR oligonucleotide probes (wherein the downstream probes are blocked on their 3' ends) are ligated in the presence of the correct allele target using Taq DNA ligase. Unreacted upstream probes are digested with exonuclease in step 2, coincidentally, target is also digested. Finally, in step 3, primer sets are used to amplify the ligation product sequence by hybridizing to the primer specific portions of ligation product sequences. In step 4a, the LDR oligonucleotide probes in a given particular set generate a unique length product, and thus may be distinguished from either oligonucleotide probes or other ligation products. After the PCR reaction, the products are separated by size or electrophoretic mobility. Labels on the PCR primers are detected, and the products are distinguished by size. In step 4b, the LDR oligonucleotide probes in a particular set use may be distinguished from either oligonucleotide probes or other ligation product sequences by differences in the sequences of the PCR primers. By using a plurality of oligonucleotide primer sets, each set characterized by (a) an upstream primer containing the same sequence as the 5' upstream primer-specific portion of a ligation product sequence, and (b) a downstream primer complementary to the 3' downstream primer-specific portion of that ligation product sequence, wherein one primer has a detectable reporter label and the other primer contains an addressable nucleotide sequence linked to the 5' end of that primer such that the addressable nucleotide sequence remains single stranded after a PCR reaction, all the products can be distinguished. The latter may be achieved by using a non-natural base within a PCR primer which polymerase cannot extend through, thus generating PCR products which have single stranded tails. See C. Newton, et. al., "The Production of PCR Products with 5' Single-stranded Tails Using Primers that Incorporate Novel Phosphoramidite Intermediates," *Nucl. Acids Res.* 21(3): 1155-62 (1993), which is hereby incorporated by reference. By providing a DNA array with different capture oligonucleotides immobilized at different particular sites, where the capture oligonucleotides have nucleotide sequences complementary to the addressable nucleotide sequences on the primers, the PCR extension products can hybridize to the DNA array. Finally, the labels of extension product sequences captured using the addressable array-specific portions immobilized to the DNA array at particular sites can be detected. This indicates the presence of one or more target nucleotide sequences in the sample.

Figure 14:
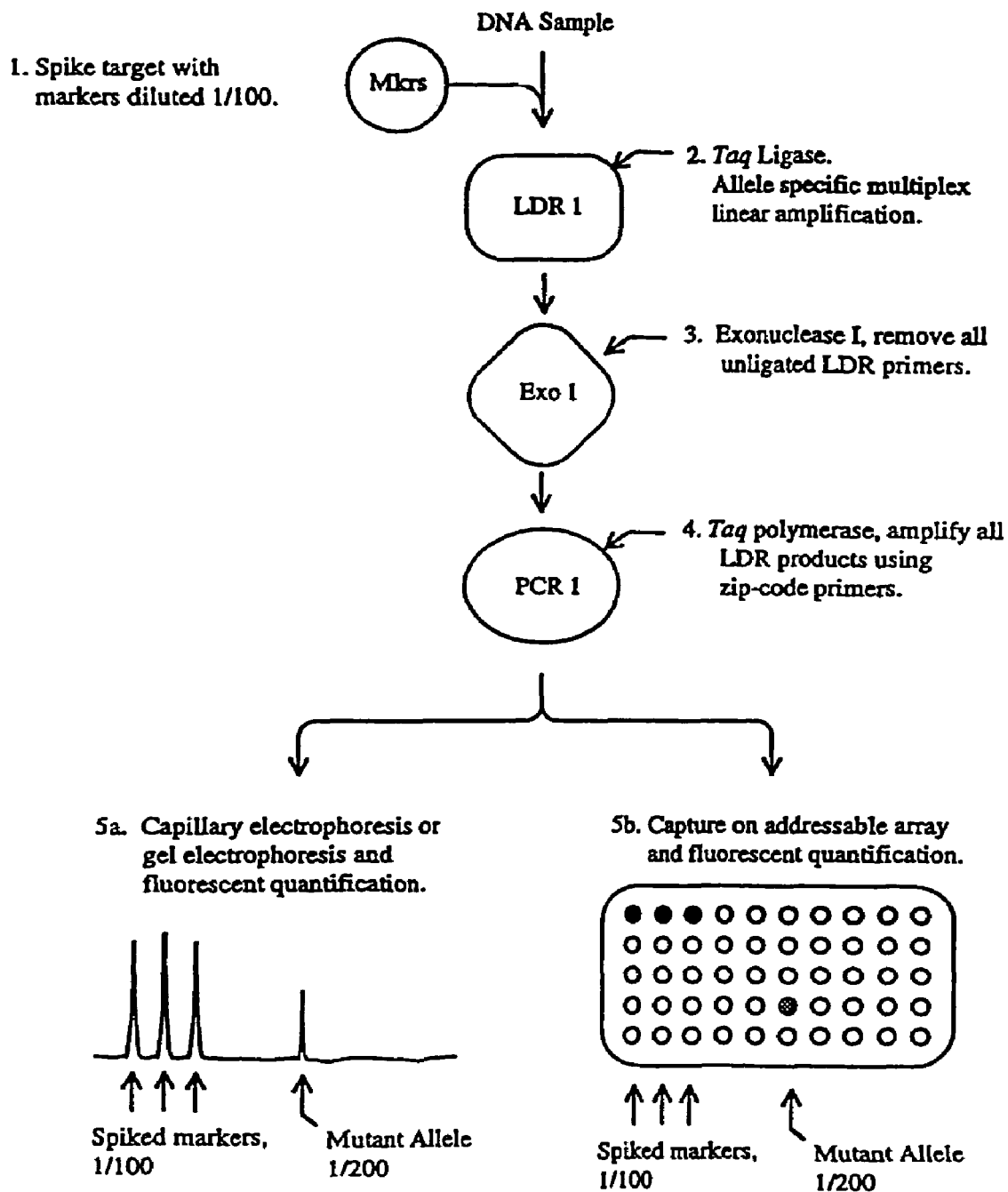
FIG. 14 is a flow diagram depicting an LDR/PCR process with an intermediate exonuclease digestion phase for detection of cancer-associated mutations by electrophoresis or capture on an addressable array.

FIG. 14 is a flow diagram showing a quantitative allele-specific LDR/PCR process using exonuclease digestion in step 3 with either size based- or DNA array based-detection. The flow diagram shows how one can quantify the amounts of different targets (especially low abundance cancer mutations) by adding marker sequence(s) (step 1) at the start of the LDR reaction (step 2). In this embodiment, the biochemical reactions (i.e. PCR (step 4)) are followed, as described in FIG. 13, and the relative amount of mutant product to marker product are quantified using capillary or gel electrophoresis (step 5a) or capture on an addressable array (step 5b). The amount of mutant target present in the original sample can then be determined.

Figure 15:
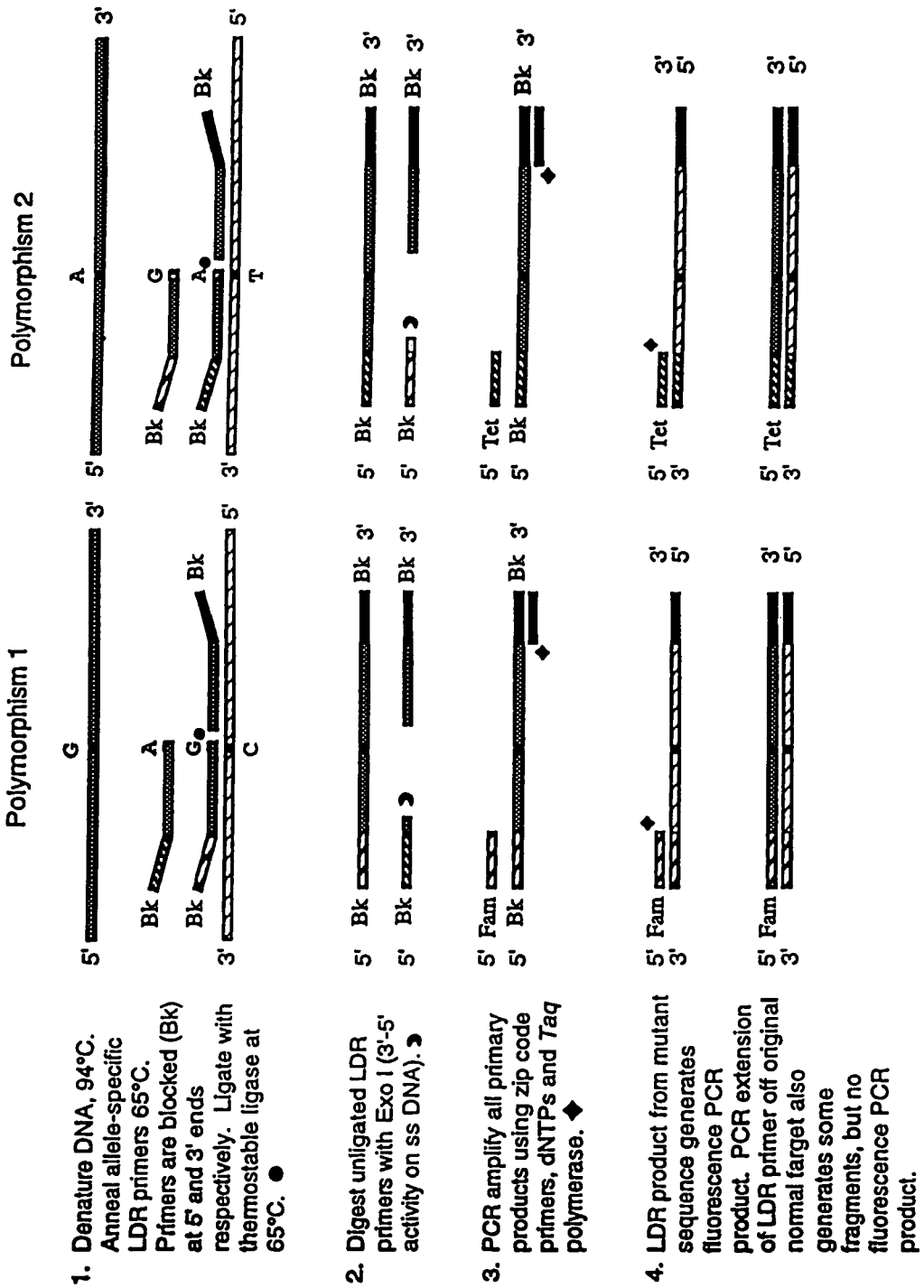
FIG. 15 is a schematic diagram depicting an LDR/PCR process with an intermediate exonuclease digestion phase for detection of allele specific mutations and polymorphisms.

FIG. 15 is a schematic drawing showing an allele-specific LDR/PCR process with exonuclease digestion (step 2) for detection of mutations or polymorphisms. Mutations and polymorphisms may be distinguished as described in FIG. 12. In this example, in step 1, the upstream LDR oligonucleotide probes, which have the discriminating allele-specific base at the 3' end of the target-specific portion, have different 5' upstream primer-specific portions. Thus, different primers (in the PCR amplification step (i.e. step 3)) may be labeled with different fluorescent groups (Fam and Tet) to allow for distinction of products (step 4). An array based detection scheme may also be used, where the upstream (allele-specific) probes have different 5' upstream primer-specific portions, and the different PCR primers contain different addressable nucleotide sequences which remain single stranded after a PCR reaction.

Figure 16:
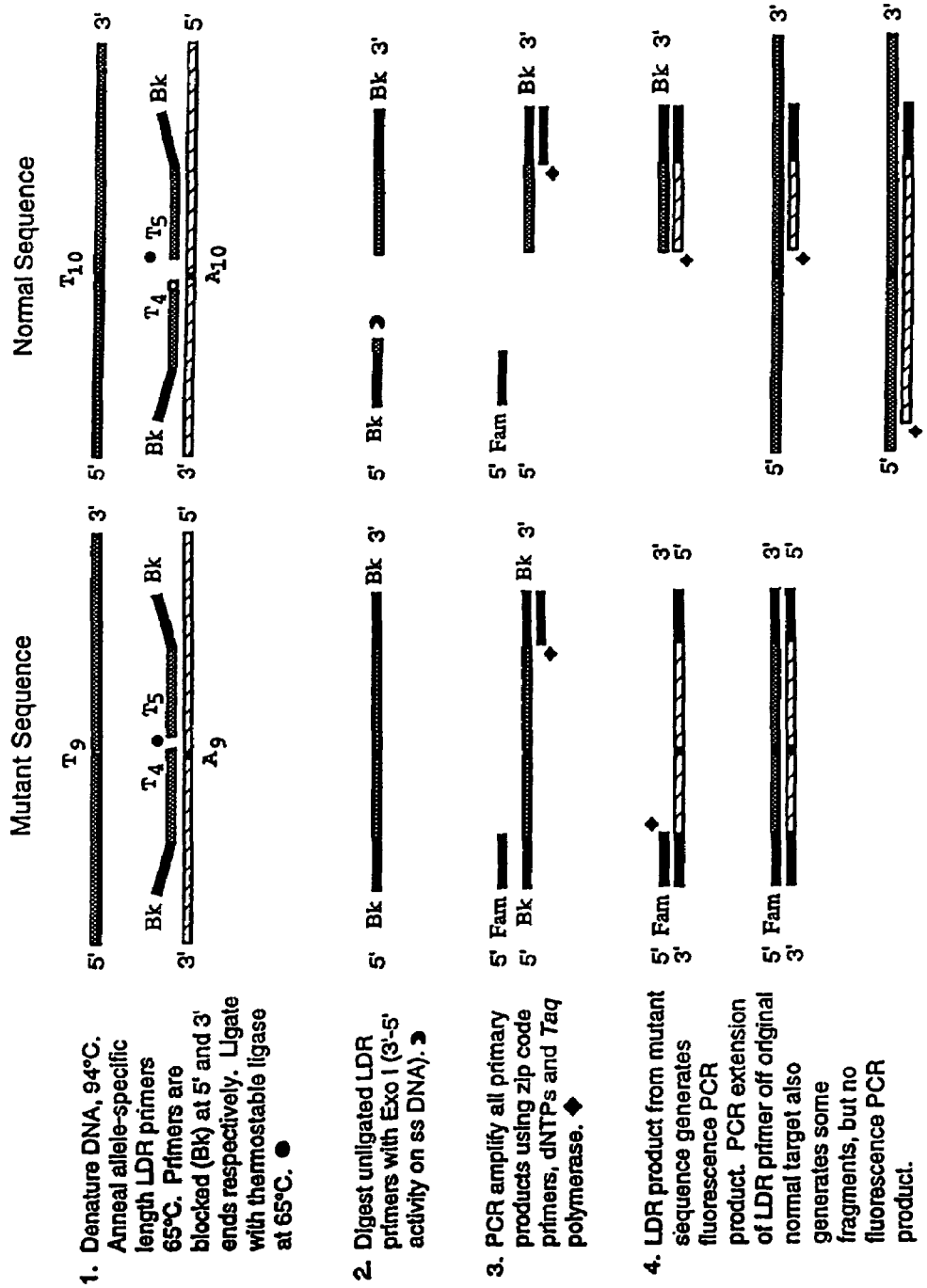
FIG. 16 is a schematic diagram depicting an LDR/PCR process with an intermediate exonuclease digestion phase for detection of mononucleotide repeat polymorphisms.

FIG. 16 is a schematic drawing showing an allele-specific LDR (step 1)/PCR (step 3) process using exonuclease digestion (step 2) for detection of mononucleotide or dinucleotide repeat polymorphisms. One of the most powerful uses of LDR/PCR is for detecting nucleotide repeat polymorphisms, a task which cannot be achieved by allele-specific PCR (because the 3' nucleotide is always the same), nor easily achieved by observing PCR product size variation (due to Taq polymerase slippage during amplification). In FIG. 16, the LDR oligonucleotide probes distinguish between an $A_9$ and $A_{10}$ mononucleotide repeat sequence by virtue of the specificity of thermostable DNA ligase. LDR products are only formed on the correct length target sequence, and thus the presence of that target is distinguished (step 4).

Figure 17:
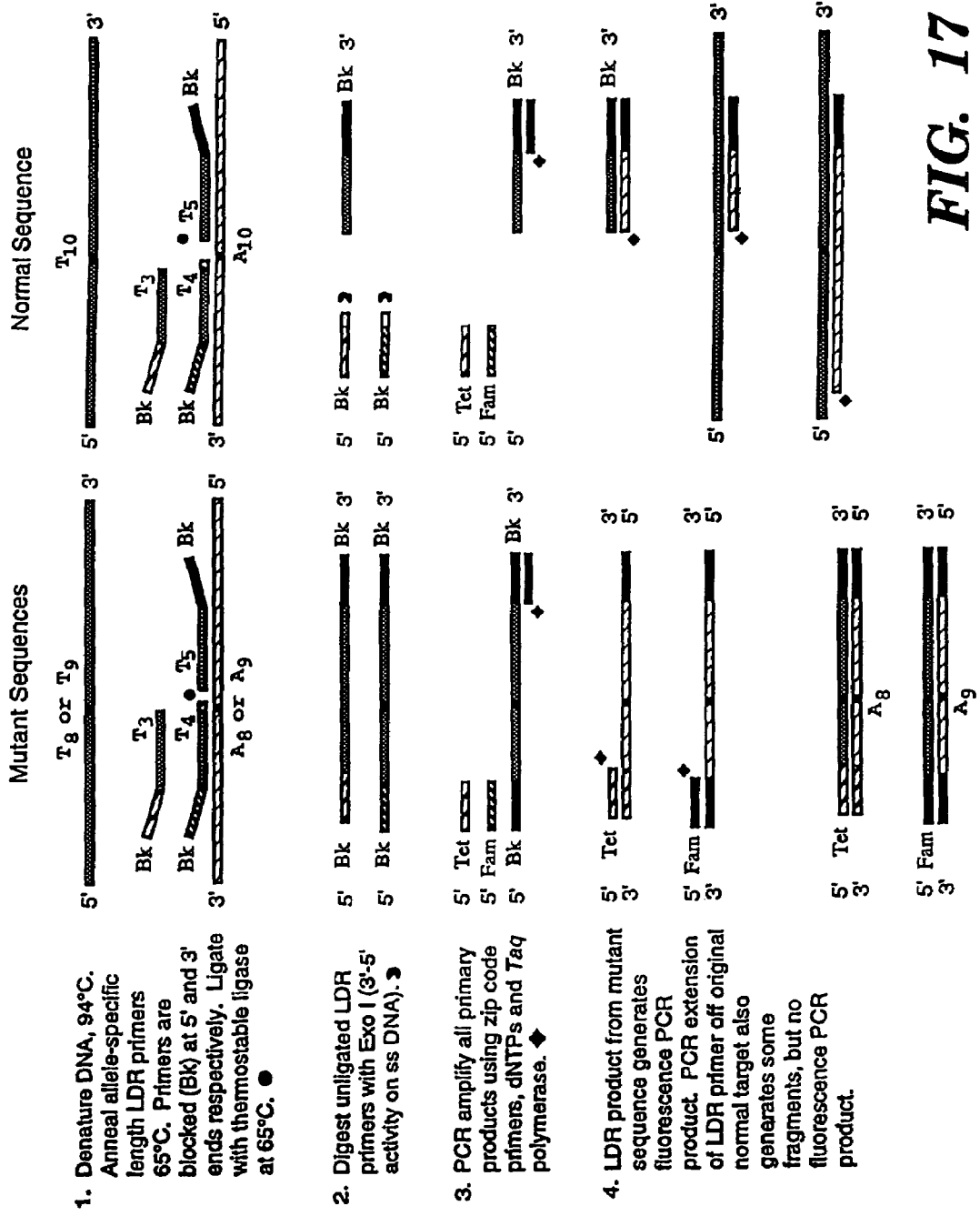
FIG. 17 is a schematic diagram depicting an LDR/PCR process with an intermediate exonuclease digestion phase for detection of mononucleotide repeat polymorphisms which are in low abundance.

FIG. 17 is schematic drawing showing an allele-specific LDR/PCR process using exonuclease digestion (step 2) for detection of low abundance mononucleotide or dinucleotide repeat mutations. Mononucleotide repeat length mutations may be distinguished as described in FIG. 12. In FIG. 17, the LDR oligonucleotide probes (step 1) distinguish between an $A_8$, $A_9$ (mutants), and $A_{10}$ (normal) mononucleotide repeat sequences by virtue of the specificity of thermostable DNA ligase. The two upstream LDR oligonucleotide probes differ in the length of the mononucleotide sequence at their 3' ends of their target specific portion and have different 5' upstream primer-specific portions. Thus, different primers (in the PCR amplification step (step 3)) may be labeled with different fluorescent groups (Fam and Tet) to allow for distinction of products (step 4). This has the distinct advantage of allowing mononucleotide repeat polymorphisms to be distinguished based on fluorescent label instead of size, the latter being susceptible to false positives due to polymerase slippage. An array based detection scheme may also be used, where the upstream (allele-specific) probes have different 5' upstream primer-specific portions, and the different PCR primers contain different addressable nucleotide sequences which remain single stranded after a PCR reaction.

Figure 18:
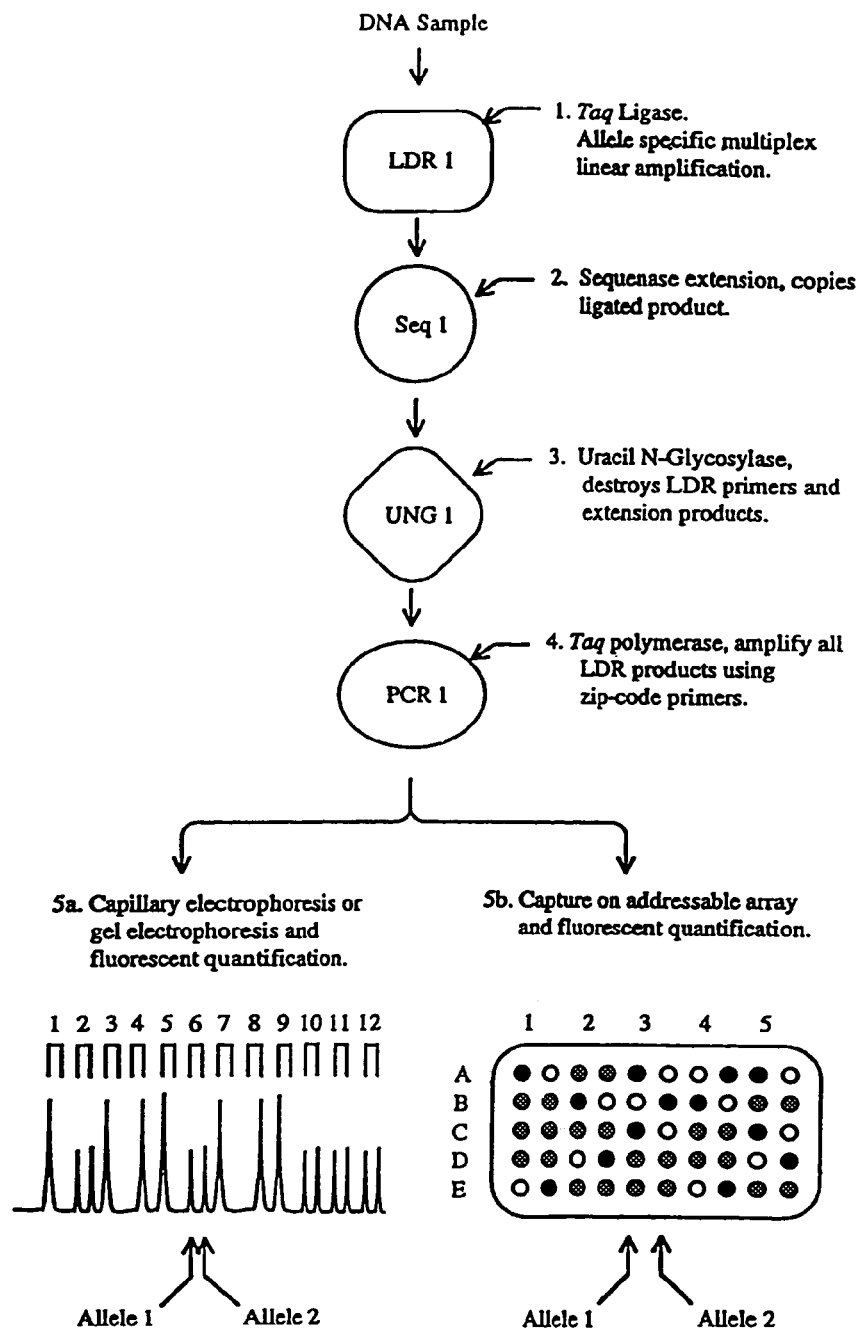
FIG. 18 is a flow diagram depicting the detection of polymorphisms using an LDR/PCR process with an intermediate sequenase extension phase and a uracil N-glycosylase digestion phase after the LDR phase and before the PCR phase and with detection by electrophoresis or an addressable array.

FIG. 18 is a flow diagram, showing an allele-specific LDR/PCR process using uracil. N-glycosylase selection with either size based- or DNA array based-detection. The flow diagram shows the four reactions required for multiplexed allele-specific LDR/PCR. Sets of LDR oligonucleotide probes (wherein one or both probes contain deoxyuracil in place of deoxythimidine) are ligated in the presence of the correct allele target using Taq DNA ligase in step 1. A complementary copy of the ligation product sequence is made with sequenase in step 2. Sequenase is a modified T7 polymerase, with any easily inactivated polymerase (i.e. mesophilic polymerases such as, *E. coli* polymerase) being useful. Both ligation product sequences and unreacted probes are destroyed with uracil N-glycosylase in step 3. The advantage of using uracil N-glycosylase is its proven ability in carry-over prevention for PCR. Finally PCR primer sets are used to amplify the sequenase extension products in step 4. In step 5a, the LDR oligonucleotide probes in a particular set generate a unique length product, and thus may be distinguished from either probes or other ligation products. After the PCR reaction, the products are separated by size or electrophoretic mobility. Labels on the PCR primers are detected, and products are distinguished by size. In step 5b, the LDR oligonucleotide probes in a particular set may be distinguished from either probes or other ligation product sequences by differences in the sequences of the primer-specific portions. By using a plurality of oligonucleotide primer sets, each set characterized by (a) an upstream primer containing the same sequence as the 5' upstream primer-specific portion of a ligation product sequence, and (b) a downstream primer complementary to the 3' downstream primer-specific portion of that ligation product sequence. One primer has a detectable reporter label, and the other primer contains an addressable array-specific portion linked to the 5' end of that primer such that the addressable array-specific portion remains single stranded after a PCR reaction, one can distinguish all the products. By providing a DNA array with different capture oligonucleotides immobilized at different particular sites, wherein the capture oligonucleotides have nucleotide sequences complementary to the addressable array-specific portions on the primers, the PCR extension products can be hybridized to the DNA array. Finally, the labels of extension product sequences captured using the addressable nucleotide sequence portions and immobilized to the DNA array at particular sites can be detected to indicate the presence of one or more target nucleotide sequences in the sample.

Figure 19:
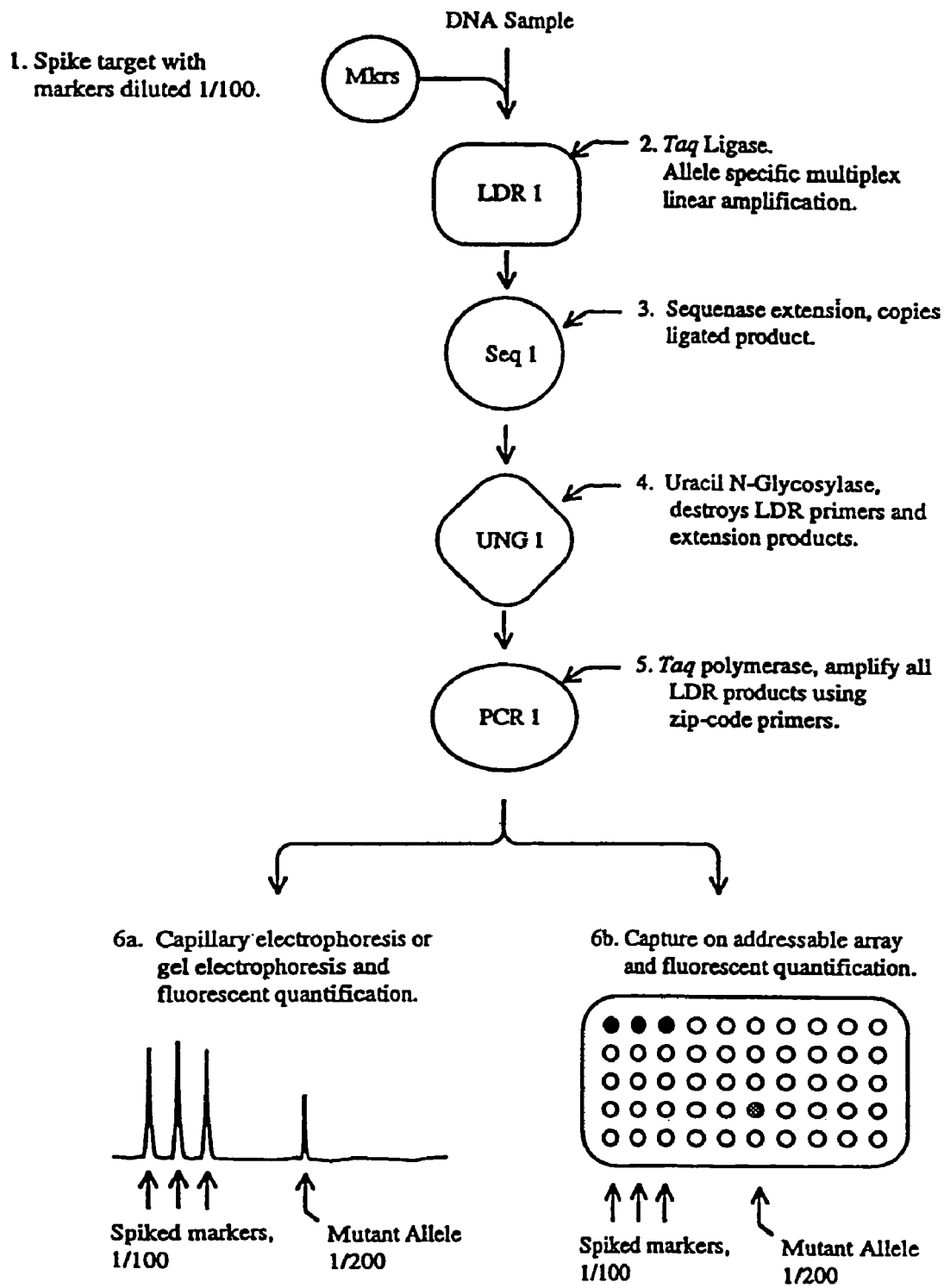
FIG. 19 is a flow diagram depicting the detection of cancer using an LDR/PCR process with an intermediate sequenase extension phase and a uracil N-glycosylase digestion phase after the LDR phase and before the PCR phase and with detection by electrophoresis or an addressable array.

FIG. 19 is a flow diagram showing a quantitative allele-specific LDR/PCR process using uracil N-glycosylase selection with either size based- or DNA array based-detection. The flow diagram shows how one can quantify the amounts of different targets (especially low abundance cancer mutations) by adding marker sequence(s) in step 1 at the start of the LDR phase in step 2. As described in FIG. 18, the biochemical reactions (i.e. sequenase treatment (step 3), uracil N-glycosylase selection (step 4), and PCR (step 5)) are preceded with, and the relative amount of mutant product to marker product is quantified using capillary or gel electrophoresis (step 6a) or capture on an addressable array (step 6b). From this information, the amount of mutant target present in the original sample can be determined.

Figure 20:
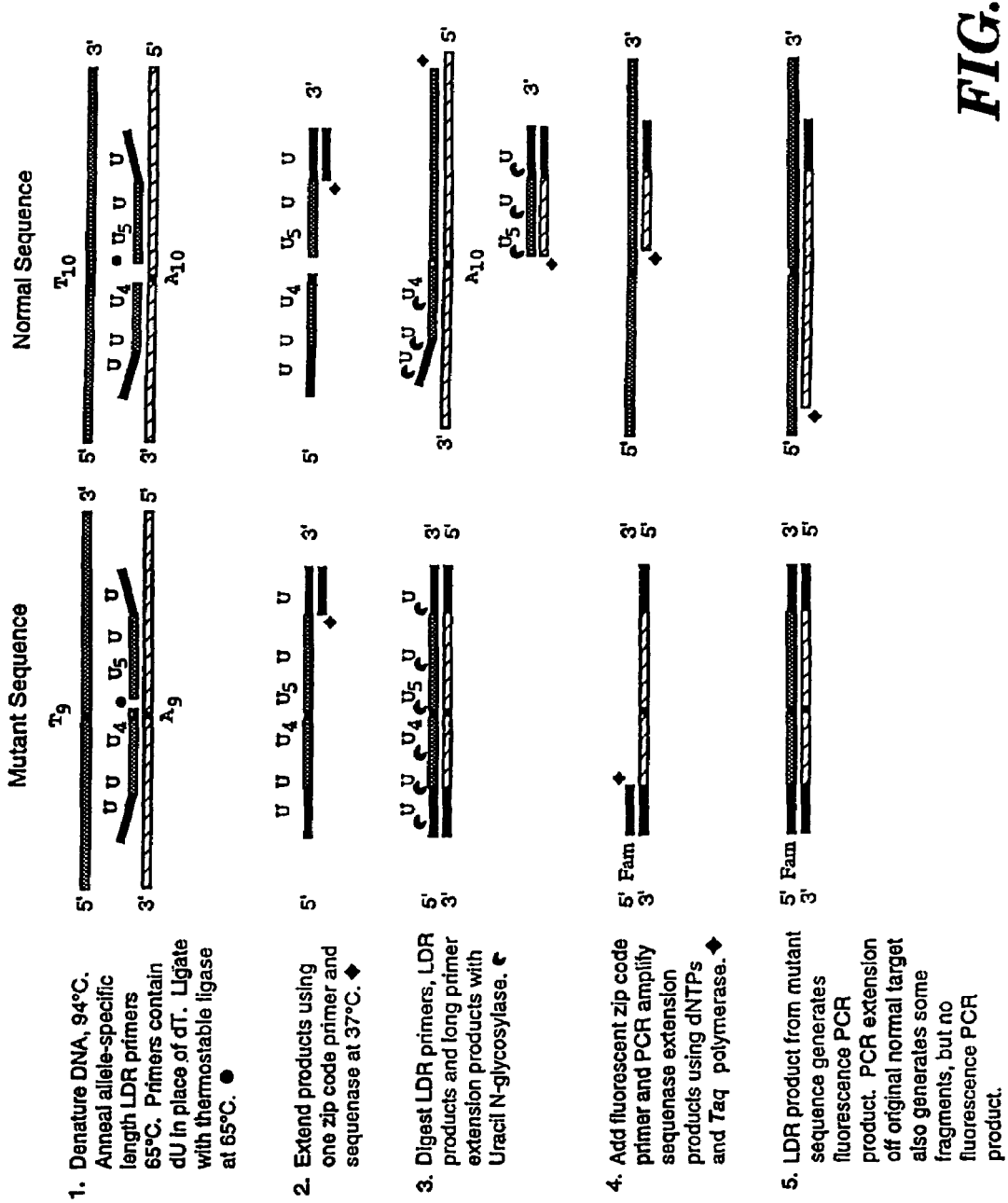
FIG. 20 is a schematic diagram depicting detection of mononucleotide repeats using an LDR/PCR process with an intermediate sequenase amplification phase and a uracil N-glycosylase digestion phase after the LDR phase and before the PCR phase.

FIG. 20 is a schematic drawing showing an allele-specific LDR/PCR process using uracil N-glycosylase selection (step 3) (after sequenase treatment (step 2)) for detection of mononucleotide or dinucleotide repeat polymorphisms. One of the most powerful uses of the LDR/PCR process is for detecting nucleotide repeat polymorphisms, a task which cannot be achieved by allele-specific PCR (since the 3' nucleotide is always the same), nor easily achieved by observing PCR product size variation (due to Taq polymerase slippage during amplification), as in step 4. In FIG. 20, the LDR (step 1) oligonucleotide probes distinguish between an $A_9$ and $A_{10}$ mononucleotide repeat sequence by virtue of the specificity of thermostable DNA ligase. Ligation product sequences are only formed on the correct length target sequence, and, thus, the presence of that target is distinguished in step 5.

Figure 21:
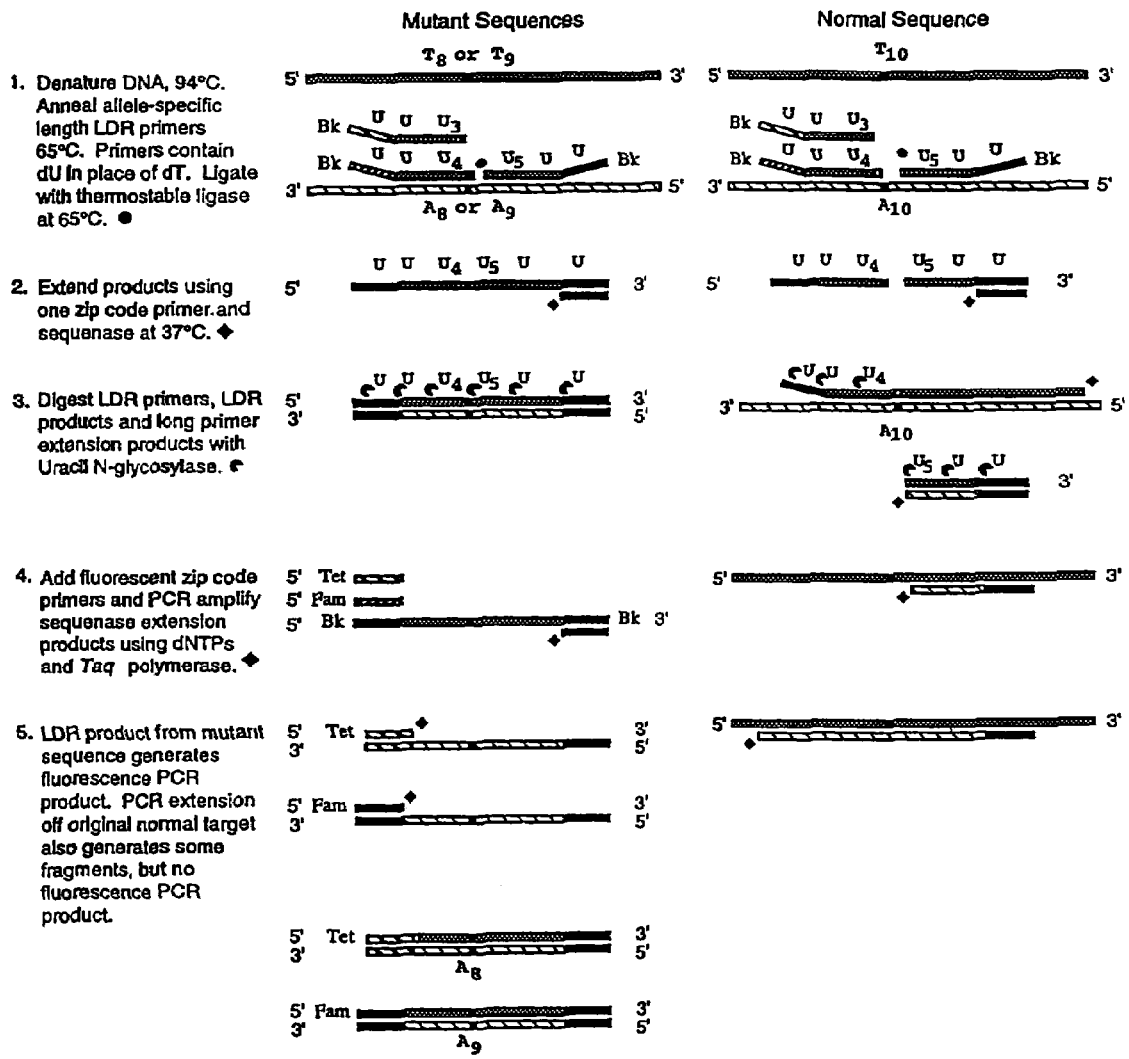
FIG. 21 is a schematic diagram depicting detection of mononucleotide repeat polymorphisms which are in low abundance using an LDR/PCR process with an intermediate sequenase amplification phase and a uracil N-glycosylase digestion phase after the LDR phase and before the PCR phase.

FIG. 21 is a schematic drawing showing an allele-specific LDR/PCR process using uracil N-glycosylase selection for detection of low abundance mononucleotide or dinucleotide repeat mutations. Mononucleotide repeat length mutations may be distinguished as described in FIG. 18. In FIG. 21, the LDR oligonucleotide probes distinguish between an $A_8$, $A_9$ (mutants), and $A_{10}$ (normal) mononucleotide repeat sequences by virtue of the specificity of thermostable DNA ligase (step 1). Sequenase treatment (step 2) and uracil N-glycosylase selection (step 3) are then carried out. The two upstream LDR oligonucleotide probes differ in the length of the mononucleotide sequence at the 3' ends of their target-specific portion, and have different 5' upstream primer-specific portions. Thus, different primers (in the PCR amplification step (steps 4-5)) may be labeled with different fluorescent groups (Fam and Tet) to allow for distinction of products. This has the distinct advantage of allowing one to distinguish mononucleotide repeat polymorphisms based on fluorescent label instead of size, the latter being susceptible to false positives due to polymerase slippage. An array based detection scheme may also be used, where the upstream (allele-specific) probes have different 5' upstream primer-specific portions, and the different PCR primers contain different addressable array-specific portions which remain single stranded after a PCR reaction.

The LDR/exonuclease/PCR process described with reference to FIGS. 11 to 17 and the LDR/sequenase/uracil N-glycosylase/PCR process set forth in FIGS. 18-21 provide the ability to multiplex detect and then PCR amplify many different target sequences and to distinguish multiple single-base or sequence variations, all in a single reaction tube. This is achieved by combining the sensitivity of PCR with the selectivity of LDR. Since the selection of mutant sequences is mediated by LDR rather than PCR, the primary PCR/secondary PCR/LDR process is less susceptible to false-positive signal generation. In addition, the primary PCR/secondary PCR/LDR process allows detection of closely-clustered mutations, detection of single base or small insertions and deletions in small repeat sequences, quantitative detection of less than 1% mutations in high background of normal DNA, and detection of ligation product sequences using addressable arrays. Detection of single base or small insertions and deletions in small and medium repeat sequences may cause "stutter" when the primary amplification is PCR. No other currently-available technique can adequately solve this problem, especially when the target sequence containing the mononucleotide repeat polymorphism is present in a lower abundance than normal DNA. In fact, analysis of genomic mutations which involve repeat sequence changes is severely hampered by the PCR "stutter" problem. By using the LDR/PCR process of the present invention, it is possible to detect down to 1% mutations in a high background of normal DNA. The only relatively minor challenges presented by this process are that the mutations must be known and that 3 different enzymes/reaction conditions must be utilized.

III. Primary PCR/Secondary PCR Process

A third aspect of the present invention also involves a method for identifying two or more of a plurality of sequences differing by one or more single-base changes, insertions, deletions, or translocations in one or more target nucleotide sequences. This method involves subjecting a sample potentially containing one or more target nucleotide sequences with a plurality of sequence differences to two successive polymerase chain reaction phases.

For the first polymerase chain reaction phase, one or more primary oligonucleotide primer groups are provided where each group comprises one or more primary oligonucleotide primer sets. Each set has a first oligonucleotide primer, having a target-specific portion and a 5' upstream secondary primary-specific portion, and a second oligonucleotide primer, having a target-specific portion and a 5' upstream secondary primer-specific portion. The first oligonucleotide primers of each set in the same group contain the same 5' upstream secondary primer-specific portion and the second oligonucleotide primers of each set in the same group contain the same 5' upstream secondary primer-specific portion. The oligonucleotide primers in a particular set are suitable for hybridization on complementary strands of a corresponding target nucleotide sequence to permit formation of a polymerase chain reaction product. However, there is a mismatch which interferes with formation of such a polymerase chain reaction product when the primary oligonucleotide primers hybridize to any other nucleotide sequence present in the sample. The polymerase chain reaction products in a particular set may be distinguished from other polymerase chain reaction products with the same group or other groups. The primary oligonucleotide primers are blended with the sample and the polymerase to form a primary polymerase chain reaction mixture.

The primary polymerase chain reaction mixture is subjected to two or more polymerase chain reaction cycles involving a denaturation treatment, a hybridization treatment, and an extension treatment, as described above. During the hybridization treatment, the target-specific portion of a primary oligonucleotide primer is hybridized to the target nucleotide sequences. In the extension treatment, the hybridized primary oligonucleotide primers are extended to form primary extension products complementary to the target nucleotide sequence to which the primary oligonucleotide primer is hybridized.

Although the upstream secondary primer-specific portions of a primary oligonucleotide primer set are not present on the target DNA, their sequences are copied by the second and subsequent cycles of the primary polymerase chain reaction phase. As a result, the primary extension products produced after the second cycle have the secondary primer-specific portions on their 5' ends and the complement of primer-specific portion on their 3' ends.

In the second polymerase chain reaction phase of this aspect of the present invention, one or a plurality of secondary oligonucleotide primer sets are provided. Each set has a first secondary primer having a detectable reporter label and containing the same sequence as the 5' upstream portion of a first primary oligonucleotide primer, and a second secondary primer containing the same sequence as the 5' upstream primer of the second primary oligonucleotide primer from the same primary oligonucleotide primer set as the first primary oligonucleotide complementary to the first secondary primer. A set of secondary oligonucleotide primers amplify the primary extension products in a given group. The secondary oligonucleotide primers are blended with the primary extension products and the polymerase to form a secondary polymerase chain reaction mixture.

The secondary polymerase chain reaction mixture is subjected to one or more polymerase chain reaction cycles involving a denaturation treatment, a hybridization treatment, and an extension treatment, as described above. In the hybridization treatment, the secondary oligonucleotide primers are hybridized to the primary extension products, while the extension treatment causes the hybridized secondary oligonucleotide primers to be extended to form secondary extension products complementary to the primary extension products. After subjecting the secondary polymerase chain reaction mixture to the two or more polymerase chain reaction cycles, the labelled secondary extension products are detected. This indicates the presence of one or more target nucleotide sequences in the sample.

Figure 22:
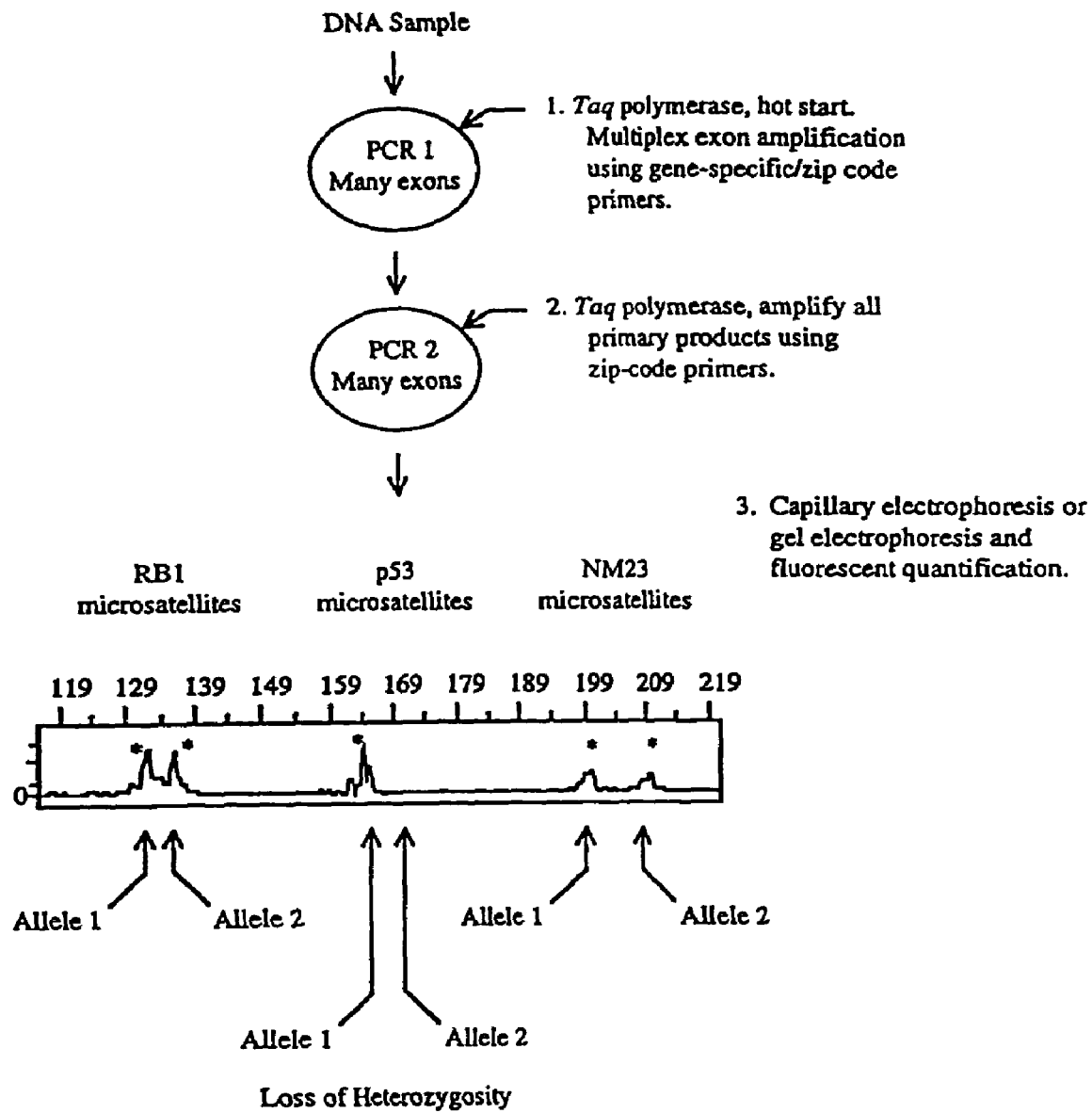
FIG. 22 is a flow diagram depicting a primary PCR/secondary PCR process for detection of microsatellite repeats.

FIG. 22 is a flow diagram depicting a primary PCR/secondary PCR process, in accordance with the present invention, for detection of microsatellite repeats. In step 1 (i.e. the primary PCR phase), after DNA sample preparation, multiple exons are amplified using Taq polymerase under hot start conditions with oligonucleotide primers having a target-specific portion and a secondary primer-specific portion. step 2 involves a secondary PCR phase where Taq polymerase is used to amplify the primary PCR extension products with oligonucleotide primers containing the same sequence as the secondary primer-specific portion of the primary PCR primers. The extension products resulting from the secondary PCR phase are subjected in step 3 to capillary electrophoresis or gel electrophoresis, followed by fluorescent quantification. The electrophoresis results in FIG. 22 indicate the presence of both alleles (i.e., chromosomes) containing RB1 and NM23 and loss of heterozygosity (i.e., loss of allele on one chromosome) for p53.

FIG. 23 is a schematic diagram depicting a primary PCR/secondary PCR process, according to the present invention, for detection of the loss of heterozygosity due to insertions and deletions in microsatellite repeats. The primary PCR phase in step 1 is initiated by denaturing the sample DNA at 94° C. Long PCR oligonucleotide primers, having 3' ends complementary to unique DNA surrounding microsatellite repeat sequences and 5' ends containing the same sequence as one of two primers utilized in the secondary PCR phase, are then caused to anneal to target DNA at 65° C. The primary PCR phase is carried out for 10-15 cycles. The long primers utilized in the primary PCR phase can be multiplexed as long as they do not amplify alleles with overlapping length ranges. These reactions must be carried out on tumor and corresponding normal DNA to identify informative (i.e heterozygous) loci. In step 2 (i.e secondary PCR amplification), primers complementary to the 5' ends of the primary PCR primers (one fluorescently labeled) are then used to amplify the primary PCR extension products at nearly equal efficiency. The secondary PCR extension products are then separated and analyzed by gel electrophoresis and an Applied Biosystems Inc. 373A DNA Sequencer using the Genescan 672 software package. Areas of loss of heterozygosity at informative loci are identified. The analysis in FIG. 23 shows the presence of both alleles (i.e., chromosomes) containing RB1 and NM23 and loss of heterozygosity (i.e., loss of allele on one chromosome) for p53.

IV. General Process Information

The ligase detection reaction is described generally in WO 90/17239 to Barany et al., F. Barany et al., "Cloning, Overexpression and Nucleotide Sequence of a Thermostable DNA Ligase-encoding Gene," *Gene* 109:1-11 (1991), and F. Barany, "Genetic Disease Detection and DNA Amplification Using Cloned Thermostable Ligase," *Proc. Natl. Acad. Sci. USA*, 88:189-193 (1991), the disclosures of which are hereby incorporated by reference. In accordance with the present invention, the ligase detection reaction can use 2 sets of complementary oligonucleotides. This is known as the ligase chain reaction which is described in the 3 immediately preceding references, which are hereby incorporated by reference. Alternatively, the ligase detection reaction can involve a single cycle which is known as the oligonucleotide ligation assay. See Landegren, et al., "A Ligase-Mediated Gene Detection Technique," *Science* 241:1077-80 (1988); Landegren, et al.; "DNA Diagnostics—Molecular Techniques and Automation," *Science* 242:229-37 (1988); and U.S. Pat. No. 4,988,617 to Landegren, et al., which are hereby incorporated by reference During ligase detection reaction phases, the denaturation treatment is carried out at a temperature of 80-105° C., while hybridization takes place at 50-85° C. Each cycle comprises a denaturation treatment and a thermal hybridization treatment which in total is from about one to five minutes long. Typically, the ligation detection reaction involves repeatedly denaturing and hybridizing for 2 to 50 cycles. The total time for the ligase detection reaction phase is 1 to 250 minutes.

The oligonucleotide probe sets or primers can be in the form of ribonucleotides, deoxynucleotides, modified ribonucleotides, modified deoxyribonucleotides, modified phosphate-sugar-backbone oligonucleotides, nucleotide analogs, and mixtures thereof.

In one variation, the oligonucleotides of the oligonucleotide probe sets each have a hybridization or melting temperature (i.e. $T_m$) of 66-70° C. These oligonucleotides are 20-28 nucleotides long.

The oligonucleotide probe sets or primers, as noted above, have a reporter label suitable for detection. Useful labels include chromophores, fluorescent moieties, enzymes, antigens, heavy metals, magnetic probes, dyes, phosphorescent groups, radioactive materials, chemiluminescent moieties, and electrochemical detecting moieties.

The polymerase chain reaction process is fully described in H. Erlich, et. al., "Recent Advances in the Polymerase Chain Reaction," *Science* 252: 1643-50 (1991); M. Innis, et. al., *PCR Protocols: A Guide to Methods and Applications*, Academic Press: New York (1990); and R. Saiki, et. al., "Primer-directed Enzymatic Amplification of DNA with a Thermostable DNA Polymerase," *Science* 239: 487-91 (1988), which are hereby incorporated by reference.

A particularly important aspect of the present invention is its capability to quantify the amount of target nucleotide sequence in a sample. This can be achieved in a number of ways by establishing standards which can be internal (i.e. where the standard establishing material is amplified and detected with the sample) or external (i.e. where the standard establishing material is not amplified, and is detected with the sample).

In accordance with one quantification method, the signal generated by the reporter label, resulting from capture of ligation product sequences produced from the sample being analyzed, are detected. The strength of this signal is compared to a calibration curve produced from signals generated by capture of ligation product sequences in samples with known amounts of target nucleotide sequence. As a result, the amount of target nucleotide sequence in the sample being analyzed can be determined. This techniques involves use of an external standard.

Another quantification method, in accordance with the present invention, relates to an internal standard. Here, a known amount of one or more marker target nucleotide sequences is added to the sample. In addition, a plurality of marker-specific oligonucleotide probe sets are added along with the ligase, the previously-discussed oligonucleotide probe sets, and the sample to a mixture. The marker-specific oligonucleotide probe sets have (1) a first oligonucleotide probe with a target-specific portion complementary to the marker target nucleotide sequence, and (2) a second oligonucleotide probe with a target-specific portion complementary to the marker target nucleotide sequence and a detectable reporter label. The oligonucleotide probes in a particular marker-specific oligonucleotide set are suitable for ligation together when hybridized adjacent to one another on a corresponding marker target nucleotide sequence. However, there is a mismatch which interferes with such ligation when hybridized to any other nucleotide sequence present in the sample or added marker sequences. The presence of ligation product sequences is identified by detection of reporter labels. The amount of target nucleotide sequences in the sample is then determined by comparing the amount of ligation product sequence generated from known amounts of marker target nucleotide sequences with the amount of other ligation product sequences.

Another quantification method, in accordance with the present invention involves, analysis of a sample containing two or more of a plurality of target nucleotide sequences with a plurality of sequence differences. Here, ligation product sequences corresponding to the target nucleotide sequences are detected and distinguished by any of the previously-discussed techniques. The relative amounts of the target nucleotide sequences in the sample are then quantified by comparing the relative amounts of captured ligation product sequences generated. This provides a quantitative measure of the relative level of the target nucleotide sequences in the sample.

The preferred thermostable ligase is that derived from *Thermus aquaticus*. This enzyme can be isolated from that organism. M. Takahashi, et al., "Thermophillic DNA Ligase," *J. Biol. Chem.* 259:10041-47 (1984), which is hereby incorporated by reference. Alternatively, it can be prepared recombinantly. Procedures for such isolation as well as the recombinant production of *Thermus aquaticus* ligase (as well as *Thermus themophilus* ligase) are disclosed in WO 90/17239 to Barany, et. al., and F. Barany, et al., "Cloning, Overexpression and Nucleotide Sequence of a Thermostable DNA-Ligase Encoding Gene," Gene 109:1-11 (1991), which are hereby incorporated by reference. These references contain complete sequence information for this ligase as well as the encoding DNA. Other suitable ligases include *E. coli* ligase, T4 ligase, and *Pyococcus* ligase.

The ligation detection reaction mixture may include a carrier DNA, such as salmon sperm DNA.

The hybridization step in the ligase detection reaction, which is preferably a thermal hybridization treatment discriminates between nucleotide sequences based on a distinguishing nucleotide at the ligation junctions. The difference between the target nucleotide sequences can be, for example, a single nucleic acid base difference, a nucleic acid deletion, a nucleic acid insertion, or rearrangement. Such sequence differences involving more than one base can also be detected. Preferably, the oligonucleotide probe sets have substantially the same length so that they hybridize to target nucleotide sequences at substantially similar hybridization conditions. As a result, the process of the present invention is able to detect infectious diseases, genetic diseases, and cancer. It is also useful in environmental monitoring, forensics, and food science.

A wide variety of infectious diseases can be detected by the process of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli, Salmonella, Shigella, Klebsiella, Pseudomonas, Listeria monocytogenes, Mycobacterium tuberculosis, Mycobacterium avium-intracellulare, Yersinia, Francisella, Pasteurella, Brucella, Clostridia, Bordetella pertussis, Bacteroides, Staphylococcus aureus, Streptococcus pneumonia, B-Hemolytic strep., Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia,* and *Acitnomycetes.*

Fungal infectious agents which can be detected by the present invention include *Cryptococcus neoformans, Blastomyces dermatitidis, Histoplasma capsulatum, Coccidio-*

*ides immitis, Paracoccidioides brasiliensis, Candida albicans, Aspergillus fumigautus, Phycomycetes* (Rhizopus), *Sporothrix schenckii, Chromomycosis*, and *Maduromycosis*.

Viral infectious agents which can be detected by the present invention include human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present invention include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidum, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis, trematodes, Diphyllobothrium latum, Taenia* spp., *Pneumocystis carinii*, and *Necator americanis*.

The present invention is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present invention.

Genetic diseases can also be detected by the process of the present invention. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

Cancers which can be detected by the process of the present invention generally involve oncogenes, tumor suppressor genes, or genes involved in DNA amplification, replication, recombination, or repair. Examples of these include: BRCA1 gene, p53 gene, APC gene, Her2/Neu amplification, Bcr/Abl, K-ras-gene, and human papillomavirus Types 16 and 18. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety of forensic areas, including for human identification for military personnel and criminal investigation, paternity testing and family relation analysis, HLA compatibility typing, and screening blood, sperm, or transplantation organs for contamination.

In the food and feed industry, the present invention has a wide variety of applications. For example, it can be used for identification and characterization of production organisms such as yeast for production of beer, wine, cheese, yogurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

Desirably, the oligonucleotide probes are suitable for ligation together at a ligation junction when hybridized adjacent to one another on a corresponding target nucleotide sequence due to perfect complementarity at the ligation junction. However, when the oligonucleotide probes in the set are hybridized to any other nucleotide sequence present in the sample, there is a mismatch at a base at the ligation junction which interferes with ligation. Most preferably, the mismatch is at the base adjacent the 3' base at the ligation junction. Alternatively, the mismatch can be at the bases adjacent to bases at the ligation junction.

As noted supra, detection and quantification can be carried out using capillary or gel electrophoresis or on a solid support with an array capture oligonucleotides.

The use of capillary and gel electrophoresis for such purposes is well known. See e.g., Grossman, et. al., "High-density Multiplex Detection of Nucleic Acid Sequences: Oligonucleotide Ligation Assay and Sequence-coded Separation," *Nucl. Acids Res*. 22(21): 4527-34 (1994), which is hereby incorporated by reference.

The use of a solid support with an array of capture oligonucleotides is fully disclosed in pending provisional U.S. patent application Ser. No. 60/011,359, which is hereby incorporated by reference. When using such arrays, the oligonucleotide primers or probes used in the above-described coupled PCR and LDR phases, respectively, have an addressable array-specific portion. After the LDR or PCR phases are completed, the addressable array-specific portions for the products of such processes remain single stranded and are caused to hybridize to the capture oligonucleotides during a capture phase. C. Newton, et al., "The Production of PCR Products With 5' Single-Stranded Tails Using Primers That Incorporate Novel Phosphoramidite Intermediates," *Nucl. Acids Res*. 21(5):1155-62 (1993), which is hereby incorporated by reference.

During the capture phase of the process, the mixture is contacted with the solid support at a temperature of 45-90° C. and for a time period of up to 60 minutes. Hybridizations may be accelerated by adding cations, volume exclusion or chaotropic agents. When an array consists of dozens to hundreds of addresses, it is important that the correct ligation product sequences have an opportunity to hybridize to the appropriate address. This may be achieved by the thermal motion of oligonucleotides at the high temperatures used, by mechanical movement of the fluid in contact with the array surface, or by moving the oligonucleotides across the array by electric fields. After hybridization, the array is washed sequentially with a low stringency wash buffer and then a high stringency wash buffer.

It is important to select capture oligonucleotides and addressable nucleotide sequences which will hybridize in a stable fashion. This requires that the oligonucleotide sets and the capture oligonucleotides be configured so that the oligonucleotide sets hybridize to the target nucleotide sequences at a temperature less than that which the capture oligonucleotides hybridize to the addressable array-specific portions. Unless the oligonucleotides are designed in this fashion, false positive signals may result due to capture of adjacent unreacted oligonucleotides from the same oligonucleotide set which are hybridized to the target.

The capture oligonucleotides can be in the form of ribonucleotides, deoxyribonucleotides, modified ribonucleotides, modified deoxyribonucleotides, peptide nucleotide analogues, modified peptide nucleotide analogues, modified phosphate-sugar backbone oligonucleotides, nucleotide analogues, and mixtures thereof.

Where an array is utilized, the detection phase of the process involves scanning and identifying if LDR or PCR products have been produced and correlating the presence of such products to a presence or absence of the target nucleotide sequence in the test sample. Scanning can be carried out by scanning electron microscopy, confocal microscopy, charge-coupled device, scanning tunneling electron microscopy, infrared microscopy, atomic force microscopy, electrical conductance, and fluorescent or phosphor imaging. Correlating is carried out with a computer.

EXAMPLES

LDR/PCR Process

Example 1

Genomic DNA Preparation

Genomic DNA was prepared from the blood of two normal human volunteers, one male and one female, according to standard techniques. Briefly, approximately 12 ml of blood was obtained in EDTA-containing blood collection tubes. Red blood cells were lysed by mixing the blood samples with 4 volumes of lysis buffer (10 mM Tris pH 8.0, 10 mM EDTA). After 10 min on ice with occasional agitation, the suspensions were centrifuged and the supernatants were decanted. The white blood cell pellets were resuspended in 20 ml of lysis buffer, and the above process was repeated. Each cell pellet was then suspended in 15 ml of digestion buffer (50 mM Tris pH 8.0, 5 mM EDTA, 100 mM NaCl, 1% SDS) and 3 mg (0.2 mg/ml) of proteinase K was added. The cells were digested at 37° C. for 5 hours. The digests were extracted twice with equal volumes of phenol, then once with equal volumes of a 1:1 phenol:chloroform mixture and finally once with equal volumes of chloroform, each time centrifuging the mixture and removing the aqueous phase for the next extraction. After the final extraction and removing the aqueous phases, one tenth volume of 3 M sodium acetate, pH 6.5, was added. Two volumes of ice cold 100% EtOH were then added to each solution to precipitate the genomic DNAs, which were spooled out of solution on glass pipettes. The DNA precipitates were washed twice in 0.75 ml volumes of 70% EtOH, briefly centrifuging each time to allow removal of the supernatants. After removing the supernatants for the second time, the remaining EtOH was allowed to evaporate and the DNA was suspended in 0.5 ml of TE (10 mM Tri-HCl pH 8.0 containing 1 mM EDTA) solution. A fifth dilution of each DNA solution was also prepared in TE.

To determine the concentrations of the one fifth DNA solutions, 1, 2, and 4 μl aliquots of each were loaded on a 1% agarose gel with a known amount of HindIII digested lambda DNA as a control. The gel was run at 150 Volts for 2 hours with ethidium bromide in the electrophoresis buffer. After photographing the gel and comparing the intensities of the DNA bands, the one fifth dilutions were judged to have concentrations of approximately 100 ng/ml. DNA solutions extracted from various tumor cell lines were the generous gifts of other laboratories. The concentrations of these solutions were checked in a similar fashion and solutions of 100 ng/ml in TE were prepared.

To digest the genomic DNAs with Taq I, 25 μl of the 100 ng/μl solutions was mixed with 5 μl of 10× medium salt buffer (0.5 M NaCl, 0.1 M MgCl$_2$, 0.1 M Tris, pH 8.0), 20 μl of water-ME (i.e. water containing 6 mM ME (i.e., mercaptoethanol)), and 400 U of Taq I restriction endonuclease. The digests were covered with mineral oil and incubated at 65° C. for 1 hour. The reactions were stopped by adding 1.2 μl of 500 mM EDTA and heating the specimens to 85° C. for 10 min. Complete digestion of the DNAs was checked by electrophoresing aliquots on a 1% agarose gel.

Example 2

Oligonucleotide Preparation for LDR Probes and PCR Primers

All oligonucleotides were synthesized on a 394A DNA Synthesizer (Applied Biosystems Division of Perkin-Elmer Corp., Foster City, Calif.). Oligonucleotides labeled with 6-FAM were synthesized using the manufacturer's suggested modifications to the synthesis cycle (Applied Biosystems Inc., 1994) and were subsequently deprotected at 55° C. for 4 hr. LDR oligonucleotides were purified by ethanol precipitation after overnight deprotection at 55° C. The primer-specific portions of the oligonucleotides used for PCR amplification were purified by polyacrylamide gel electrophoresis on 10% acryl amide/7M urea gels. Oligonucleotides were visualized after electrophoresis by UV shadowing against a lightening screen and excised from the gel (Applied Biosystems Inc., 1992). They were then eluted overnight at 64° C. in TNE (i.e. Tris-sodium EDTA) buffer (100 mM Tris/HCl pH 8.0 containing 500 mM NaCl and 5 mM EDTA) and recovered from the eluate using Sep Pak cartridges (Millipore Corp, Milford, Mass.) following the manufacture's instructions.

Oligonucleotides were resuspended in 100 μl TE (i.e. 10 mM Tri-HCl pH 8.0 containing 1 mM EDTA). Typical concentrations of these original LDR probe solutions are about 1 μg/μl or approximately 74 pm/μl as determined by the following formula:

$$[\text{concentration } (\mu g/\mu l) \times 10^6)] / [\text{length } (nt) \times 325] = pm/\mu l$$

The concentrations of the LDR probes are given in Table 1. The concentrations of oligonucleotides complementary to the oligonucleotide probes of the ligase detection reaction were higher. ZipALg1F was 3.75 μg/μl and ZipBLg2R was 2.01 μg/μl or 524 pm/μl and 281 pm/μl, respectively, as determined by the formula above.

TABLE 1

| Primer | Length | µg/µl | pm/µl | Vol = 100 pm | l = 200 pm |
|---|---|---|---|---|---|
| G6PDEx6-3L | 48 nt | 0.86 | 55.1 | 1.81 µl | 3.63 µl |
| G6PDEx6-4R | 48 | 0.65 | 41.7 | 2.4 | 4.8 |
| ErbBEx1-5L | 48 | 0.95 | 60.9 | 1.64 | 3.28 |
| ErbBEx1-5R | 48 | 1.4025 | 89.9 | 1.11 | 2.22 |
| Int2Ex3-7L | 50 | 1.6005 | 98.5 | 1.02 | 2.03 |
| Int2Ex3-8R | 46 | 1.306 | 87.4 | 1.14 | 2.29 |
| p53Ex8-9L | 2 | 1.036 | 61.3 | 1.63 | 3.26 |
| p53Ex8-10R | 44 | 1.164 | 81.4 | 1.23 | 2.46 |
| SODEx3-11L | 49 | 1.287 | 80.8 | 1.24 | 2.48 |
| SODEx3-12R | 47 | 1.2045 | 78.9 | 1.27 | 2.53 |

As a prerequisite for the LDR phase, the downstream LDR oligonucleotides probes were phosphorylated with T4 polynucleotide kinase. Aliquots of the 5 downstream oligonucleotides equivalent to 200 pm (see Table 1) were combined with 10 µl of 10× kinase buffer (500 mM Tris/HCl pH 8.0, 100 mM $MgCl_2$), 10 µl of 10 mM ATP, 20 U T4 kinase, and sufficient water-ME to give a final volume of 100 µl. Phosphorylation was carried out at 37° C. for 30 min followed by incubation for 10 min at 85° C. to inactivate the T4 enzyme. The resulting concentration of the kinased LDR probe solution was 2 pm/µl or 2000 fm/µl in each probe.

The kinase reaction is summarized as follows:

| | |
|---|---|
| 4.8 µl | G6PDEx6-4R |
| 2.2 µl | ErbBEx1-5R |
| 2.3 µl | Int2Ex3-8R |
| 2.5 µl | p53Ex8-10R |
| 2.5 µl | SODEx3-12R |
| 10 µl | 10 × Kinase Buffer |
| 10 µl | 10 mMATP |
| 65.7 µl | HOH + ME |
| 100 µl | Total |
| + 2 µl | = 20 units T4 Kinase |

37° C. for 30 min.
Heat kill kinase, 85° C., 10 min.
Final concentration = 2 pm/µl = 2000 fm/µl The solutions of the LDR and PCR oligonucleotides were adjusted to convenient concentrations. The kinased LDR probe solution was diluted fourfold in water to yield a concentration of 500 fm/µl. A solution of the upstream LDR probes was made by combining volumes of the probes equivalent to 200 pm (see Table 1) with sufficient water to give a final volume of 400 µl. This created a solution 500 fm/µl in each of the upstream LDR probes. Aliquots (20 µl) of the kinased and unkinased LDR probes were frozen for subsequent use. Standard solutions of the PCR primers (10 pm/µl) were prepared from their original solutions by combining 9.5 p of ZipALg1F and 17.8 µl of ZipBLg2R with sufficient water to achieve a total volume of 500 µl. These solutions were frozen for use in the LDR/PCR process. Unkinased probes were prepared according to the following:

| | |
|---|---|
| 200 pm | ea Primer |
| 3.62 µl | G6PDEx6-3L |
| 3.28 µl | ErbBEx1-5L |
| 2.04 µl | Int2Ex3-7L |
| 3.26 µl | p53Ex8-9L |
| 2.48 µl | SODEx3-11L |
| 385.32 µl | HOH |
| 400 µl | Total Vol |

Final concentration = 0.5 pm/µl = 500 fm/µl

TABLE 2

Sequences
Probe (length in nt)

| Gene | Location | Upstream | Downstream | Ligation Position |
|---|---|---|---|---|
| erb | 17q12–q21 | erbBEx1-5L (48) | erbBEx1-6R (48) | exon "1" P40 |
| G6PD | Xq28 | G6PDEx6-3L (48) | G6PDEx6-4R (48) | exon 6 W1145 |
| Int2 | 11q13 | Int2Ex3-7L (50) | Int2Ex3-8R (46) | exon 3 W135 |
| p53 | 17p13.1 | p53Ex8-9L (52) | p53Ex8-10R (44) | exon 8 P51 |
| SOD | 21q22.1 | SODEx3-11L (49) | SODEx3-12R (47) | exon 3 P355 |

Figure 24:
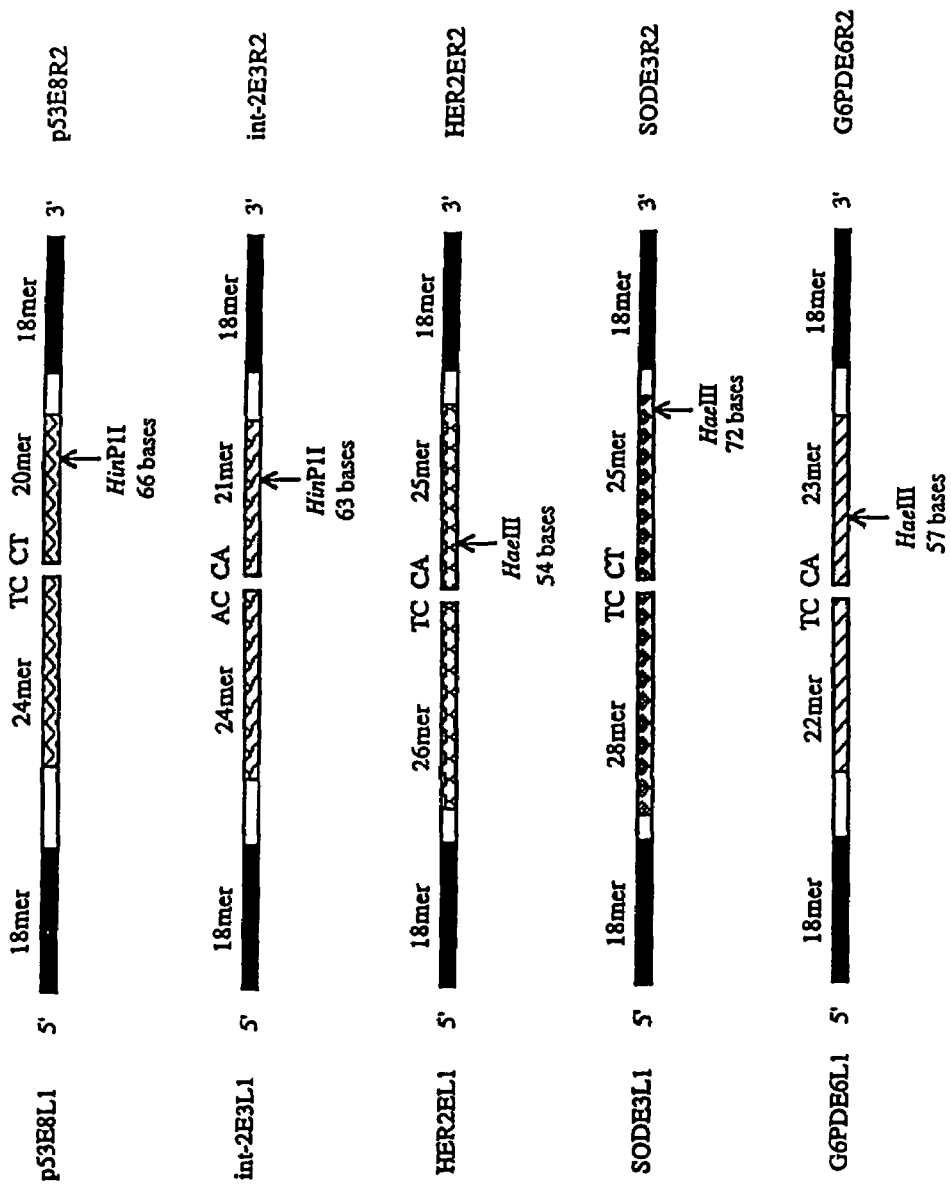
FIG. 24 shows the design of LDR oligonucleotide probes for quantification of gene amplifications and deletions in an LDR/PCR process.
Figure 25A:
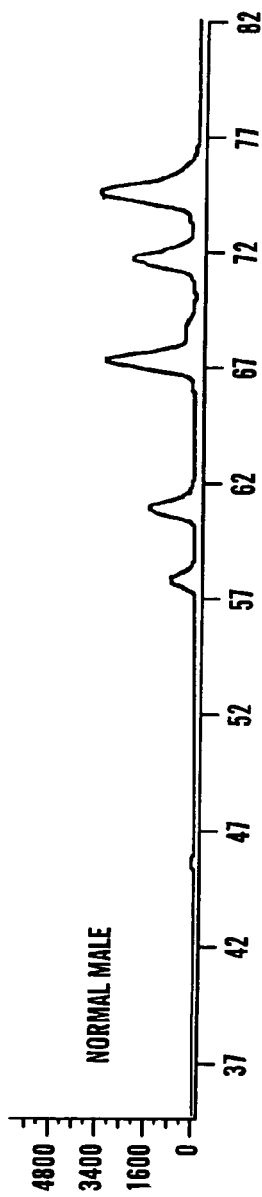
FIGS. 25A-D show electropherogram results for an LDR/PCR process.
Figure 25B:
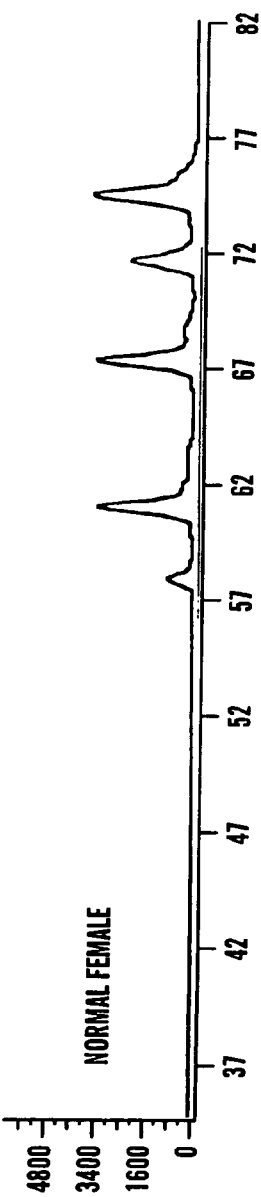
Figure 25C:
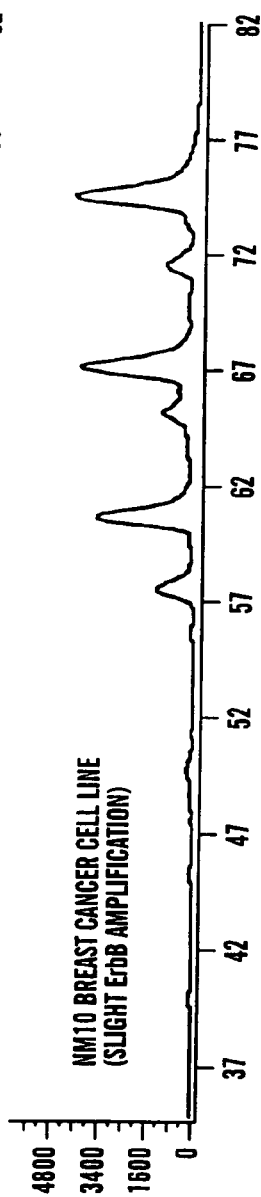
Figure 25D:
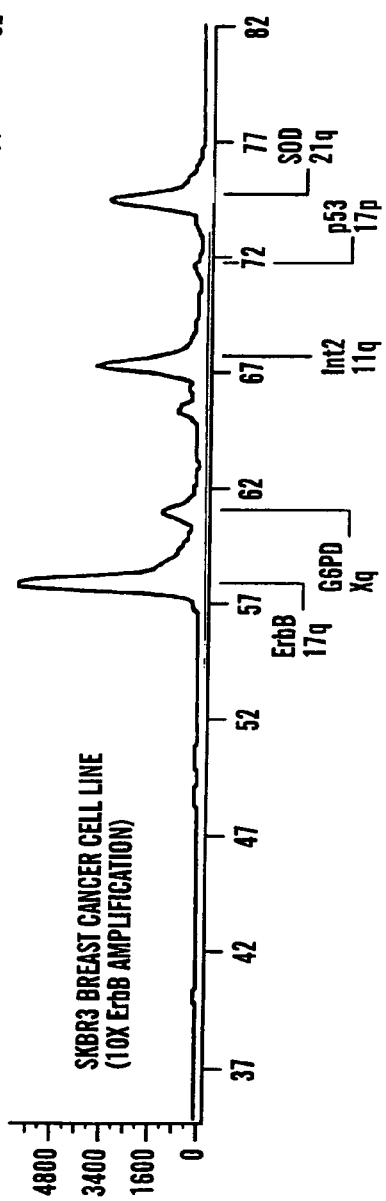

FIG. 24 shows the design of LDR oligonucleotide probes for quantification of gene amplifications and deletions in the LDR/PCR process. These oligonucleotide probes were designed to recognize exon 8 in the p53 tumor suppressor gene (on chromosome 17p), exon 3 of int-2 (on chromosome 11 q), an internal exon in HER-2/neu (i.e. HER-2/neu/erbB oncogene) (on chromosome 17q), exon 3 in SOD. (i.e. super oxide dimutase) (on chromosome 21(q), and exon 6 in G6PD (i.e. glucose 6-phosphate dehydrogenase) (on chromosome Xq). Each pair of LDR oligonucleotide probes has the following features: (i) The left oligonucleotide probe contains from 5' to 3' an 18 base sequence identical to the fluorescently labeled secondary oligonucleotide primer (black bar), an "adjustment sequence" (white bar), and a target-specific sequence of from 22 to 28 bases with a $T_m$ of 75° C. (patterned bar); (ii) The right oligonucleotide probe contains from 5' to 3' a target-specific sequence of 20-25 bases with a $T_m$ of 75° C. (patterned bar), a single HaeIII or HinPII restriction site at slightly different positions within the target-specific sequence, and an "adjustment sequence" (white bars). The two oligonucleotide probes are designed such that their combined length is exactly 96 bases, with 50 G+C bases and 46 A+T bases. The position of each unique restriction site generates a product which differs by at least 2 bases from the other products. Each oligonucleotide probe set has an exon-specific region chosen to ligate the junction sequence of (A, T)C C(A, T). This junction sequence corresponds to either a proline residue (codon CCN) or the complementary sequence of a tryptophan residue (TGG). These sequences were chosen to minimize differences in ligation rates and the chance of a polymorphism at the ligation junction.

LDR Probe Sequences

```
G6PDEx6-3L
5'CAC GCT ATC CCG TTA GAC ATT GTC      (SEQ. ID. NO. 1)
AAG CAG GCG ATG TTG TCC CGG TTC 3'

G6PDEx6-4R
5'CAG ATG GGG CCG AAG ATC CTG TTA      (SEQ. ID. NO. 2)
TTG ATA CAT AGT GCG GTA GTT GGC 3' erbBEx1-5L
5'CAC GCT ATC CCG TTA GAC ATC GCC      (SEQ. ID. NO. 3)
CTG ATG GGG AGA ATG TGA AAA TTC 3' erbBEx1-6R
5'CAG TGG CCA TCA AAG TGT TGA GGG      (SEQ. ID. NO. 4)
AGC GTA CAT AGT GCG GTA GTT GGC 3'

Int2Ex3-7L
5'CACGCTATCCCGTTAGAC ATT CAT           (SEQ. ID. NO. 5)
AAC CCT TGC CGT TCA CAG ACA CGT AC
3'

Int2Ex3-8R
5'CAC AGT CTC TCG GCG CTG GGC AAT      (SEQ. ID. NO. 6)
AAT ACA TAG TGC GGT AGT TGG C 3' p53Ex8-9L
5'CAC GCT ATC CCG TTA GAC ATC TTA      (SEQ. ID. NO. 7)
GTA ATT GAG GTG CGT GTT TGT GCC
TGT C 3' p53Ex8-10R
5'CTG GGA GAG ACC GGC GCA CAT          (SEQ. ID. NO. 8)
TAC TAC ATA GTG CGG TAG TTG GC 3'

SODEx-3-11L
5'CACGCTATCCCGTTAGAC ATC TGT           (SEQ. ID. NO. 9)
ACC AGT GCA GGT CCT CAC TTT AAT C
3'

(SEQ. ID. NO. 10)
SODEx-3-12R
5'CTC TAT CCA GAA AAC ACG GTG GGC
CGC TACATAGTGCGGTAGTTGGC 3'
```

PCR Primers:

```
ZipALg1F
5' Fam-GGA                    (SEQ. ID. NO. 11)
GCA CGC TAT CCC GTT AGA C 3'  (Tm = 71° C.)

ZipBLg2R
5' CGC                        (SEQ. ID. NO. 12)
TGC CAA CTA CCG CAC TAT G 3'  (Tm = 72° C.)
```

(Underlined sequences are common between LDR probes and ZipALg1F or the complement of ZipBLg2R.)

Example 3

Buffers and Reagents

A. LDR Buffers/Reagents—the following LDR buffers and reagents were selected:
10×ST ligase buffer (0.2 M Tris pH 8.5, 0.1 M MgCl$_2$) [This was also tested with Tris at pH 7.6.]
10×TT ligase buffer (0.2 M Tris pH 7.6, 0.5 M KCl, 0.1 M MgCl2, 5 mM EDTA)
NAD (10 mM)
DTT (200 mM)
LDR primer solution containing one tenth concentration of each of the LDR primer mixtures (50 fin of each LDR primer per μl)

Tth DNA Ligase (625 U/μl)

PCR Buffers/Reagents—the following PCR buffers and reagents were selected:
10× Stoffel buffer (0.1 M KCl 0.1M Tris-HCl pH 8.3 Perkin Elmer)
dNTP solution (100 mM total, 25 mM of each dNTP Perkin Elmer), diluted 5 fold in dHOH to a final concentration of 5 mM of each dNTP
ZipALg1F (10 pm/μl)
ZipBLg2R (10 pm/μl)

Example 4

LDR/PCR Process

Four LDR/PCR processes were performed for each DNA to be tested with reaction tubes PCR amplified to 22, 24, 26, and 30 cycles to assure that one reaction would be halted in the exponential phase. Each LDR reaction (20 μl) was thermal cycled and then a PCR mix (30 μl) containing primers with a portion complementary to the primer-specific portion of the LDR probes was added to each specimen to allow exponential amplification. To minimize differences between reaction tubes, master mixes of LDR and PCR reagents were made.

A master mix of LDR reagents was constructed with a volume sufficient for all reaction tubes. Proportions and volumes for a single reaction were as follows:

| Reagent | Volume |
| --- | --- |
| 10X ST Ligase Buffer | 2 μl |
| NAD (10 mM) | 2 μl |
| DTT (200 mM) | 1 μl |
| dHOH | 5 μl |
| Total | 10 μl |
| Tth DNA Ligase | 0.2 μl |
| | (=125 U) |

Mixes of target DNA and LDR probes for each reaction tube were constructed with the following proportions:

| Reagent | Volume |
| --- | --- |
| DNA (TaqI digested) | 1 μl (=50 ng) |
| LDR Probe Mix | 4 μl (200 fm each primer) |
| dHOH | 5 μl |
| Total | 10 μl |

For each reaction, 10 μl was placed in a thin-walled PCR tube, rapidly mixed with 10 μl of LDR reagent mix (including ligase), overlayed with mineral oil, and placed in a Perkin Elmer 9600 thermal cycler.

LDR was initiated by holding at 96° C. for 2 minutes to denature the DNA followed by 10 cycles of 94° C. for 30 seconds and 65° C. for 4 minutes.

PCR reagent mixes for each reaction tube were constructed with the following proportions:

| Reagent | Volume |
| --- | --- |
| 10X Stoffel buffer | 5 µl |
| dNTP solution | 8 µl (=0.8 mM each dNTP in final reaction) |
| ZipALg1F (10 pm/µl) | 2.5 µl (=25 pm per reaction) |
| ZipBLg2R (10 pm/µl) | 2.5 µl (=25 pm per reaction) |
| dHOH | 12 µl |
| Total | 30 µl |
| Stoffel Fragment | 0.25 µl (=2.5 U) |

At the completion of the LDR reaction, the tubes were held at 94° C., while 30 ml of PCR reagent mix (including Stoffel fragment) were added to each tube. PCR amplification was accomplished by thermal cycling at 94° C. for 15 seconds followed by 60° C. for 50 seconds. At 22, 24, 26, and 30 cycles, respectively, one of four identical reaction tubes of each DNA specimen was removed and quenched in a slurry of dry ice and ETOH.

Example 5

Agarose Gel Evaluation

Ten microliter aliquots of the 26 and 30 cycle reaction specimens were evaluated on a 2% agarose gel. Ethidium bromide staining revealed bands of the expected size (104 bp).

Example 6

Digestion of Products, Preparation of Dilutions, and Loading on GeneScanner

To separate the gene-specific LDR/PCR products, 10 µl aliquots of the 22, 24, and 26 cycle reactions were digested by adding 10 µl of a solution containing 5 U each of HaeIII and HinPII restriction enzymes (both from New England BioLabs), 2 µl of 10× restriction enzyme buffer number 2 (New England BioLabs), and 8 µl of dHOH (i.e. distilled water). The digests were incubated at 37° C. for one hour and then stopped by the addition of 1 µl of 0.5 M EDTA, pH 8.0. The restriction digests were a one half dilution of the original LDR/PCR products. A 10 fold dilution of each sample was also prepared by adding 5 µl of each restriction digest to 20 µl of TE buffer.

Before loading samples on the ABI 373A DNA-Sequencer (Applied Biosystems) a 1:5 mixture of 50 mM EDTA pH 8.0 containing 2% blue dextran and de-ionized formamide was made. To 5 µl of the EDTA-Blue Dextran solution, 5 µl of digested LDR/PCR product dilution and 1 µl of GENESCAN 1000 ROX marker (Applied Biosystems) were added. These solutions were heated to 85° C. for 10 minutes and snap chilled on ice, before 5.5 µl were loaded on the denaturing gel.

Samples were analyzed in an Applied Biosystems 373A DNA sequencer on a 0.4 mm thick, 10% polyacrylamide/7M urea gel with a well-to-read distance of 12 cm. The gel matrix was buffered with 1.2×TBE (106 mM Tris-borate and 2.4 mM EDTA pH 8.3) and the electrophoresis chamber buffer contained 0.6×TBE (53.4 mM Tris-borate and 1.2 mM EDTA pH 8.3). The gel was pre-run prior to sample loading at 1600 V for 30 minutes with the electrode polarity reversed (anode in the chamber with sample wells at the top of the gel). After loading, the gene-specific LDR/PCR products were electrophoresed at 1200 V and the primary data was captured using the ABI 672 Data Collection Software V1.1 (Applied Biosystems)

Using the ABI 672 GeneScan Analysis Software V1.2.2 (Applied Biosystems), the resulting data were displayed as electropherograms, with peak heights and peak areas calculated.

In the normal female, the ErbB2 peak is lower, and the p53 peak is slightly lower than the remaining 3 peaks. See FIGS. 25A-D. In different experiments, it was observed that the ErbB2 peak is always lower, the G6PD, Int-2, p53, and SOD peak areas would vary somewhat, but all 5 peaks would retain the same relative profile from one sample to the next for a given experiment. When comparing male with female DNA, the G6PD peak was about half the area of other peaks, consistent with a single X-chromosome in males, while the other peaks were essentially the same. The ErB2 peak for the NM10 Breast Cancer cell line is slightly elevated, while that in cell line SKBR3 is several fold-greater than the normal female control, reflecting the known ErbB-2 gene amplification in these two cell lines. In addition, cell line NM10 appears to have undergone LOH (i.e. a loss of heterozygosity) of p53, while cell line SKBR3 appears to have undergone LOH of G6PD and p53. Some of the cells in cell line SKBR3 may have lost both copies of the p53 gene. Repeating these amplifications in the absence of the ErbB-2 primers was used to confirm the presence of these additional gene deletions (see below).

These results can be quantified by comparing the ratio of peak areas in each peak to a standard (the SOD peak area) for that experiment. The raw data and ratio of peak areas are given below:

TABLE 3

Raw Peak Area Data

| | Genes | | | | |
| --- | --- | --- | --- | --- | --- |
| | ErB | G6PD | Int2 | p53 | SOD |
| Male | 9954 | 21525 | 45688 | 36346 | 62506 |
| Female | 8340 | 39309 | 39344 | 30270 | 54665 |
| NM10 | 20096 | 55483 | 67083 | 17364 | 84339 |
| SKBR3 | 106650 | 19120 | 50103 | 2888 | 48119 |

TABLE 4

Ratio of Peak Areas to SOD Peak Area

| | ErbB/SOD | G6PD/SOD | Int2/SOD | p53/SOD |
| --- | --- | --- | --- | --- |
| Male | 0.16 | 0.34 | 0.73 | 0.58 |
| Female | 0.15 | 0.72 | 0.72 | 0.55 |
| NM10 | 0.24 | 0.66 | 0.80 | 0.21 |
| SKBR3 | 2.22 | 0.40 | 1.04 | 0.06 |

Although the ratios differ for each gene, (due to different efficiencies of LDR/PCR for each gene) the ratios are generally consistent between the male and female sample, except for the G6PD/SOD ratio. The G6PD for the female is about twice the value as the male, accurately reflecting the presence of two and one X chromosome, respectively. One can quantify the amount of ErbB2 amplification by comparing the ratio of peak area ratios between normal DNA and cancer cell lines.

TABLE 5

Ratio of Peak Areas Ratios

|  | ErbB/2 | G6PD | Int2 | p53 |
|---|---|---|---|---|
| Female/Male | 0.96 | 2.09 | 0.98 | 0.95 |
| NM10/Male | 1.50 | 1.91 | 1.09 | 0.35 |
| SKBR3/Male | 13.92 | 1.15 | 1.42 | 0.10 |

From these ratios, it can be determined that the normal male and female have the same number of genes on chromosomes 17q (ErbB), 17p (p53), and 11 q (Int 2), but that the female has twice as many G6PD genes, or X chromosomes. Likewise, cell line NM10 showed slight amplification of the ErbB-2 gene, and LOH at p53, while cell line SKBR3 shows significant amplification of the ErbB-2 gene, LOH at G6PD and p53. To confirm additional gene amplifications and deletions, primer pairs causing massive amplifications may be removed from the LDR/PCR reaction (see below).

In the normal female, the ErbB2 peak is lower than the remaining 4 peaks. In different experiments, it was observed that the G6PD, Int-2, p53, and SOD peak areas would vary somewhat, but would retain the same relative profile from one sample to the next. See FIGS. 26A-C. The ErbB2 peak was consistently lower, and slight shoulders were observed on the G6PD and SOD peaks, for unknown reasons. The ErbB-2 peak in both cell line samples is several fold greater than the normal female control, reflecting the known ErbB-2 gene amplification in these two cell lines. In addition, the ZR-75-30 line appears to show LOH of p53, while the SKGT-2 cell line appears to have a slight amplification of the Int-2 region. By repeating these LDR/PCR experiments in the absence of the ErbB-2 primers, it was demonstrated that these results are not artifacts of the massive levels of ErbB-2 amplification. See FIGS. 27A-C. Both gene amplifications and deletions for multiple genes using the LDR/PCR format have been demonstrated. See FIGS. 26A-C and 27A-C.

Again, these results can be quantified by comparing the ratio of peak areas in each peak to a standard (the SOD peak area) for that experiment. The raw data and ratio of peak areas are given below:

TABLE 6

Raw Peak Area Data

| | Genes | | | | |
|---|---|---|---|---|---|
|  | ErbB | G6PD | Int2 | p53 | SOD |
| Female; 4 Primer Sets | NA | 9577 | 8581 | 9139 | 8128 |
| ZR7530; 4 Primer Sets | NA | 8452 | 7904 | 4168 | 7996 |
| SKGT2; 4 Primer Sets | NA | 15915 | 28614 | 13116 | 12478 |
| Female; 5 Primer Sets | 3955 | 9436 | 8066 | 9304 | 8848 |
| ZR7530; 5 Primer Sets | 66748 | 11105 | 8812 | 4163 | 9303 |
| SKGT2; 5 Primer Sets | 263254 | 21877 | 31887 | 13630 | 13480 |

TABLE 7

Ratio of Peak Areas to SOD Peak Area

|  | ErbB/SOD | G6PD/SOD | Int2/SOD | p53/SOD |
|---|---|---|---|---|
| Female; 4 Primer Sets | NA | 1.18 | 1.06 | 1.12 |
| ZR7530; 4 Primer Sets | NA | 1.06 | 0.99 | 0.52 |
| SKGT2; 4 Primer Sets | NA | 1.28 | 2.29 | 1.05 |

TABLE 7-continued

Ratio of Peak Areas to SOD Peak Area

|  | ErbB/SOD | G6PD/SOD | Int2/SOD | p53/SOD |
|---|---|---|---|---|
| Female; 5 Primer Sets | 0.45 | 1.97 | 0.91 | 1.05 |
| ZR7530; 5 Primer Sets | 7.17 | 1.19 | 0.95 | 0.45 |
| SKGT2; 5 Primer Sets | 19.53 | 1.62 | 2.37 | 1.01 |

The ratios are remarkably consistent between the four primer set and the five primer set experiments. The only exception is the G6PD peak for the SKGT2 cell line, where the huge peak for ErbB-2 may have added to the G6PD peak.

One can quantify the amount of ErbB2 and Int-2 amplification as well as p53 deletion by comparing the ratio of peak area ratios between normal DNA and cancer cell lines, as shown in Table 8. In addition, the ratios from using 4 sets of primers can be compared with 5 sets of primers to ascertain the internal consistency of this technique.

TABLE 8

Ratio of Peak Area Ratios

|  | ErbB | G6PD | Int2 | p53 |
|---|---|---|---|---|
| Female; 4/5 | NA | 1.10 | 1.16 | 1.07 |
| ZR7530; 4/5 | NA | 0.89 | 1.04 | 1.16 |
| SKGT2; 4/5 | NA | 0.79 | 0.97 | 1.04 |
| ZR7530/Female; 4/4 | NA | 0.90 | 0.94 | 0.46 |
| ZR7530; Female; 5/5 | 16.05 | 1.12 | 1.04 | 0.43 |
| SKGT2/Female; 4/4 | NA | 1.08 | 2.17 | 0.93 |
| SKGT2; Female; 5/5 | 43.69 | 1.52 | 2.59 | 0.96 |

The values for the top half of Table 8 should all be close to 1.0 if the LDR/PCR technique is internally consistent, when using 4 or 5 primers. All values are very close to 1.0. Again, the value for G6PD for SKGT2 is a bit low for the reasons mentioned.

The values on the bottom half of Table 8 show the extent of ErbB-2 amplification. The numbers are quite consistent for the 4 primer and 5 primer amplifications (with the exception of SKGT2-G6PD noted above). The ZR7530 cell line demonstrates a clear LOH for p53, while the SKGT2 cell line shows amplification of the Int-2 region, and both p53 genes present.

Primary PCR/Secondary PCR/LDR Process

Example 7

Oligonucleotide Synthesis

Oligonucleotides were assembled by standard phosphoramidite chemistry on an Expedite DNA synthesizer (Persep-tive Biosystems, Framingham, Mass.). Oligonucleotides 5'-end labeled with 6-FAM, TET, and HEX were synthesized using the appropriate dye phosphoramidites (Perkin Elmer-Applied Biosystems) and purified with Oligonucleotide Purification Cartridges (Perkin Elmer-Applied Biosystems) following the manufacturer's protocol (Applied Biosystems Division-Perkin Elmer Corp., "Synthesis and Purification of Fluorescently Labeled Oligonucleotides Using Dye Phosphoramidites," *User Bulletin*, number 78, Applied Biosystems Division, Foster City, Calif., (1994)), which is hereby incorporated by reference. All oligonucleotides were checked for purity on an Applied Biosystems 270-HT capillary electrophoresis instrument using a mPAGE-3 column (J&W Scientific, Folsom, Calif.). Only oligonucleotides that were greater than 95% pure were used for the experiments. Oligonucleotides were resuspended in 250 ml TE (10 mM Tris/HCl and 5 mM EDTA pH 8.0). Typical concentrations were 300-500 mM for crude stock solutions and 100-200 mM for OPC (i.e. Oligonucleotide Purification Columns available from Applied Biosystems) purified stock solutions. For PCR and LDR, oligonucleotides were diluted to working solutions of 10 mM (10 pmoles/ml) or 5 mM (5 pmoles/ml).

Example 8

Phosphorylation of LDR Oligonucleotides

The 12 LDR common oligonucleotides were phosphorylated at the 5' end to permit ligation to the fluorescent labeled oligonucleotides. The oligonucleotides are shown below in Table 9.

TABLE 9

LDR Oligonucleotide Sequences

| Locus | Allele-Specific Oligonucletide (5' -> 3') | Common Oligonucleotide (5' -> 3') |
|---|---|---|
| 1 | FAM-AGCTTCAATGATGAGAACCTGC (SEQ. ID. NO. 13) | P-GCATAGTGGTGGCTGACCTGTTC<u>ATAT</u> (SEQ. ID. NO. 14) |
|   | TET-AGCTTCAATGATGAGAACCTGT (SEQ. ID. NO. 15) | |
| 2 | FAM-CTCCATGGGCCCAGCC (SEQ. ID. NO. 16) | P-AGCACTGGTGCCCTGTGAG (SEQ. ID. NO. 17) |
|   | TET-CTCCATGGGCCCAGCT (SEQ. ID. NO. 18) | |
| 3 | FAM-GGGGACAGCCATGCACTGA (SEQ. ID. NO. 19) | P-GCCTCTGGTAGCCTTTCAACCAT<u>A</u> (SEQ. ID. NO. 20) |
|   | TET-GGGGACAGCCATGCACTGC (SEQ. ID. NO. 21) | |
| 4 | FAMTTAGAAATCATCAAGCCTAGGTCAT (SEQ. ID. NO. 22) | P-CACCTTTTAGCTTCCTGAGCAATG<u>AT</u> (SEQ. ID. NO. 23) |
|   | TET-TTAGAAATCATCAAGCCTAGGTCAG (SEQ. ID. NO. 24) | |
| 5 | HEX-GGTTGTATTTGTCACCATATTAATTA (SEQ. ID. NO. 25) | P-ATTTTTCTCTATTGTTTTCATCTTTCAGGA (SEQ. ID. NO. 26) |
|   | HEX-<u>AT</u>GGTTGTATTTGTCACCATATTAATTG (SEQ. ID. NO. 27) | |
| 6 | FAM-GGGCCAAGAAGGTATCTACCA (SEQ. ID. NO. 28) | P-ATAGTGTCTATTAGGCATTTGAAAATGTG<u>TAT</u> (SEQ. ID. NO. 29) |
|   | TET-GGGCCAAGAAGGTATCTACCG (SEQ. ID. NO. 30) | |
| 7 | FAM-ACACAGCAGCTTACTCCAGAGG (SEQ. ID. NO. 31) | P-TCAAGTCCAAGGCCATTGGCT<u>TATA</u> (SEQ. ID. NO. 32) |
|   | TET-ACACAGCAGCTTACTCCAGAGA (SEQ. ID. NO. 33) | |
| 8 | FAM-CCAGCAAAGAGAAAAGAAGGG (SEQ. ID. NO. 34) | P-CCCCAGAAATCACAGGTGGGC<u>TAT</u> (SEQ. ID. NO. 35) |
|   | TET-CCAGCAAAGAGAAAAGAAGGA (SEQ. ID. NO. 36) | |
| 9 | FAM-ATGATATTAGAGCTCACTCATGTCCA (SEQ. ID. NO. 37) | P-TCAGTTTGGAAAAAGACAAAGAATTCTTT (SEQ. ID. NO. 38) |
|   | TET-ATGATATTAGAGCTCACTCATGTCCG (SEQ. ID. NO. 39) | |
| 10 | HEX-TGCTGTCTTCCAGGAATCTGTT (SEQ. ID. NO. 40) | P-CAACTCTCTCGAAGCCATGTTCAC<u>AA</u> (SEQ. ID. NO. 41) |
|   | HEX-<u>A</u>TTGCTGTCTTCCAGGAATCTGTG (SEQ. ID. NO. 42) | |

TABLE 9-continued

LDR Oligonucleotide Sequences

| Locus | Allele-Specific Oligonucletide (5' -> 3') | Common Oligonucleotide (5' -> 3') |
|---|---|---|
| 11 | HEX-GGACATAGTGACCGTGCAGGTC (SEQ. ID. NO. 43) | P-CTTCCCCAGTGTGAGTGCCG<u>TA</u> (SEQ. ID. NO. 44) |
|  | HEX-<u>AT</u>GGACATAGTGACCGTGCAGGTT (SEQ. ID. NO. 45) |  |
| 12 | HEX-CTATGACACCGTCATCAGCAGG (SEQ. ID. NO. 46) | P-GACATCCAGGCCCCCGAC (SEQ. ID. NO. 47) |
|  | HEX-<u>TA</u>CTATGACACCGTCATCAGCAGA (SEQ. ID. NO. 48) |  |

The allele-specific oligonucleotides are 5' end labeled with either FAM, TET, or HEX. All the common oligonucleotides are phosphorylated at the 5' end. Underline denotes tails that are not complementary to the target sequence. LDR primer sets were designed in two ways: (i) allele-specific primers were of the same length but contained either FAM or TET label; or (ii) the allele-specific primers were both labeled with HEX but differed in length by two bases.

This was accomplished either during the synthesis with Phosphate-ON (Clontech Laboratories, Palo Alto, Calif.) according to the manufacturer's instructions or post-synthesis, using T4 polynucleotide kinase (Boehringer Mannheim, Indianapolis, Ind.). In the latter, a common oligomer was diluted into 50 µl of kinase buffer (50 mM Tris/HCl, 10 mM MgCl$_2$, and 1 mM ATP) to a final concentration of 1 mM (500 pmol in 50 µl). Ten units of T4 kinase was added, and the reaction was incubated at 37° C. for 30 min. The T4 kinase was inactivated by heating at 95° C. for 10 min.

The kinase reaction was carried out as follows:

| 10 µl | 50 mM common oligo |
| 5 µl | 10x kinase buffer |

-continued

| 5 µl | 10 mM ATP |
| 30 µl | H20 |
| 50 µl | Total |
| + 1 µl | T4 Kinase (10 units) |

37° C. for 30 min.
95° C. for 10 min.
Final concentration = 10 mM

Example 9

Multiplex PCR Amplification

Twelve gene regions (2-13) were chosen for simultaneous PCR amplification based on information available in the Human Genome Database, as shown below in Table 10.

TABLE 10

List of Polymorphic Sites Analyzed

| Site Number | Locus Symbol | Locus Name | Chr. Location | Nucleotide Position | Variation | Het. | Ref. |
|---|---|---|---|---|---|---|---|
| 1 | CYP2D6 | cytochrome P450IID6 | 22q13.1 | 4469 (M33388) | C, T | .38 | 2 |
| 2 | AT3 | antithrombin III | 1q23–q25.1 | 7987 (X68793) | C, T | .46 | 3 |
| 3 | C6 | complement component C6 | 5p14–p12 | 185 (X72179) | A, C | .47 | 4 |
| 4 | IL1A | interleukin 1 alpha | 2q13 | 6282 (X03833) | T, G | .34 | 5 |
| 5 | NF1 | neurofibromatosis | 17q11.2 | 63683 (L05367) | A, G | .47 | 6 |
| 6 | ALDOB | aldolase B | 9q22.3–q31 | 1087 (M15656) | A, G | .50 | 7 |
| 7 | A2M | alpha 2 macroglobulin | 12p13.3–p12.3 | 153 (X68731) | G, A | .42 | 8 |
| 8 | IGF2 | insulin growth factor | 11p15.5 | 820 (X07868) | G, A | .46 | 9 |
| 9 | PROS1 | protein S alpha | 3p11–cen | 183 (M36564) | A, G | .50 | 10 |
| 10 | LIPC | triglyceride lipase | 15q21–q23 | 113 (M29189) | T, G | .49 | 11 |

TABLE 10-continued

List of Polymorphic Sites Analyzed

| Site Number | Locus Symbol | Locus Name | Chr. Location | Nucleotide Position | Variation | Het. | Ref. |
|---|---|---|---|---|---|---|---|
| 11 | CD18 | integrin B-2 subunit | 21q22.3 | 109 (X64081) | C, T | .50 | 12 |
| 12 | LDLR | low density lipoprotein receptor | 19p13.2 | 70 (L00344) | G, A | .50 | 13 |

The site numbers are specific single point variations located within the respective genes. All variations indicated are defined on the sense strand. Genbank accession numbers are indicated in parentheses. Chr., chromosome; Het., heterozygosity.
References in Table 10
2 M. Armstrong, et al., "A Polymorphic Cfo I Site In Exon 6 of the Human Cytochrome P450 CYPD6 Gene Detected by the Polymerase Chain Reaction," Human Genetics 91: 616–17 (1993), which is hereby incorporated by reference.
3 S. C. Bock, et al., "Antithrombin III Utah: Proline-407 to Leucine Mutation in a Highly Conserved Region Near the Inhibitor Reactive Site," Biochemistry 28: 3628 (1991), which is hereby incorporated by reference.
4 G. Dewald, et al., "Polymorphism of Human Complement Component C6: An Amino Acid Substitution (glu/ala) Within the Second Thrombospondin Repeat Differentiates Between the Two Common Allotypes C6 A and C6 B," Biochem. Biophys. Res. Commun. 194: 458–64 (1993), which is hereby incorporated by reference.
5 P. A. Velden, et al., "Amino Acid Dimorphism in IL1A is Detectable by PCR Amplification," Hum. Mol. Genet. 2: 1753 (1993), which is hereby incorporated by reference.
6 R. M. Cawthon, et al., "Identification and Characterization of Transcripts From Theneurofibromatosis 1 Region: The Sequence and Genomic Structure of EV12 and Mapping of Other Transcripts," Genomics 7: 555–65 (1990), which is hereby incorporated by reference.
7 C. C. Brooks, et al., "Association of the Widespread A149P Hereditary Fructose Intolerance Mutation With Newly Identified Sequence Polymorphisms in the Aldolase B Gene," Am. J. Human Genetics 52: 835–40(1993), which is hereby incorporated by reference.
8 W. Poller, et al., "Sequence Polymorphism in the Human Alpha-2-Macroglobulin (A2M) Gene," Nucleic Acids Res. 19: 198 (1991), which is hereby incorporated by reference.
9 T. Gloudemans, "An Ava II Restriction Fragment Length Polymorphism in the Insulin-Like Growth Factor II Gene and the Occurrence of Smooth Muscle Tumors," Cancer Res. 53: 5754–58 (1993), which is hereby incorporated by reference.
10 C. M. Diepstraten, et al., "A CCA/CCG Neutral Dimorphism in the Codon for Pro 626 of the Human Protein S Gene PSa (PROS1)," Nucleic Acids Res. 19: 5091 (1991), which is hereby incorporated by reference.
11 M. Reina, et al., "SSCP Polymorphism in the Human Hepatic Triglyceride Lipase (LIPC) Gene," Hum. Mol. Genet. 1: 453 (1992), which is hereby incorporated by reference.
12 S. Mastuura, et al., "Investigation of the Polymorphic AvaII Site by a PCR-based Assay at the Human CD18 Gene Locus," Human Genetics 93: 721 (1994), which is hereby incorporated by reference.
13 L. Warnich, et al., "Detection of a Frequent Polymorphism in Exon 10 of the Low-Density Lipoprotein Receptor Gene," Human Genetics 89: 362 (1992), which is hereby incorporated by reference.

Each region was well characterized and harbored a single-base variation with only two known alleles. PCR amplifications were performed using genomic DNA isolated from whole blood using the Purgene DNA Isolation Kit (Gentra Systems, Inc., Minneapolis, Mich.) according to the manufacturer's instructions.

A volume of 25 µl of PCR buffer (10 mM Tris/HCl pH 8.3, 10 nM KCl, 4 mM MgCl$_2$, 0.4 mM each dNTP), 10-100 ng of genomic target DNA, PCR hybrid primer pairs 1-12 (2 pmol of each primer), and 1.3 units of AmpliTaq DNA polymerase Stoffel fragment (Applied Biosystems) was placed in a thin-walled MicroAmp reaction tube (Applied Biosystems). Each hybrid primer consisted of a gene-specific 3' region (16-29 bases) and a 5' region (22 bases) corresponding to one of two sets of universal (i.e. the portions which are primer-specific) primers (See FIG. 4, where F1=Tet, F2=Fam, and F3=Het). These primers are shown in Table 11.

TABLE 11

Primary PCR Primer Sequences

| Number or Name | Primer (5' -> 3') | | |
|---|---|---|---|
| 1 | F | GGAGCACGCTATCCCGTTAGACAGCCAAGGGGAACCCTGAGAG | (SEQ. ID. NO. 49) |
|   | R | CGCTGCCAACTACCGCACTATGATCGTGGTCGAGGTGGTCACCATC | (SEQ. ID. NO. 50) |
| 2 | F | CCTCGTTGCGAGGCGTATTCTGTATTTCCTCTTCTGTAAAAGGGAAGTTTGT | (SEQ. ID. NO. 51) |
|   | R | GCGACCTGACTTGCCGAAGAACATGTCCCATCTCCTCTACCTGATAC | (SEQ. ID. NO. 52) |
| 3 | F | GGAGCACGCTATCCCGTTAGACTAAAGATCTGTCTTGCGTCCCAGTCA | (SEQ. ID. NO. 53) |
|   | R | CGCTGCCAACTACCGCACTATGTATCAATTTTGCAGAGCTTAGATGGAATG | (SEQ. ID. NO. 54) |

TABLE 11-continued

Primary PCR Primer Sequences

| Number or Name | | Primer (5' -> 3') | |
|---|---|---|---|
| 4 | F | CCTCGTTGCGAGGCGTATTCTGTAGCACTTGTGATCATGGTTTTAGAAATC | (SEQ. ID. NO. 1) |
| | R | GCGACCTGACTTGCCGAAGAACTATCGTATTTGATGATCCTCATAAAGTTG | (SEQ. ID. NO. 56) |
| 5 | F | GGAGCACGCTATCCCGTTAGACATCAGCCACTTGGAAGGAGCAAAC | (SEQ. ID. NO. 57) |
| | R | CGCTGCCAACTACCGCACTATGATGGACCATGGCTGAGTCTCCTTTAG | (SEQ. ID. NO. 58) |
| 6 | F | CCTCGTTGCGAGCCGTATTCTGAACCAACACGGAGAAGCATTGTTTTC | (SEQ. ID. NO. 59) |
| | R | GCGACCTGACTTGCCGAAGAACTATTAGCCTCAATCCTCATACTGACCTCTAC | (SEQ. ID. NO. 60) |
| 7 | F | GGAGCACGCTATCCCGTTAGACATCTCCTAACATCTATGTACTGGATTATCTAAATG | (SEQ. ID. NO. 61) |
| | R | CGCTGCCAACTACCGCACTATGATCTTACTCAAGTAATCACTCACCAGTGTTG | (SEQ. ID. NO. 62) |
| 8 | F | CCTCGTTGCGAGGCGTATTCTGAATGAGTCAAATTGGCCTGGACTTG | (SEQ. ID. NO. 63) |
| | R | GCGACCTGACTTGCCGAAGAACTTAATTCCCGTGAGAAGGGAGATG | (SEQ. ID. NO. 64) |
| 9 | F | CCTCGTTGCGAGGCGTATTCTGAAGGATCTGGATGAAGCCATTTCTAAAC | (SEQ. ID. NO. 65) |
| | R | GCGACCTGACTTGCCGAAGAACTTGGAAAAGGTATTATAAGCAGAGAAAAGATG | (SEQ. ID. NO. 66) |
| 10 | F | GGAGCACGCTATCCCGTTAGACAGGACCGCAAAAGGCTTTCATC | (SEQ. ID. NO. 67) |
| | R | CGCTGCCAACTACCGCACTATGTAGCACCCAGGCTGTACCCAATTAG | (SEQ. ID. NO. 68) |
| 11 | F | CCTCGTTGCGAGOCGTATTCTGATCGGGCGCTGGGCTTCAC | (SEQ. ID. NO. 69) |
| | R | GCGACCTGACTTGCCGAAGAACATCAGATGCCGCACTCCAAGAAG | (SEQ. ID. NO. 70) |
| 12 | F | GGAGCACGCTATCCCGTTAGACATAAGAGCCCACGGCGTCTCTTC | (SEQ. ID. NO. 1) |
| | R | CGCTGCCAACTACCGCACTATGTAAGAGACAGTGCCCAGGACAGAGTC | (SEQ. ID. NO. 72) |
| ZipALg1 | F | GGAGCACGCTATCCCGTTAGAC | (SEQ. ID. NO. 73) |
| ZipBLg2 | R | CGCTGCCAACTACCGCACATG | (SEQ. ID. NO. 74) |
| ZipCLg3 | F | CCTCGTGCGAGGCGTATTCTG | (SEQ. ID. NO. 75) |
| ZipDLg4 | R | GCGACCTGACTTGCCGAAGAAC | (SEQ. ID. NO. 76) |

Solid underline denotes the ZipALg1 and ZipBLg2 sequences. Dotted underline denotes the ZipCLg1 and ZipDLg2 sequences. Linker sequences are indicated in bold. F = forward, R = reverse.

Forward and reverse hybrid primers for loci 1, 3, 5, 7, 10, and 12 contained 5' end regions identical to universal primers ALg1 and BLg2 respectively. Forward and reverse primers to loci 2, 4, 6, 8, 9, and 11 contained 5' end regions identical to universal primers CLg3 and DLg4, respectively. The rationale for using a low concentration of the hybrid primers in the PCR phase was to deplete the hybrid primers during the reaction. This would theoretically allow products with low amplification efficiencies to "catch up with" those that had high amplification efficiencies. Amplification was attained by thermal cycling for 1 cycle of 96° C. for 15 sec to denature, then 15 cycles of 94° C. for 15 sec to denature and 65° C. for 60 sec to anneal and extend.

An equal volume of PCR buffer containing a high concentration of the two pairs of universal primers (25 pmol of each primer; Table 2) and 1.3 units of Amplitaq DNA polymerase Stoffel fragment was added to the Microamp reaction tube, and thermal cycling was performed for another 25 cycles with the annealing temperature lowered to 55° C. The upstream universal primers ALg1 and CLg3 were fluorescently labeled with 6-FAM and TET, respectively. All thermal cycling was achieved with a GeneAmp PCR System 9600 thermal cycler (Applied Biosystems).

The primary PCR process was carried out under the following conditions:

| | |
|---|---|
| 5.9 µl | $H_2O$ |
| 5 µl | primer pairs 1–12 (2 pmol each primer) |
| 2.5 µl | 10X Stoffel fragment |
| 4 µl | 25 mM $MgCl_2$ |
| 5 µl | 2 mM dNTP stock (each) |
| 2.5 µl | genomic DNA (10 ng) |
| 0.13 µl | Stoffel Frag. (1.3 units) |
| 25 µl | Total |

The primary PCR cycling conditions were as follows:
96° C. 15"
94° C. 15", 65° C. 1'×15
65° C. Hold The secondary PCR process was carried out under the following conditions:

| | |
|---|---|
| 13.37 µl | H$_2$O |
| 5 µl | zip primer pairs (25 pmol each primer) |
| 2.5 µl | 10X Stoffel fragment |
| 4 µl | 25 mM MgCl$_2$ |
| 0.13 µl | Stoffel Frag. (1.3 units) |
| 25 µl | Total |

The secondary PCR cycling conditions were as follows:

94° C. 15", 55° C. 1'×25

4° C. Hold

Figure 28A:
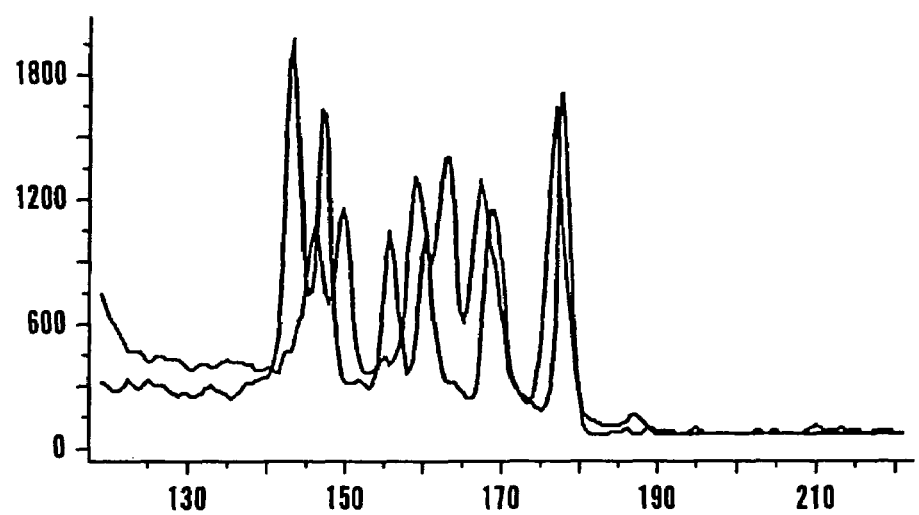
FIGS. 28A-C show electropherogram results for the PCR phase of a primary PCR/secondary PCR/LDR process. Multiplex PCR amplification of 12 loci using primary PCR oligonucleotide primers produces approximately equal amounts of product. Over 80 gene regions with single-base polymorphisms were identified from the Human Genome Database. Twelve of these (see Table 10 and FIGS. 29A-H) were amplified in a primary PCR phase as follows: Long primary PCR oligonucleotide primers were designed to have gene-specific 3' ends and 5' ends complementary to one of two sets of secondary PCR oligonucleotide primers. The upstream primary PCR oligonucleotide primers were synthesized with either FAM (i.e. 6-carboxyfluorescein; fluorescent dye used in sequencing and mutation detection) or TET (i.e. tetrachlorinated-6-carboxytluorescein; fluorescent dye used in sequencing/mutation detection) fluorescent labels. All 24 base long primary PCR oligonucleotide primers were used at low concentration (2 picomole of each primer in 20 µl) in a 15 cycle primary PCR phase. After this, the two sets of secondary PCR oligonucleotide primers were added at higher concentrations (25 picomoles of each) and the secondary PCR phase was conducted for an additional 25 cycles. The products were separated on a 373 DNA Sequencer (Applied Biosystems). Panel A shows the electropherogram results for the FAM- and TET-labelled products combined. Panel B shows the FAM-labelled products alone. Panel C shows the TET-labelled products alone. The process produces similar amounts of multiplexed products without the need to adjust carefully primer concentrations or PCR conditions.
Figure 28B:
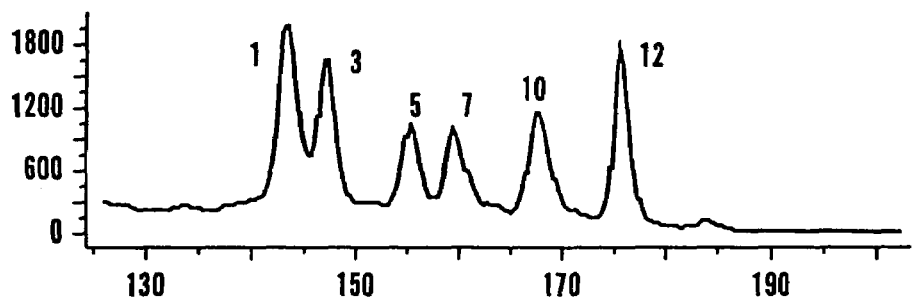
Figure 28C:
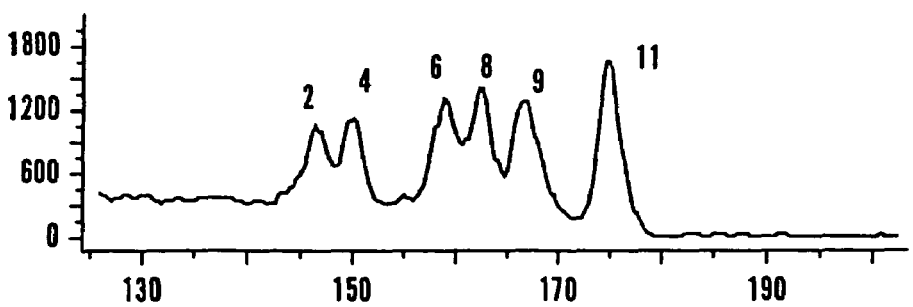
Figure 29A:
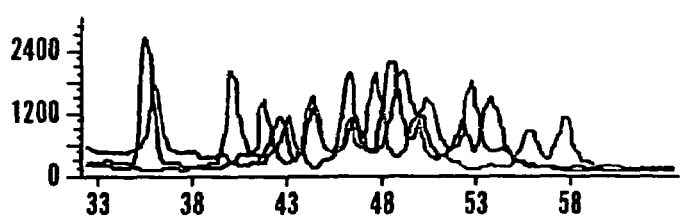
FIGS. 29A-H show electropherogram results for the LDR phase of a primary PCR/secondary PCR/LDR process in detecting 12 biallelic genes for forensic identification. The primary and secondary PCR phases for the 12 polymorphic genes were performed as described in FIG. 28A-C. However, the secondary PCR oligonucleotide primers were not fluorescently labelled. The secondary PCR process extension products were diluted into a ligase buffer containing 36 LDR oligonucleotide probes (one common and two discriminating primers for each locus). LDR oligonucleotide probe sets were designed in two ways: (i) allele-specific oligonucleotide probes were of the same length but contained either the FAM or TET label; or (ii) the allele-specific oligonucleotide probes were both labelled with HEX (i.e. hexachlorinated-6-carboxyfluorescein; fluorescent dye used in sequencing and mutation detection) but differed in length by two basepairs. After 20 cycles of the LDR phase, the ligation product sequences were resolved using a 10% polyacrylamide sequencing gel on a 373 DNA Sequencer (Applied Biosystems). Panel A and E show the 12 loci PCR/LDR profiles of two individuals. Panels B, C, and D show, respectively, the FAM, TET, and HEX data for the individual in panel A. Panels F, G, and H show, respectively, the FAM, TET, and HEX data for the individual in panel E. The individual in panel A is homozygous only at locus6 (ALDOB (i.e. aldolase B)) and locus 8 (IGF (i.e. insulin growth factor)). The individual in panel E is heterozygous only at loci 3 (C6 (i.e. complement component C6)), 5 (NF1 (i.e. neurofibromatosis)), 6 (ALDOB), and 8 (IGF). This demonstrates that the primary PCR/primary PCR/LDR process can simultaneously distinguish both homozygous and heterozygous genotypes at multiple positions.
Figure 29B:
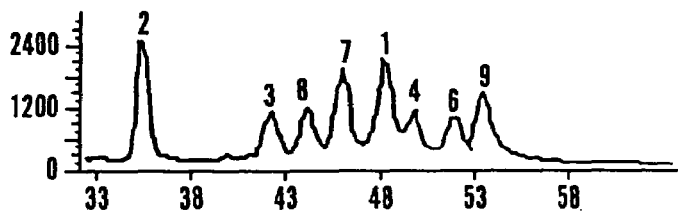
Figure 29C:
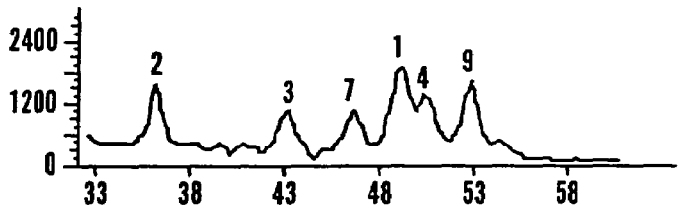
Figure 29D:
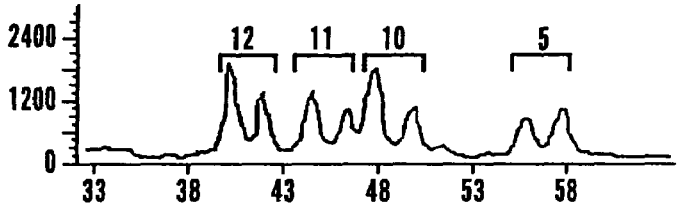
Figure 29E:
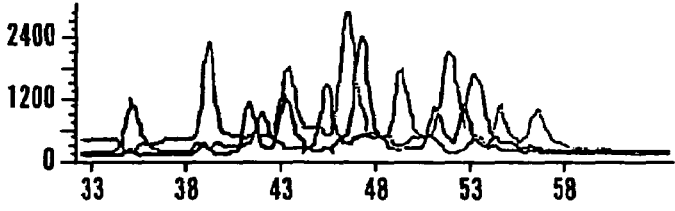
Figure 29F:
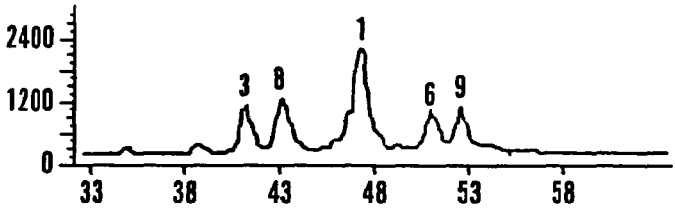
Figure 29G:
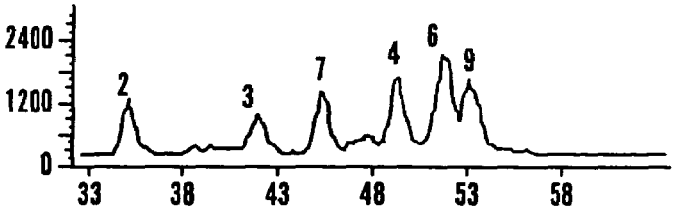
Figure 29H:
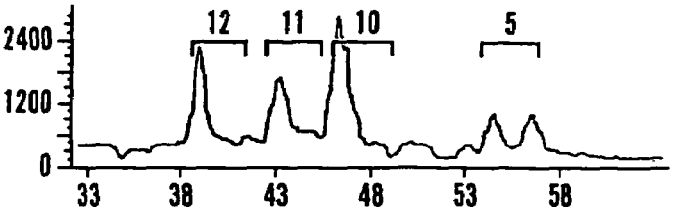

The PCR products were separated on an Applied Biosystems 373 DNA sequencer. A 3 ml aliquot of PCR sample was mixed with 3 ml of formamide containing fluorescently labeled Genescan-2500 [TAMRA] size standard (Applied Biosystems). The formamide/standard solution was prepared by adding 50 ml Genescan-2500 size standard [TAMRA] to 450 ml of formamide. The sample was heated at 95° C. for 2 min, quick cooled in ice, and electrophoresed through a denaturing 8% polyacrylamide gel in an Applied Biosystems 373 DNA sequencer running Genescan version 1.2 software. The sizes of the fluorescently labeled products were automatically computed by the Genescan analysis software using the local Southern method. The electropherograms clearly showed 12 distinct products (FIG. 28). The uniform amount of each product was attributed to the similar size of each amplicon and the use of the primary primers with portions complementary to the secondary primers, which annealed with identical affinities to the 12 amplicons without the need to carefully adjust reaction conditions. The computed sizes of the products, which ranged from 135 to 175 bp, matched exactly to their actual sizes (see Table 12).

TABLE 12

List of PCR and LDR Products

| Site Number | PCR Products | | LDR Product | | | |
|---|---|---|---|---|---|---|
| | Label | Size (bp) | Label | Size (bp) | Variation | Allele |
| 1 | 6-FAM | 143 | 6-FAM | 49 | C | A |
| | | | TET | | T | B |
| 2 | TET | 145 | 6-FAM | 35 | C | A |
| | | | TET | | T | B |
| 3 | 6-FAM | 147 | 6-FAM | 43 | A | A |
| | | | TET | | C | B |
| 4 | TET | 149 | 6-FAM | 51 | T | A |
| | | | TET | | G | B |
| 5 | 6-FAM | 155 | HEX | 56 | A | A |
| | | | | 58 | G | B |
| 6 | TET | 157 | 6-FAM | 53 | A | A |
| | | | TET | | G | B |
| 7 | 6-FAM | 159 | 6-FAM | 47 | G | A |
| | | | TET | | A | B |
| 8 | TET | 161 | 6-FAM | 45 | G | A |
| | | | TET | | A | B |
| 9 | TET | 165 | 6-FAM | 55 | A | A |
| | | | TET | | G | B |
| 10 | 6-FAM | 167 | HEX | 48 | T | A |
| | | | | 50 | G | B |
| 11 | TET | 173 | HEX | 44 | C | A |
| | | | | 46 | T | B |
| 12 | 6-FAM | 175 | HEX | 40 | G | A |
| | | | | 42 | A | B |

The dual labeling approach (Table 12) made it much easier to distinguish the products on the electropherograms (FIG. 28, compare panel A with panels B and C).

Example 10

Multiplex Ligase Detection Reaction

To avoid any possibility of labeled PCR product interfering with the detection of ligation product sequences, PCR product amplified using unlabeled PCR universal primers served as the target for the LDR. The polymerase in the PCR was inactivated by either freeze-thawing or adding EDTA/proteinase K to a final concentration of 5 mM and 100 mg/ml, respectively, and heating to 37° C. for 30 min and 95° C. for 10 min.

Proteinase K digestion was carried out under the following conditions:

| | |
|---|---|
| 20 µl | PCR product |
| + 2.5 µl | 500 mg/ml proteinase K |
| 25 µl | Total |

60° C. for 60 min.
95° C. for 10 min to heat kill proteinase K.

Four microliters of PCR product was diluted in 20 µl of LDR mix containing 50 mM Tris/HCl pH 8.5, 50 mM KCl, 10 mM MgCl$_2$, 1 mM NAD+, 10 mM DTT, LDR oligonucleotide sets 1-12 (200 fmol of each oligonucleotide), and 10 units of *Thermus aquaticus* DNA ligase (Barany, F. and Gelfand, D., "Cloning, Overexpression, and Nucleotide Sequence of a Thermostable DNA Ligase-Encoding Gene," *Gene*, 109:1-11 (1991), which is hereby incorporated by reference). Each LDR oligonucleotide probe set consisted of two allele-specific oligonucleotides and a common oligonucleotide. Each pair of discriminating allele-specific oligonucleotide probes in the LDR oligonucleotide probe sets 1, 2, 3, 4, 6, 7, 8, and 9 were the same size, with one oligonucleotide labeled with 6-FAM and the other labeled with TET. For LDR oligonucleotide probe sets 5, 10, 11, and 12, each pair of allele-specific oligonucleotides differed by 2 bases (the larger oligonucleotide had a 5' tail that was not complementary to the target sequence), and both oligonucleotides were labeled with HEX. Thermal cycling was performed for 1 cycle of 95° C. for 2 min to denature, then 20 cycles of 95° C. for 30 sec to denature, and 65° C. for 4 min to ligate.

The LDR process was carried out as follows:

| | | |
|---|---|---|
| 4 μl | PCR product | |
| 2 μl | LDR oligo sets 1–12 (200 fmol each oligo) | |
| 2 μl | 10X T. ligase buffer | |
| 2 μl | 10 mM NAD+ | |
| 1 μl | 200 mM DTT | |
| 9 μl | H₂O | |
| 20 μl | Total | |
| + 1 μl | Taq Ligase (10 units) | |

Stock of Ligase: 0.5 μl of 625 u/ml + 3.2 μl 10× buffer + 27.5 μl H₂O

LDR cycling conditions were as follows:
94° C. 2'
94° C. 30", 65° C. 4'×20
4° C. Hold A 3 μl aliquot of LDR sample was mixed with 3 μl of formamide containing fluorescently labeled Genescan-2500 [TAMRA] size standard (Applied. Biosystems). The sample was heated at 95° C. for 2 min, quick cooled in ice, and electrophoresed through a denaturing 10% polyacrylamide gel in an Applied Biosystems 373 DNA sequencer running Genescan version 1.2 software. The sizes of the fluorescently labeled products were automatically computed by the Genescan analysis software using the local Southern method. LDR profiles of two individuals are shown in FIG. 29. When each fluorescent dye was analyzed independently (FIG. 29, panels B-D and F-H), it was very easy to determine the alleles present for each locus. A simple "A" or "B" code was assigned to each LDR product (Table 12) and used to score the genotypes. See Table 13 as follows:

TABLE 13

Genotypes Determined by PCR-LDR for 5 Individuals

| | Individual Site Number | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 1 | AB | AB | AB | AB | AB | AB | AB | AA | AA | AB | AB | AB |
| 2 | AA | BB | AB | BB | AB | AB | BB | AA | AB | AA | AA | AA |
| 3 | AB | AB | AB | BB | AA | BB | BB | AA | AA | AB | AB | AA |
| 4 | AA | AB | AA | AB | AB | AA | AB | AA | AB | BB | AB | AA |
| 5 | AA | AA | AA | AB | AB | AB | AB | AB | AA | AB | AB | BB |

The first individual (FIG. 29A-D; Table 13, individual 1) was heterozygous at polymorphic sites 1-7, and 10-12. Heterozygosity at sites 1-4 and 6-7 was indicated by the detection of both 6-FAM and TET labeled products (FIG. 29, panels B and C) at the respective positions on the electropherograms. Heterozygosity at sites 5 and 11-12 was indicated by the presence of two HEX labeled products, differing in size by 2 bases, for each of these loci (FIG. 29, panel D). In contrast, the one product detected at sites 8 and 9 (FIG. 29, panels B and C) established that each of these loci was homozygous. The second individual (FIG. 29E-F and G-H; Table 13, individual 2) was heterozygous only at sites 3, 5, 6, and 9 and homozygous at sites 1, 2, 4, 7, 8, 10-12. There was a total of 8 differences in the genotypes at these positions between the two persons. Three additional individuals were typed, and all 5 persons had distinct genotypes based on the 12 loci (Table 13).

Although the invention has been described in detail for the purpose of illustration, it is understood that such details are solely for that purpose. The variations can be made therein by those skilled in the art without departing from the spirit of the scope of the invention which is defined by the following claims.

What is claimed is:

1. A method for identifying a target nucleotide sequence comprising:
   forming a ligation product on a target nucleotide sequence in a ligation detection reaction mixture, wherein the ligation product comprises an upstream primer portion and a downstream primer portion, wherein the upstream primer portion and the downstream primer portion are not complementary with the target nucleotide sequence;
   amplifying the ligation product to form an amplified ligation product in a polymerase chain reaction (PCR) mixture, wherein the PCR mixture comprises an upstream primer and a downstream primer; and
   detecting the amplified ligation product to identify the target nucleotide sequence.

2. The method according to claim 1 wherein the ligation detection reaction mixture comprises adjacently hybridizing ligation probes.

3. The method according to claim 1 wherein the ligation product results from the ligation of two ligation probes, wherein the two ligation probes are two different molecules.

4. The method according to claim 1, wherein the upstream primer or the downstream primer contains a label.

5. The method according to claim 1, wherein the ligation product can be distinguished from other nucleic acids in the PCR, said method further comprising:
   providing a solid support with different capture oligonucleotides immobilized at different particular sites, wherein the capture oligonucleotides have nucleotide sequences complementary to a unique nucleotide sequence of an extension product.

* * * * *

UNITED STATES PATENT AND TRADEMARK OFFICE
CERTIFICATE OF CORRECTION

| | | |
|---|---|---|
| PATENT NO. | : 7,312,039 B2 | Page 1 of 1 |
| APPLICATION NO. | : 11/590056 | |
| DATED | : December 25, 2007 | |
| INVENTOR(S) | : Barany et al. | |

It is certified that error appears in the above-identified patent and that said Letters Patent is hereby corrected as shown below:

Col. 1 at lines 20-21, delete "This invention was developed with government funding under National Institutes of Health Grant No. GM41337-06. The U.S. Government may retain certain rights." and insert --This invention was made with government support under grant GM41337-06 awarded by the National Institutes of Health. The government has certain rights in the invention-- in its place.

Signed and Sealed this

Fourteenth Day of October, 2008

JON W. DUDAS
*Director of the United States Patent and Trademark Office*